US007820627B2

(12) United States Patent
Jiang et al.

(10) Patent No.: US 7,820,627 B2
(45) Date of Patent: Oct. 26, 2010

(54) LIPID A AND OTHER CARBOHYDRATE LIGAND ANALOGS

(75) Inventors: Zi-Hua Jiang, Edmonton (CA); R. Rao Koganty, Edmonton (CA); Wladyslaw Budzynski, Edmonton (CA)

(73) Assignee: Oncothyreon Inc., Seattle, WA (US)

( * ) Notice: Subject to any disclaimer, the term of this patent is extended or adjusted under 35 U.S.C. 154(b) by 489 days.

(21) Appl. No.: 10/513,556

(22) PCT Filed: May 9, 2003

(86) PCT No.: PCT/US03/14633

§ 371 (c)(1),
(2), (4) Date: Jun. 20, 2005

(87) PCT Pub. No.: WO03/094850

PCT Pub. Date: Nov. 20, 2003

(65) Prior Publication Data

US 2006/0040891 A1 Feb. 23, 2006

Related U.S. Application Data

(60) Provisional application No. 60/378,645, filed on May 9, 2002.

(51) Int. Cl.
*A61K 31/70* (2006.01)
*C07H 15/00* (2006.01)
(52) U.S. Cl. .................. 514/25; 536/4.1; 536/17.2; 536/17.4; 536/17.5; 536/17.8
(58) Field of Classification Search ............ None
See application file for complete search history.

(56) References Cited

U.S. PATENT DOCUMENTS

| 3,930,024 A | 12/1975 | Creger |
| 4,464,383 A | 8/1984 | Yamamoto |
| 4,719,202 A | 1/1988 | van Boeckel et al. |
| 4,912,094 A | 3/1990 | Myers et al. |
| 5,041,427 A | 8/1991 | Takayama et al. |
| 5,191,072 A | 3/1993 | Hasegawa et al. |
| 6,113,918 A | 9/2000 | Johnson et al. |
| 6,136,790 A | 10/2000 | Toepfer et al. |
| 6,316,421 B1 | 11/2001 | Nantz et al. |
| 6,699,846 B2 | 3/2004 | Elliott et al. |
| 6,764,840 B2 | 7/2004 | Johnson et al. |

FOREIGN PATENT DOCUMENTS

| DE | 906 808 | 3/1954 |
| EP | 0 122 151 | 2/1989 |
| JP | 58-10592 | 1/1983 |
| JP | 63-139186 | 6/1988 |
| WO | WO 86/05687 | 10/1986 |
| WO | WO 95/01966 | 1/1995 |
| WO | WO 95/27505 | 10/1995 |
| WO | WO 01/36433 | 5/2001 |
| WO | WO 01/79243 | 10/2001 |
| WO | WO 03/066649 | 8/2003 |
| WO | WO 03/089574 | 10/2003 |

OTHER PUBLICATIONS

Beilstein Abstract, Registry #4885466 (underlying reference 1992).
Beilstein Abstract, Registry #1776862 (underlying reference 1952).
Beilstein Abstract, Registry #1777272 (underlying reference 1953).
Beilstein Abstract, Registry #2299756 (underlying reference 1971).
Beilstein Abstract, Registry #2450963 (underlying reference 1979).
Beilstein Abstract, Registry #2478491 (underlying reference 1979).
Beilstein Abstract, Registry #4386563 (underlying reference 1981).
Beilstein Abstract, Registry #4438100 (underlying reference 1981).
Beilstein Abstract, Registry #4866378 (underlying reference 1992).
Beilstein Abstract, Registry #3310799 (underlying reference 1937).
Beilstein Abstract, Registry #3433270 (underlying reference 1937).
Beilstein Abstract, Registry #7349279 (underlying reference 1988).
Beilstein Abstract, Registry #7349664 (underlying reference 1988).
Beilstein Abstract, Registry #299061 (underlying reference 1950).
Beilstein Abstract, Registry #6129710 (underlying reference 1966).
Beilstein Abstract, Registry #6129784 (underlying reference 1966).
Beilstein Abstract, Registry #1817997, entry date Jun. 29, 1989.
Beilstein Abstract, Registry #1894672, entry date Jun. 29, 1989.
Beilstein Abstract, Registry #2271917, entry date Jun. 29, 1989.
Beilstein Abstract, Registry #1842361, entry date Jun. 29, 1989.
Beilstein Abstract, Registry #2289689, entry date Jun. 29, 1989.
Beilstein Abstract, Registry #2301356, entry date Jun. 29, 1989.
Beilstein Abstract, Registry #4360897, entry date Dec. 2, 1991.
Beilstein Abstract, Registry #7682492, entry date Jul. 31, 1997.
Beilstein Abstract, Registry #7682309, entry date Jul. 31, 1997.
Beilstein Abstract, Registry #7684107, entry date Jul. 31, 1997.
Beilstein Abstract, Registry #7683736, entry date Jul. 31, 1997.
Aguilera, et al., "Novel Disaccharide Inhibitors of Human Glioma Cell Division", *J. Med. Chem.*, vol. 41, pp. 4599-4606, 1998.
Armspach, et al., "Boron-rich metallodendrimers-mix and-match assembly of multifunctional metallosupramolecules", *Chem. Commun.*, vol. 15, pp. 1823-1824, 1996.
Charon, et al., "Chemical synthesis and Immunological Activities of Glycolipids Structurally Related to Lipid A", *Biochemistry*, vol. 24, pp. 2736-2742, 1985.

(Continued)

*Primary Examiner*—Elli Peselev
(74) *Attorney, Agent, or Firm*—Wilson Sonaini Goodrich & Rosati

(57) ABSTRACT

The core structure of pentaerythritol has been used as a replacement for one or both sugars in lipid A, leading to the generation of a series of lipid A analogs. These lipid A analogs may further differ from lipid A with respect to, e.g., the number, nature and location of negatively charged groups, and the number, nature and location of the lipid chains. The lipid A analogs may be lipid A agonists useful as immunostimulatory agents, or lipid A antagonists useful in the treatment of septic shock. In a like manner, a residue of pentaerythritylamine may be used as a replacement for an amino sugar residue in a carbohydrate ligand having a biological activity of interest, generating a series of ligand analogs. These are useful, e.g., as haptens, inhibitors of bacterial-host cell adhesion, etc.

152 Claims, 20 Drawing Sheets

OTHER PUBLICATIONS

Cheng, et al., "Molecular Design of Liquid-Crystalline Block Molecules: Semifluorinated Pentaerythritol Tetrabenzoates Exhibiting Lamellar, Columnar, and Cubic Mesophases", *Angew. Chem. Int. Ed.*, vol. 39, No. 3, pp. 592-595, 2000.

Christ, et al., "E5531, a Pure Endotoxin Antagonist of High Potency", *Science*, vol. 268, pp. 80-83, Apr. 7, 1995.

Donnerstag, et al., "A Structurally and Biogenetically Interesting Moenomycin Antibiotic", *Tetrahedron*, vol. 51, No. 7, pp. 1931-1940, 1995.

Dunn, et al., "Versatile Methods for the Synthesis of Differentially Functionalized Pentaerythritol Amine Derivatives", *J. Org. Chem.*, vol. 55, pp. 6368-6373, 1990.

El-Abadla, et al., "Moenomycin A: The Role of the Methyl Group in the Moenuronamide Unit and a General Discussion of Structure-Activity Relationships", *Tetrahedron*, vol. 55, pp. 699-722, 1999.

Farcy, et al., "A Pentaerythritol-Based Molecular Scaffold for Solid-Phase Combinatorial Chemistry", *Organic Letters*, vol. 3, No. 26, pp. 4299-4301, 2001.

Fehlhaber, et al., "Moenomycin A: A Structural Revision and New Structure-Activity Relations", *Tetrahedron*, vol. 46, No. 5, pp. 1557-1568, 1990.

Ferse, et al., "Acceptor Site Recognition of Transglycosylase Inhibitors A β-D-glucopyranosyl-(1-2)-α-D-glucopyranuronamide-derived Moenomycin Analogue", Tetrahedron, vol. 55, pp. 3749-3766, 1999.

Fujishima, et al., "New synthetic immunomodulators combining a 4-O-phosphono-D-glucos-amine derivative related to bacterial lipid A with 1-deoxy-N-acetylmuramoyl dipeptide analogs", *Carbohydrate Research*, vol. 167, pp. 317-324, 1987.

Goldman, et al., "Differential Antibacterial Activity of Moenomycin Analogues on Gram-Positive Bacteria", *Bioorganic & Medicinal Chemistry Letters*, vol. 10, pp. 2251-2254, 2000.

Hanessian, et al., "Synthesis of clustered D-GalNAc (Tn) and D-Galβ(1-3)GalNac (T) antigenic motifs using a pentaerythritol scaffold", *Can. J. Chem.*, vol. 74, pp. 1738-1747, 1996.

Hebler-Klintz, et al., "The First Moenomycin Antibiotic Without The Methyl-Branched Uronic Acid Constituent. - Unexpected Structure Activity Relations", *Tetrahedron*, vol. 49, No. 35, pp. 7667-7678, 1993.

Hohgardt, et al., "Synthesis of Two Structural Analogues of the Smallest Antibiotically Active Degradation Product of Moenomycin A", *Tetrahedron*, vol. 44, No. 18, pp. 5771-5790, 1988.

Imoto, et al., "Chemical Structure of *Escherichia coli* Lipid A", *Tetrahedron Letters*, vol. 26, No. 7, pp. 907-908, 1985.

Imoto, et al., "Total Synthesis of *Escherichia coli* Lipid A", *Tetrahedron Letters*, vol. 26, No. 12, pp. 1545-1548, 1985.

Jiang, et al., "Novel lipid A mimetics derived from pentaerythritol: synthesis and their potent agonistic activity", *Tetrahedron*, vol. 58, pp. 8833-8842, 2002.

Jiang, et al., "Synthetic Vaccines: The Role of Adjuvants in Immune Targeting", *Current Medicinal Chemistry*, vol. 10, pp. 1423-1439, 2003.

Kiso, et al., "Synthesis of 2-Deoxy-4-O-Phosphono-3-O-Tetradecanoyl-2-[(3R)-And (3S)-3-Tetradecanoyloxytetradecanamido]-D-Glucose: A Diastereoisomeric Pair of 4-O-Phosphono-D-Glucosamine Derivatives (GLA-27) Related to Bacterial Lipid A", *Carbohydrate Research*, vol. 148, pp. 221-234, 1986.

Kotani, et al., "Immunobiological Activities of Synthetic Lipid A Analogs with Low Endotoxicity", *Infection and Immunity*, vol. 54, No. 3, pp. 673-682, Dec. 1986.

Kotani, et al., "Low Endotoxic Activities of Synthetic *Salmonella*-Type Lipid A with an Additional Acyloxyacyl Group on the 2-Amino Group of β(1-6)Glucosamine Disaccharide 1, 4'-Bisphosphate", *Infection and Immunity*, vol. 52, No. 3, pp. 872-884, Jun. 1986.

Kutuzova, et al., "Diphosphoryl Lipid A from *Rhodobacter sphaeroides* Blcks the Binding and Internalization of Lipopolysaccharide in RAW 264.7 Cells", *The Journal of Immunology*, vol. 167, pp. 482-489, 2001.

Kuzdzal, et al., "Dendrimer Electrokinetic Capillary Chromatography: Unimolecular Micellar Behaviour of Carboxylic Acid Terminated Cascade Macromolecules", *J. Chem. Soc., Chem., Commun.*, pp. 2139-2140, 1994.

Lien, et al., "A Novel Synthetic Acyclic Lipid A-like Agonist Activates Cells via the Lipopolysaccharide/Toll-like Receptor 4 Signaling Pathway", *The Journal of Biological Chemistry*, vol. 276, No. 3, pp. 1873-1880, Jan. 19, 2001.

Lindhorst, et al., "Cluster Mannosides as Inhibitors of Type 1 Fimbriae-Mediated Adhesion of *Escherichia coli*: Pentaerythritol Derivatives as Scaffolds", *Eur. J. Org. Chem.*, 2027-2034, 2000.

Martin, et al., "Enzymatic Synthesis Of A Modified Phospholipid And Its Evaluation As A Substrate for B.*Cereus* Phospholipase C", *Bioorganic & Medicinal Chemistry Letters*, vol. 8, pp. 593-596, 1998.

Metten, et al., "The First Enzymatic Degradation Products of the Antibiotic Moenomycin A", *Tetrahedron*, vol. 48, No. 39, pp. 8401-8418, 1992.

Moller, et al., "Moenomycin A—Structure-Activity Relations Synthesis of the D-Galacturonamide Analogue of the Smallest Antibiotically Active Degradation Product of Moenomycin A", *Tetrahedron*, vol. 49, No. 8, pp. 1635-1648, 1993.

Ranganathan, et al., "Self-Assembling, Cystine-Derived, Fused Nanotubes Based on Spirane Architecture: Design, Synthesis, and Crystal Structure of Cystinospiranes", *Journal of the American Chemical Society*, vol. 123, No. 24, pp. 5619-5624, Jun. 20, 2001.

Range, et al., "A Chemoenzymatic Approach towards Moenomycin Structural Analogues", *Tetrahedron*, vol. 53, No. 5, pp. 1695-1706, 1997.

Ribi, et al., "Preparation and Antitumor Activity of Nontoxic Lipid A", *Cancer Immunol Immunother*, vol. 12, pp. 91-96, 1982.

Riedel, et al., "Synthesis And Transglycosylase-Inhibiting Properties Of A Disaccharide Analogue Of Moenomycin A Lacking Substitution At C-4 Of Unit F", *Tetrahedron*, vol. 55, pp. 1921-1936, 1999.

Rietschel, et al., "Bacterial Endotoxic Lipopolysaccharides", vol. I, *Molecular Biochemistry and Cellular Biology*, CRC Press, Boca Raton, 1992, pp. 3-41.

Rietschel, et al., "Bacterial Endotoxin: Chemical Constitution, Biological Recognition, Host Response, and Immunological Detoxification", *R.R. Curr. Top. Microbiol. Immunol.*, vol. 216, pp. 39-81, 1996.

Rietschel, et al., "Concepts of the Chemical Structure of Lipid A", *Reviews of Infectious Disease*, vol. 6, No. 4, pp. 432-438, Jul.-Aug. 1984.

Rietschel, et al., "Structure and conformation of the lipid A component of lipopolysaccharides", *Handbook of Endotoxin*, vol. 1: Chemistry of Endotoxin, Chapter 5, pp. 187-220, 1984.

Ritzeler, et al., "Synthesis of a Trisaccharide Analogue of Moenomycin $A_{12}$ Implications of New Moenomycin Structure-Activity Relationships", *Tetrahedron*, vol. 53, No. 5, pp. 1675-1694, 1997.

Sato, et al., "A Novel Synthetic Lipid A Analog with Low Endotoxicity, DT-5461, Prevents Lethal Endotoxemia", *Infection and Immunity*, vol. 63, No. 8, pp. 2859-2866, Aug. 1995.

Scherkenbeck, et al., "Structures Of Some Moenomycin Antibiotics-Inhibitors of Peptidoglycan Biosynthesis", *Tetrahedron*, vol. 49, No. 15, pp. 3091-3100, 1993.

Schmidt, et al., "Synthesis of Glycolipid Clusters with Pentaerythritol Cores and Different Ethyleneoxy-Spaced Mannose Residues as Terminal Carbohydrates", *Eur. J. Org. Chem.*, pp. 669-674, 2002.

Schromm, et al., "Biological activities of lipopolysaccharides are determined by the shape of their lipid A portion", *Eur. J. Biochem.*, vol. 267, pp. 2008-2013, 2000.

Seydel, et al., "Intrinsic conformation of lipid A is responsible for agonistic and antagonistic activity", *Eur. J. Biochem.*, vol. 267, pp. 3032-3039, 2000.

Strain, et al., "Location of Polar Substituents and Fatty Acyl Chains on Lipid A Precursors from a 3-Deoxy-D-*manno*-octulosonic Acid-deficient Mutant of *Salmonella typhimurium*", *The Journal of Biological Chemistry*, vol. 260, No. 30, pp. 16089-16098, Dec. 25, 1985.

Stryer, Lubert, "Conformation and Dynamics", $2^{nd}$ Ed. W. H. Freemand and Co., New York, p. 74, chapter 4, part 1, 1981.

Takada, et al., "Structure-Function Relationships Of Lipid A", *Molecular Biochemistry and Cellular Biology*, vol. I, chapter 5, pp. 107-134, 1992.

Takada, et al., "Structural Requirements Of Lipid A For Endotoxicity And Other Biological Activities", *CRC Critical Reviews in Microbiology*, vol. 16, issue 6, pp. 477-523, 1989.

Takayama, et al., "Separation and Characterization of Toxic and Nontoxic Forms of Lipid A", *Review of Infectious Diseases*, vol. 6, No. 4, pp. 439-443, Jul.-Aug. 1984.

Toepfer, et al., "Synthesis of Novel Mimetics of the Sialyl Lewis X Determinant", *Tetrahedron Letters*, vol. 36, No. 50, pp. 9161-9164, 1995.

Ulrich, et al., Abstract only, "Monophosphoryl lipid A as an adjuvant. Past experiences and new directions", *Pharm. Biotechnol.*, vol. 6, pp. 495-524, 1995.

Welzel, et al., "Moenomycin A: Further Structural Studies And Preparation Of Simple Derivatives", *Tetrahedron*, vol. 39, No. 9, pp. 1583-1591, 1983.

Welzel, et al., "Moenomycin A: Minimum Structural Requirements For biological Activity", *Tetrahedron*, vol. 43, No. 3, pp. 585-598, 1987.

Welzel, et al., "Preliminary Communication" "Stepwise degradation of moenomycin A", *Carbohydrate Research*, vol. 126, pp. C1-C5, 1984.

Werner, et al., "Immunostimulating agents: what next? A review of their present and potential medical applications", *Eur. J. Biochem.*, vol. 242, pp. 1-19, 1996.

Wörl, et al., "Synthesis of New Liquid Phase Carriers for Use in Large Scale Oligonucleotide Synthesis in Solution", *Tetrahedron*, vol. 55, pp. 2941-2956, 1999.

Beilstein Abstract XP-002337686, for Beilstein registry #8730629, (entry date Apr. 26, 2001).

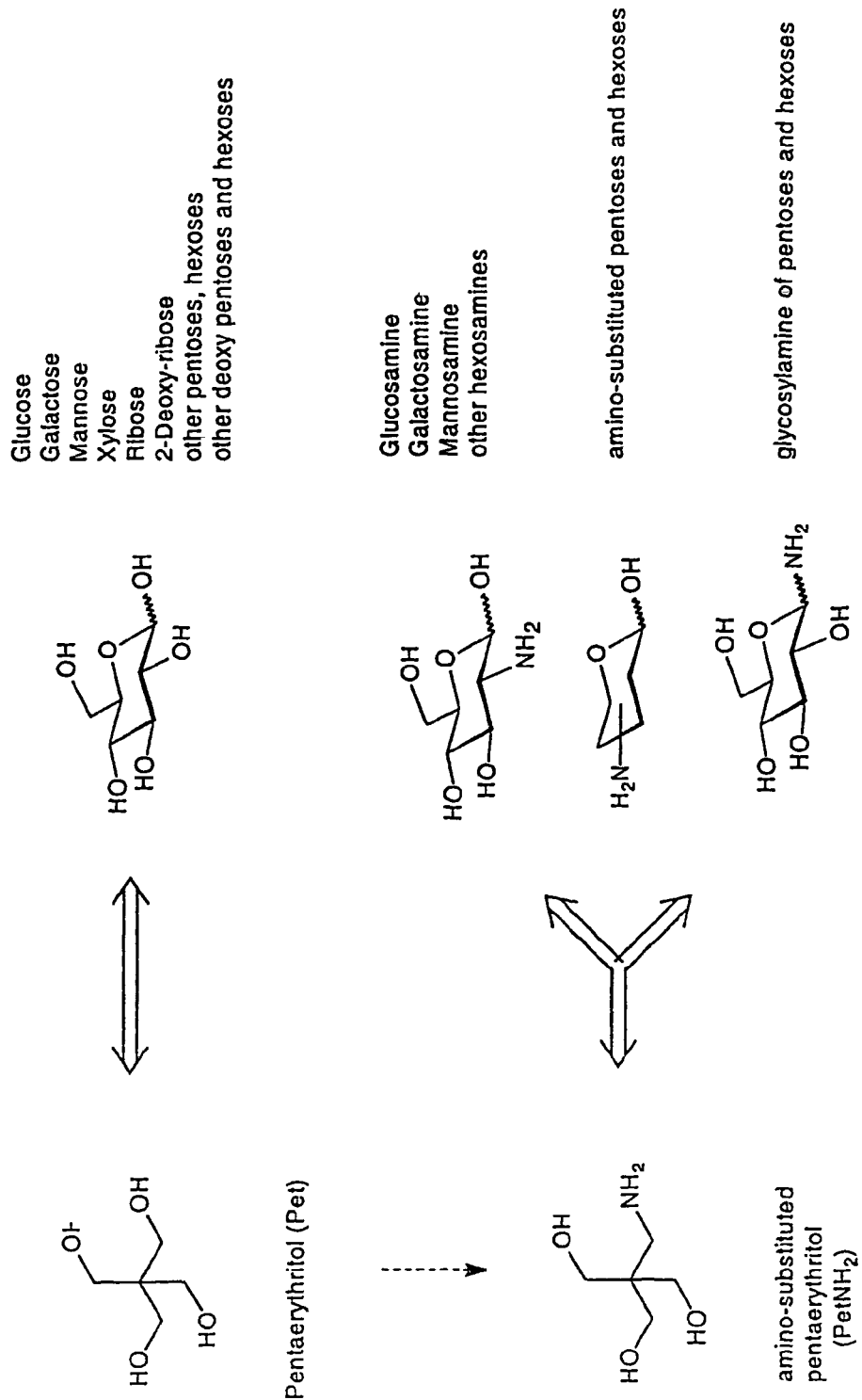
FIG. 1 Pentaerythritol (Pet) and affino-subsfituted pentaerythritol (PetNH2), versatile structural mimics of monosaccharides

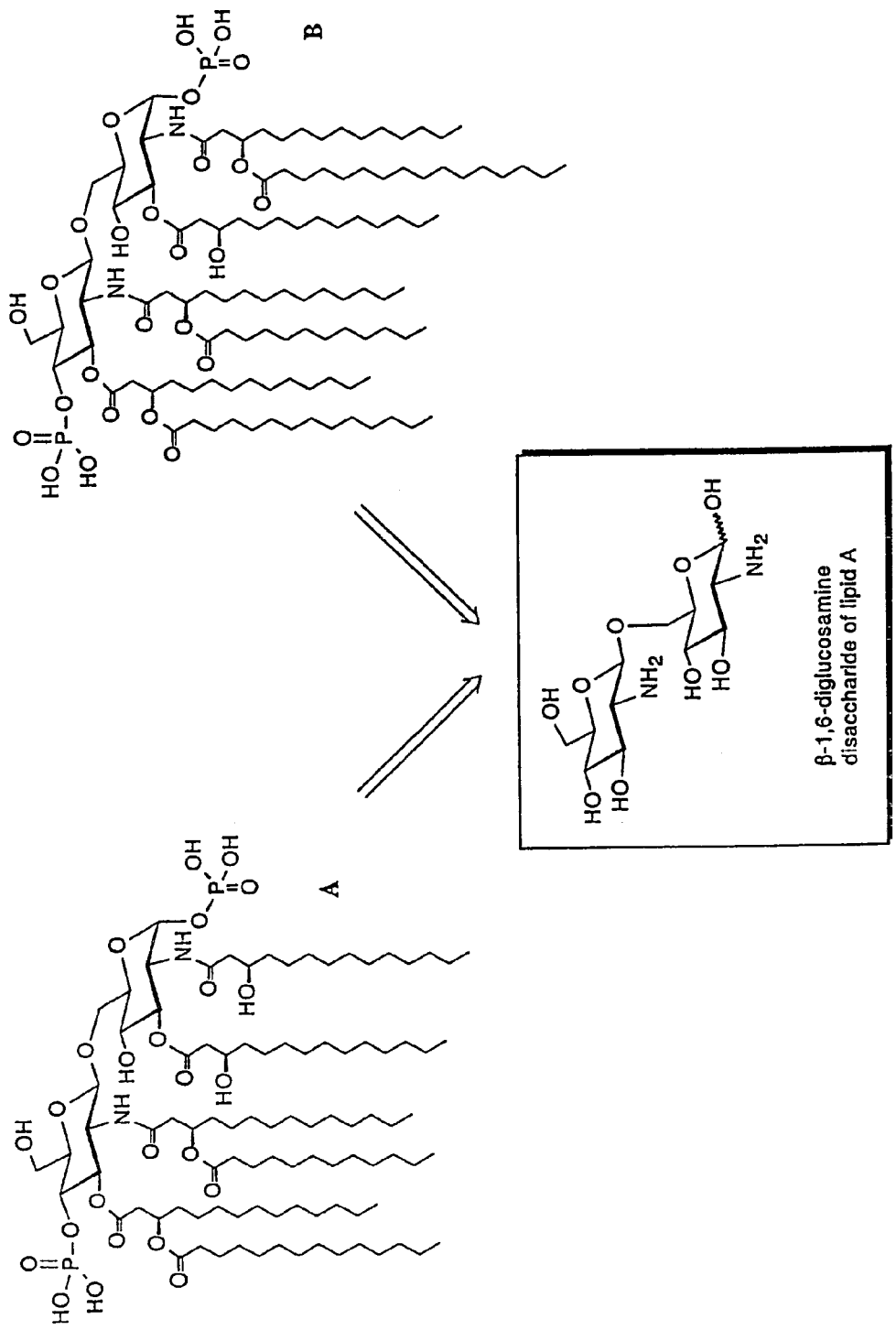
FIG. 2  Examples of natural lipid A structures, A from *E. coli* and B from bacteria *Salmonella*

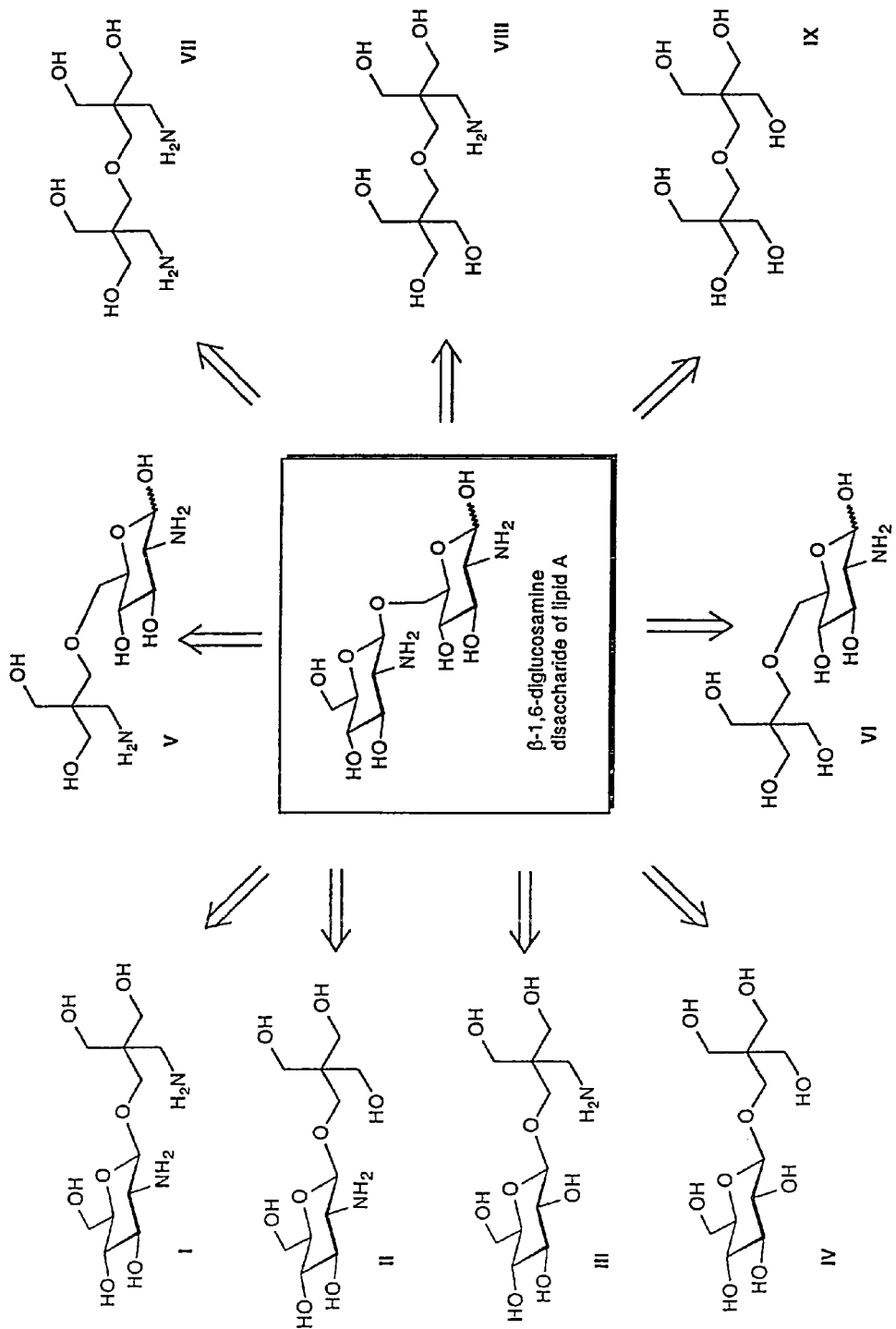
FIG. 3  Pentaerythritol (Pet) and di-pentaerythritol (di-Pet) based structural mimics (I - IX) of lipid A disaccharide β-1,6-diglucosamine FIG. 4  Examples of lipid structures that can be incorported into lipid A molecules

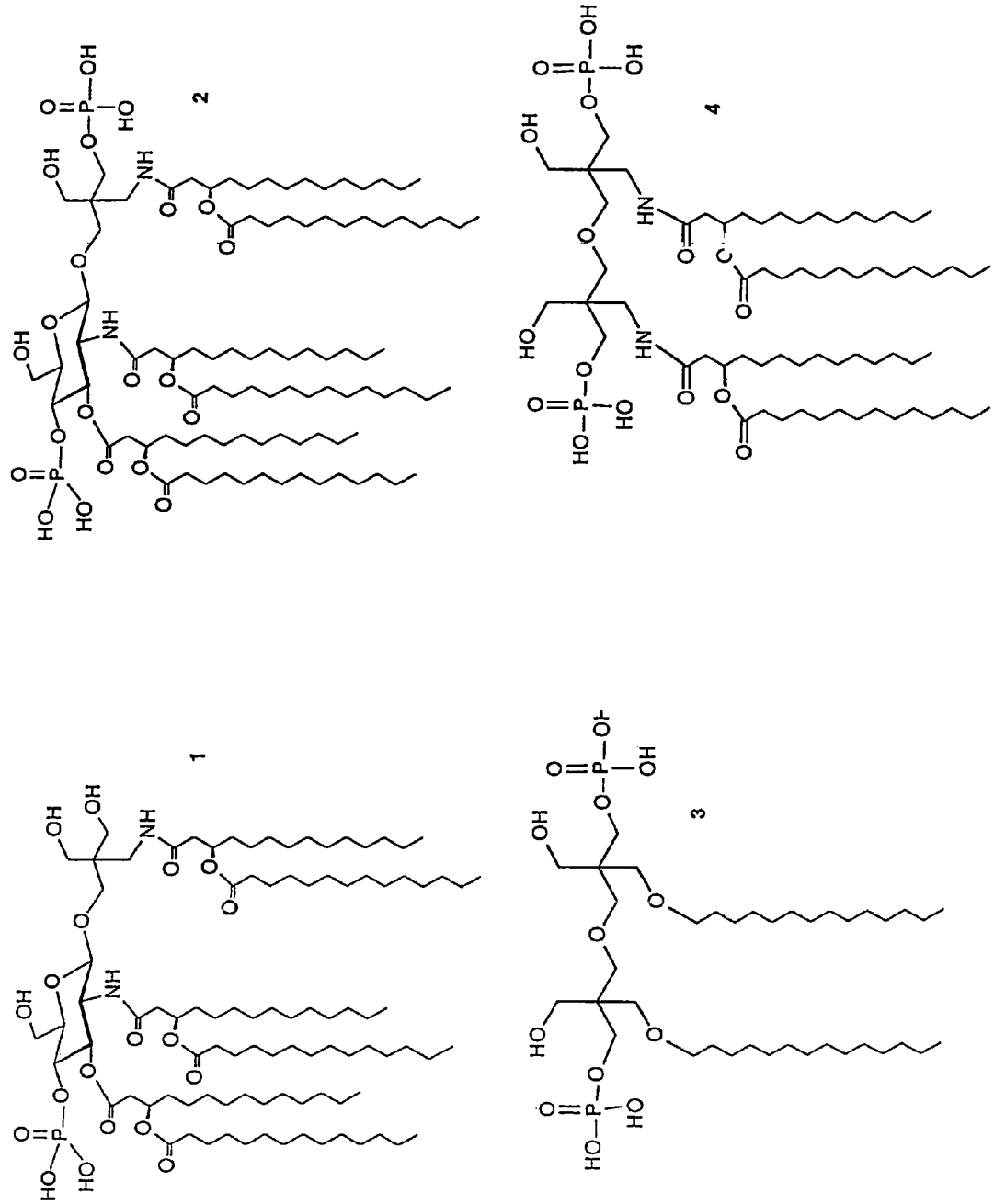
FIG. 5  Examples of Pet-derived lipid A mimics (1 - 4) prepared in this invention disclosure

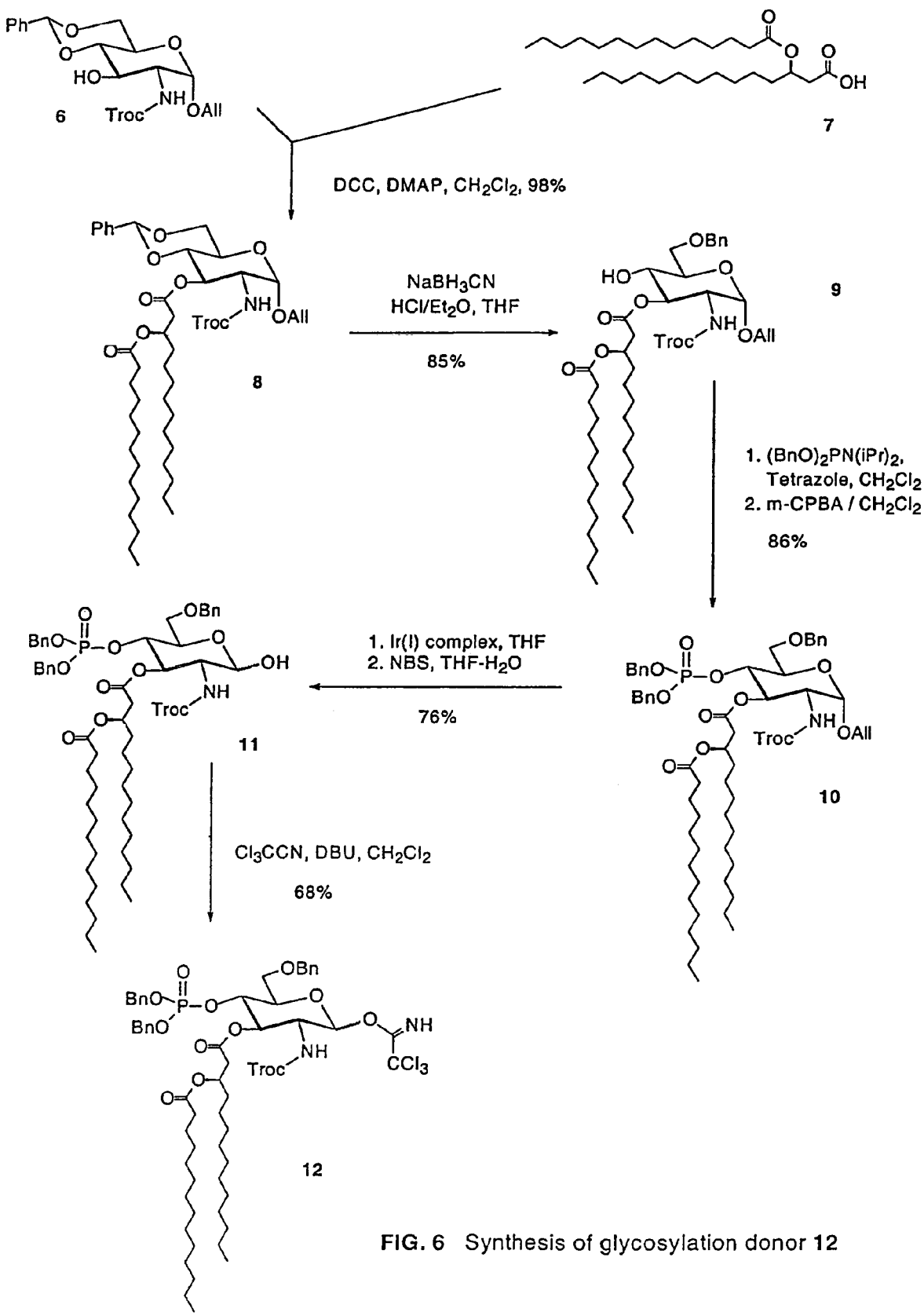
FIG. 6 Synthesis of glycosylation donor 12

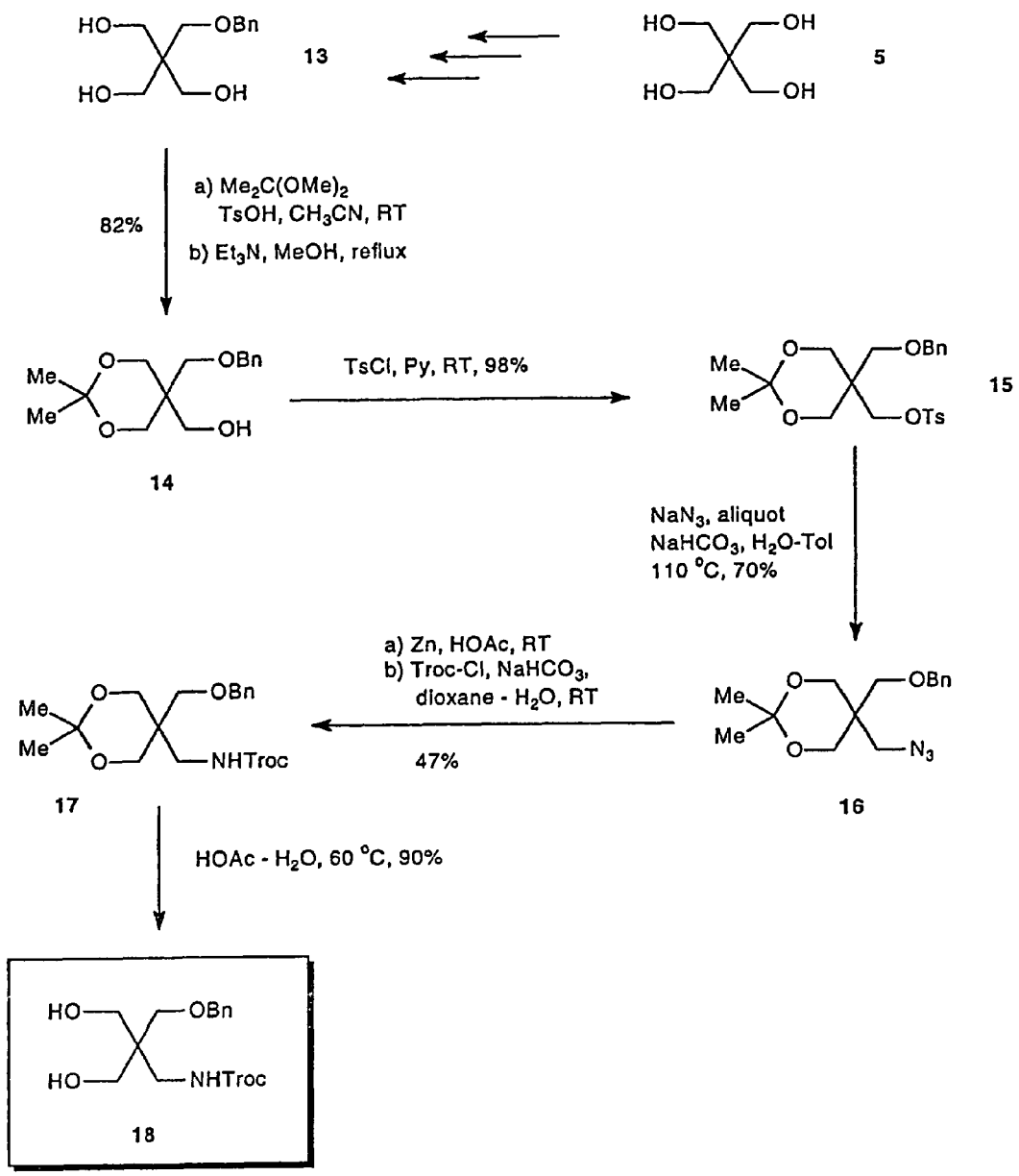
FIG. 7 Preparation of glycosylation acceptor 18

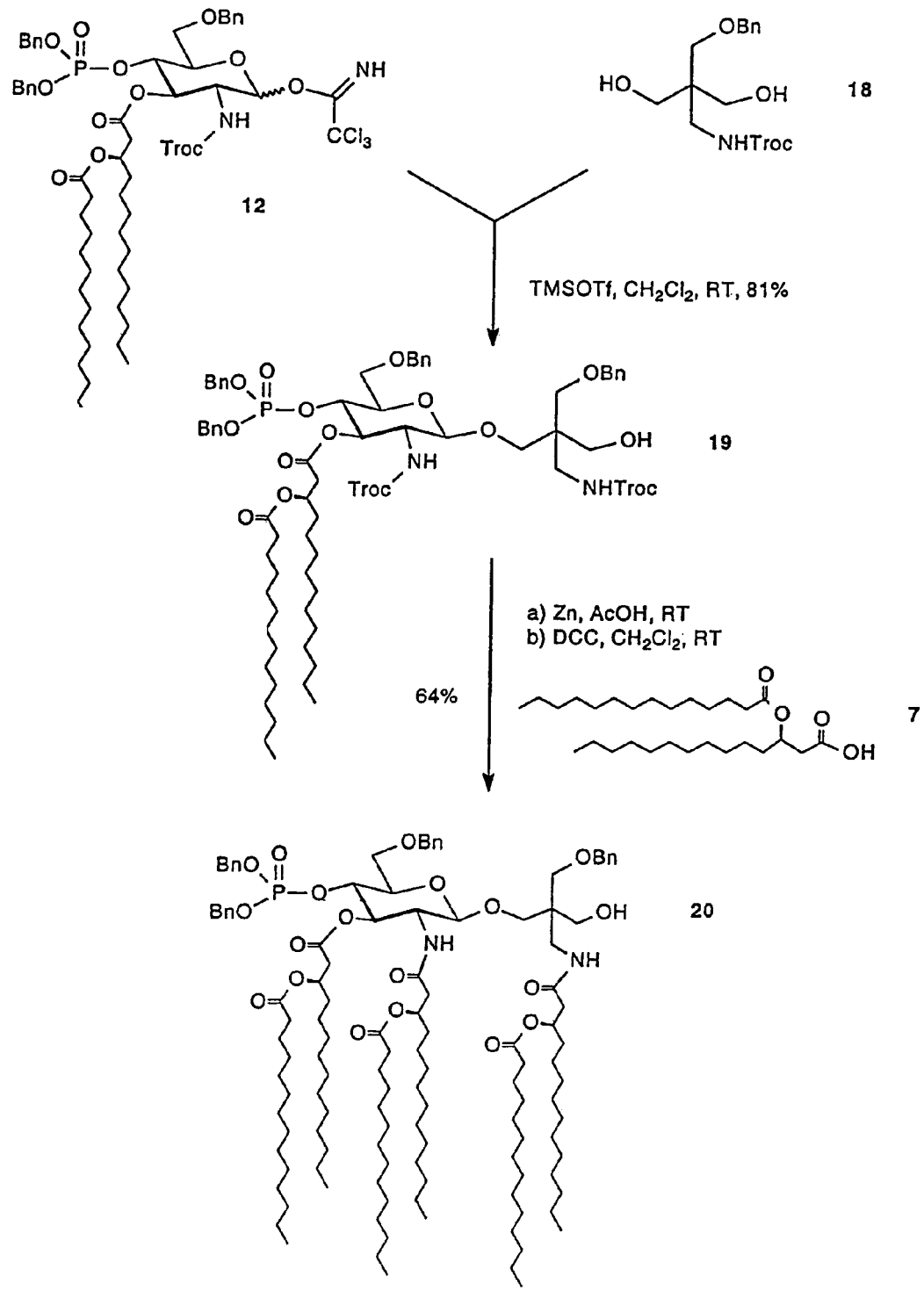
FIG. 8 Synthesis of intermediate 20

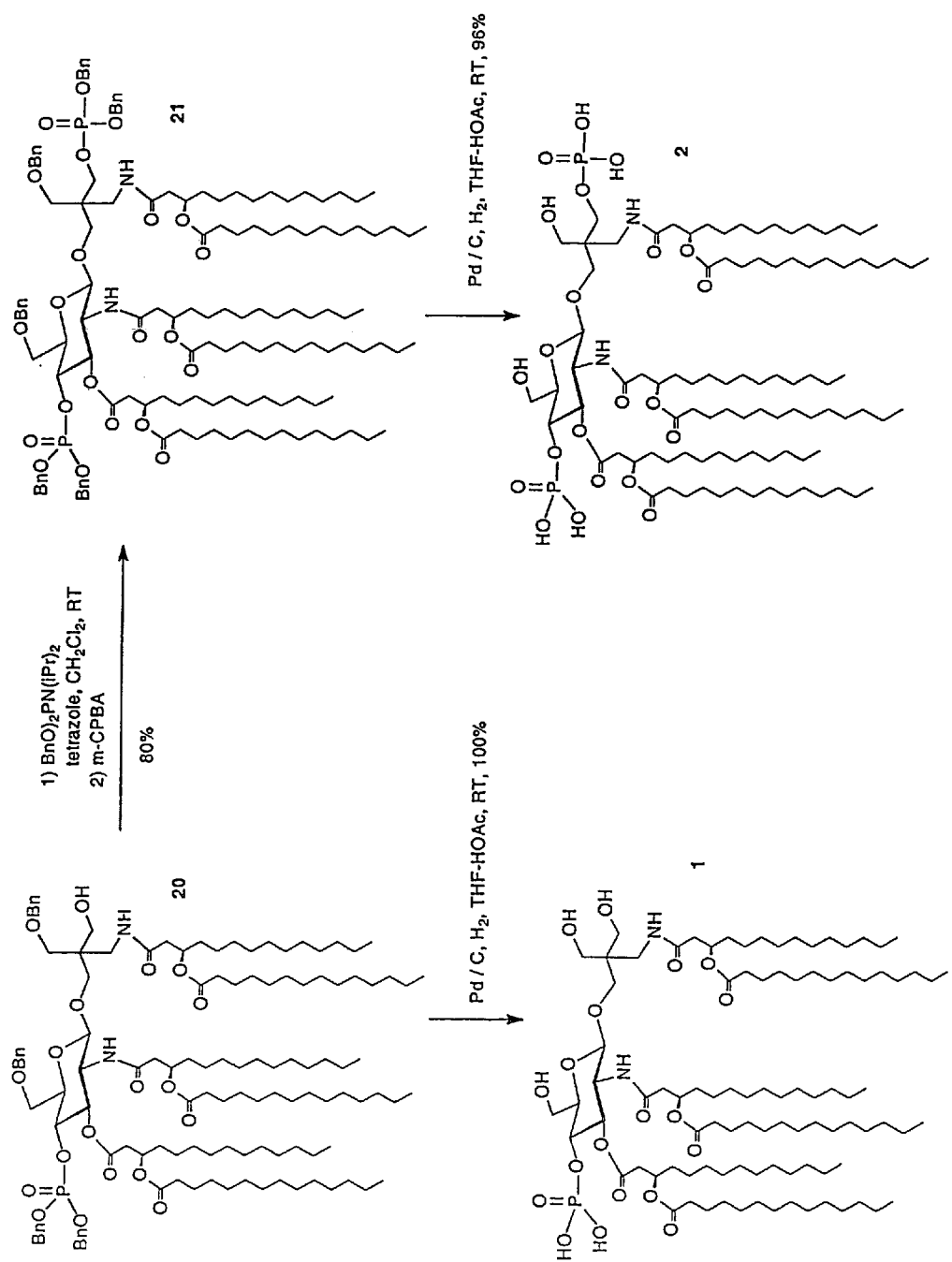
FIG. 9  Synthesis of Pet-based lipid A mimics 1 and 2

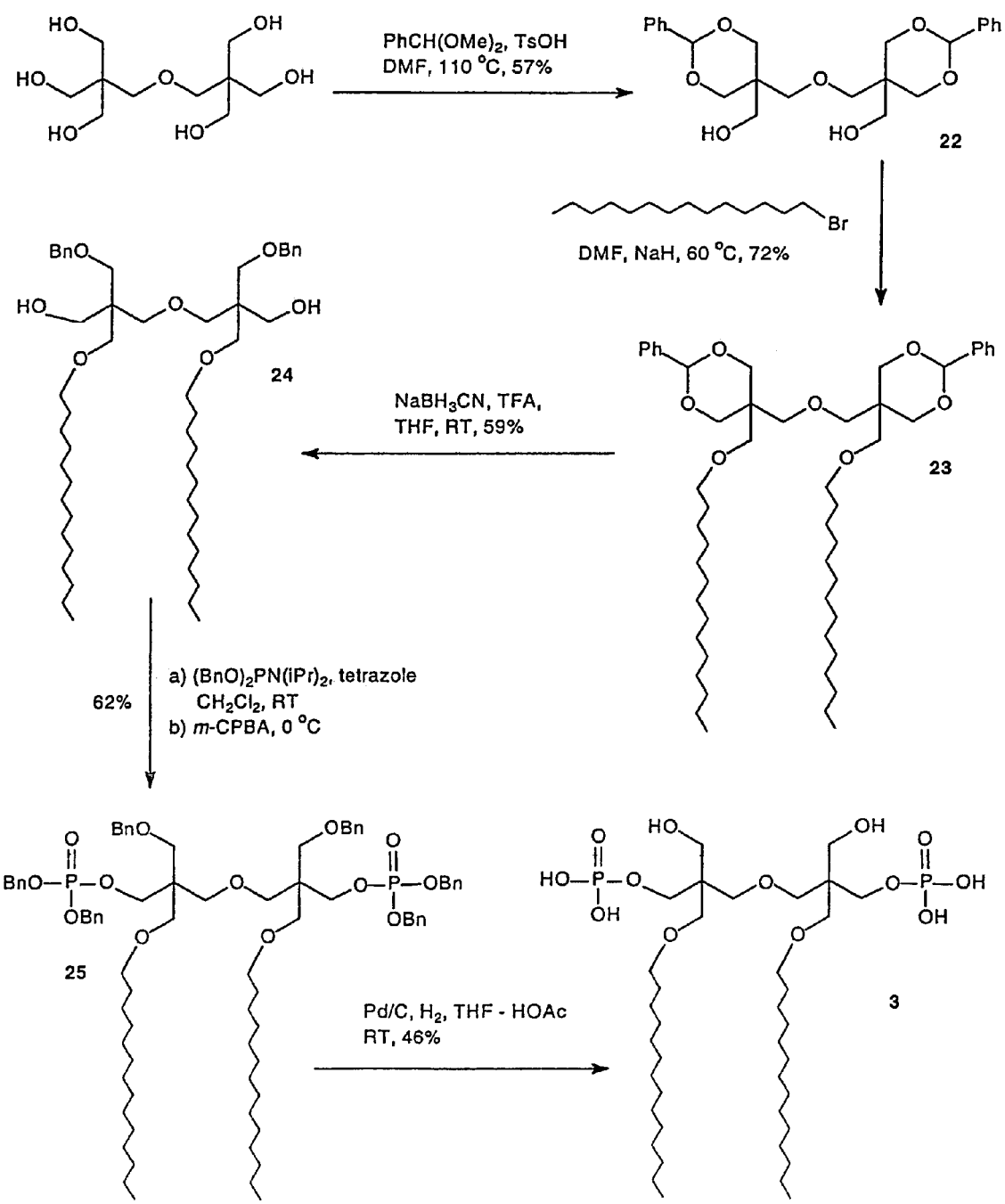
FIG. 10 Synthesis of Di-Pet derived lipid A mimic 3

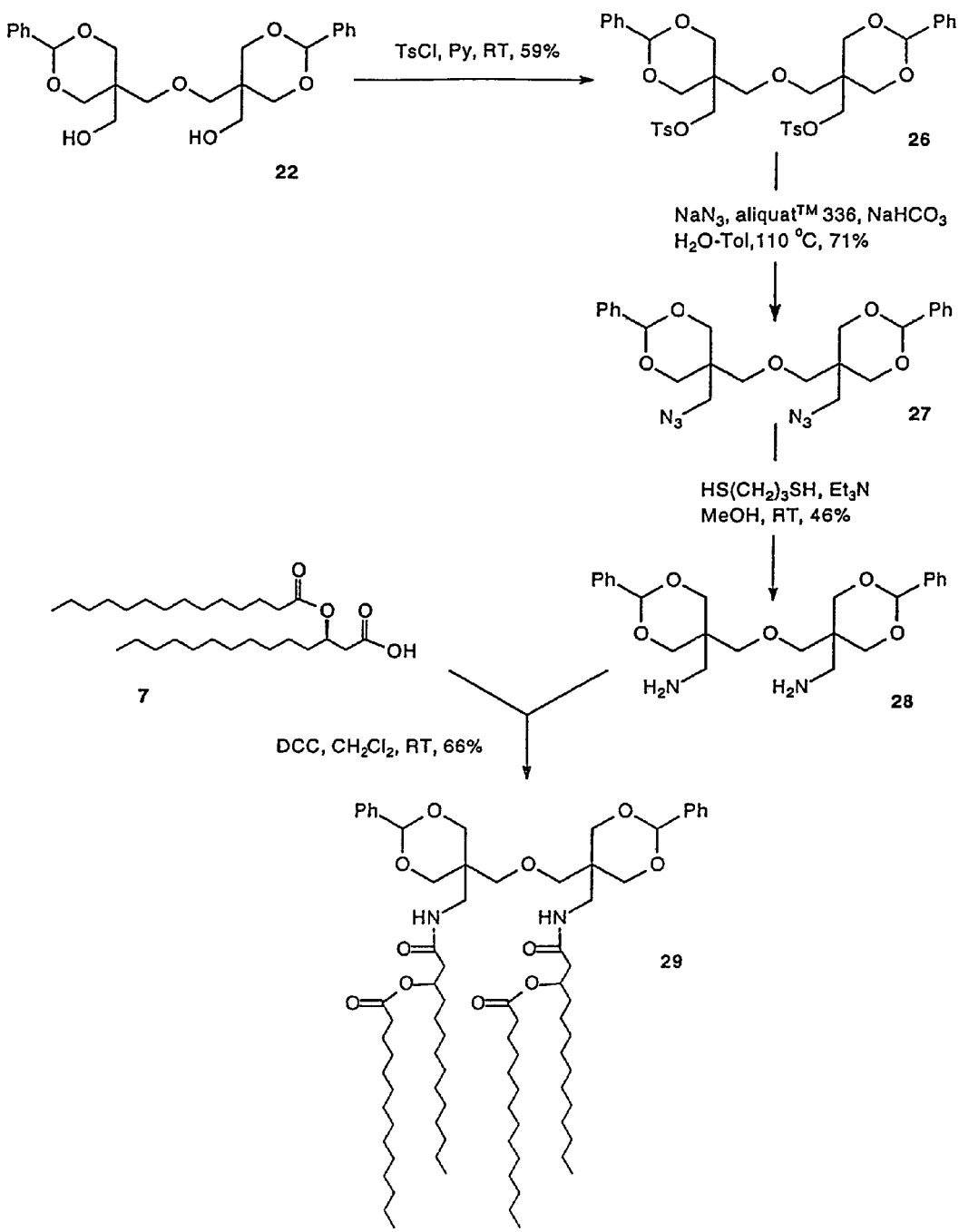
FIG. 11 Synthesis of di-Pet derived lipid A intermediate 29

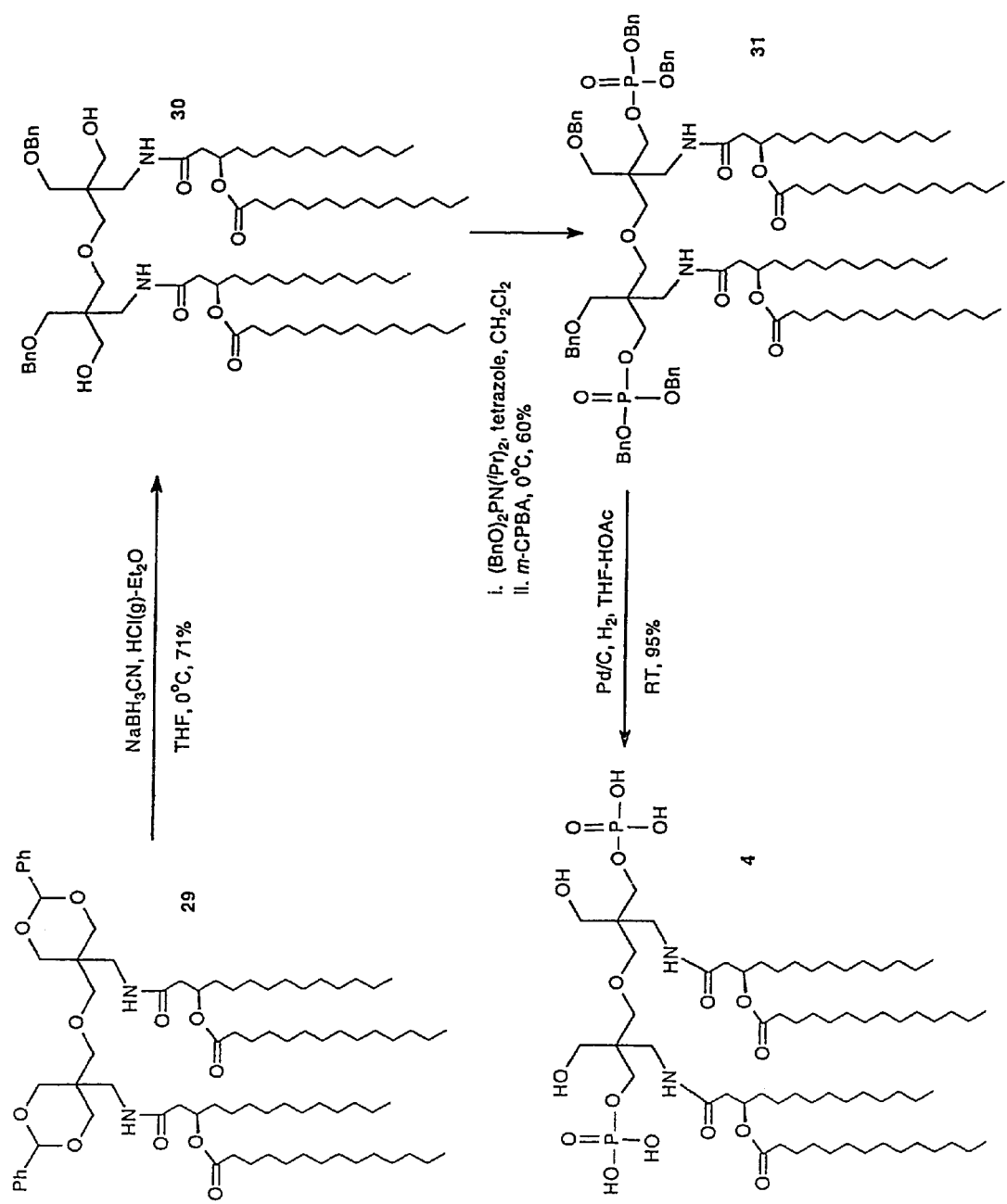
FIG. 12 Synthesis of di-Pet based lipid A mimic 4

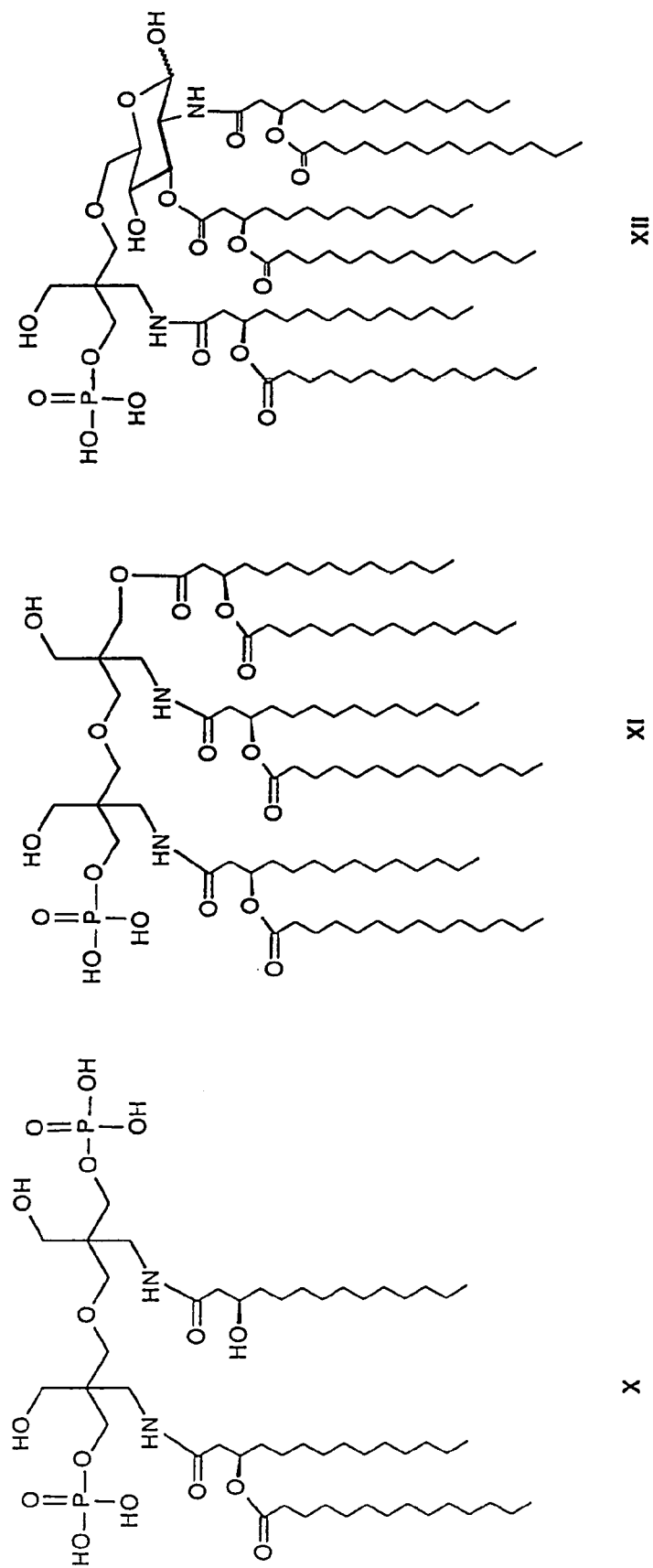
FIG. 13 Some more examples of Pet-derived lipid A mimics (a)
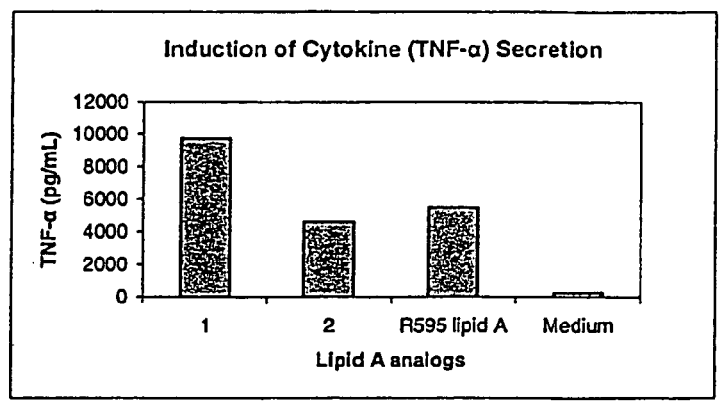
(b)
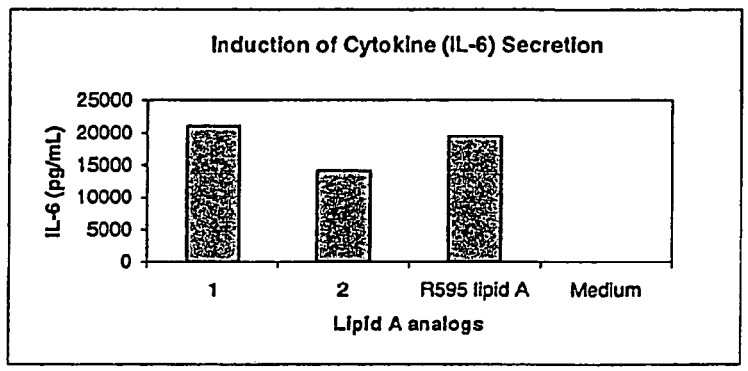
(c)
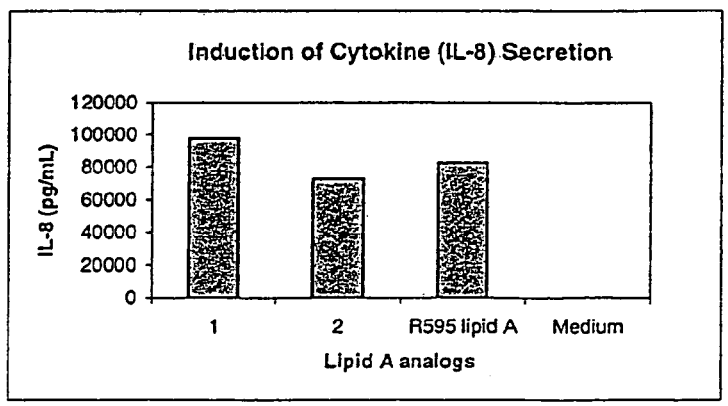
FIG. 14  In vitro cytokine secretion pattern of human adherent cells activated with synthetic lipid A mimic 1, 2 and R595 lipid A. R595 lipid A is a natural product isolated from *Salmonella minnesota*, R595 (Avanti Polar Lipids, Inc.). (a) secrection of tumor-necrosis factor-α (TNF-α, pg/mL); (b) secrection of IL-6 (pg/mL); (c) secrection of IL-8 (pg/mL)

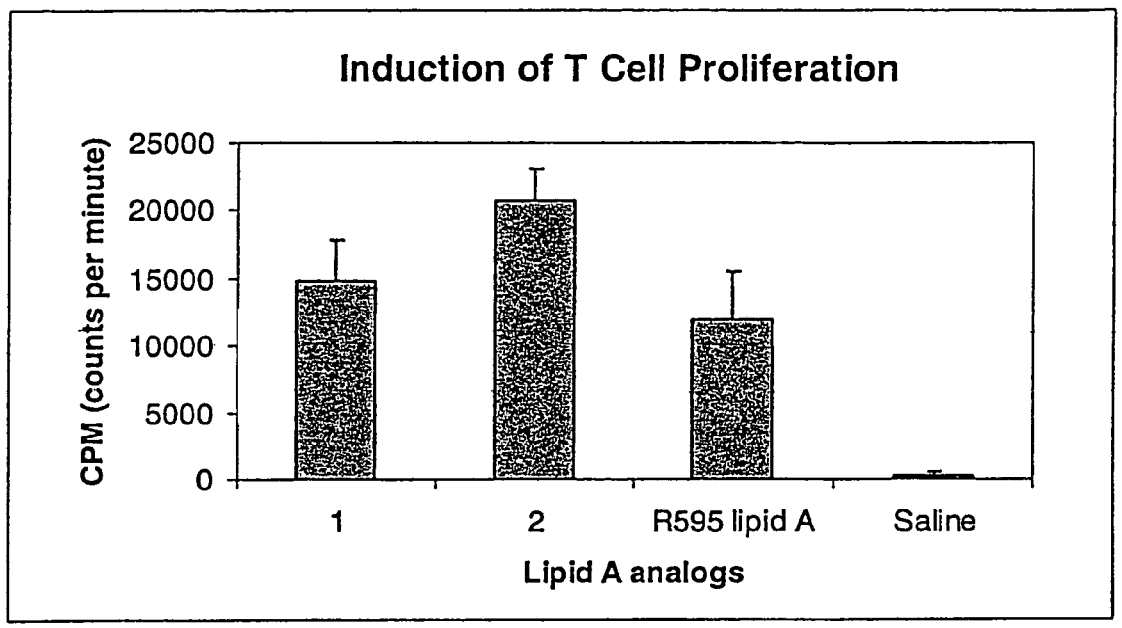
FIG. 15  Antigen specific T cell proliferative response in C57BL/6 mice immunized with BLP25 liposomal vaccine containing lipid A analog. BLP25 liposomal vaccine contains a MUC1 derived 25-mer lipopeptide as tumor antigen and synthetic lipid A mimic 1, 2 or R595 lipid A as an adjuvant.

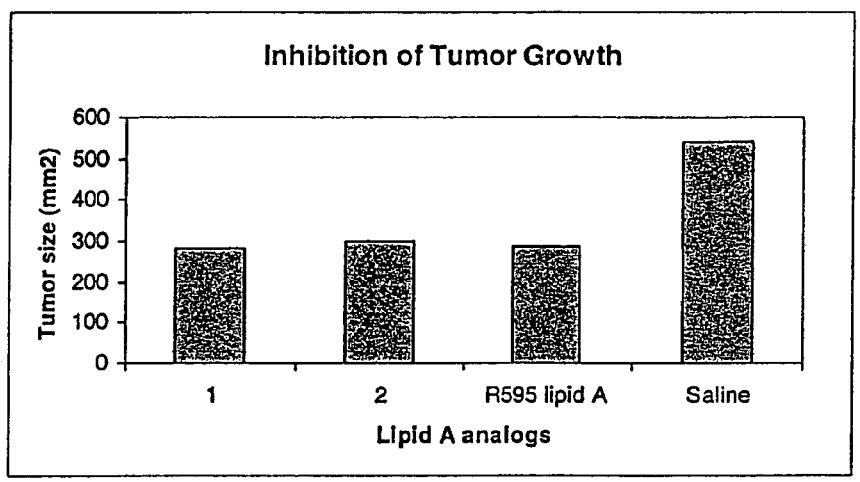

FIG. 16 Active specific immunotherapy of MC-38 MUC1 tumor bearing mice immunized intradermally with BLP25 liposomal vaccine containing lipid A analog. BLP25 liposomal vaccine contains a MUC1 derived 25-mer lipopeptide as tumor antigen and synthetic lipid A mimic 1, 2 or R595 lipid A as adjuvant. Mice were challenged with tumor on day 0 and immunized on day 7, 14 and 21. On day 34, tumor diameters (length & width) were taken and tumor size was expressed as $mm^2$ (length × width).

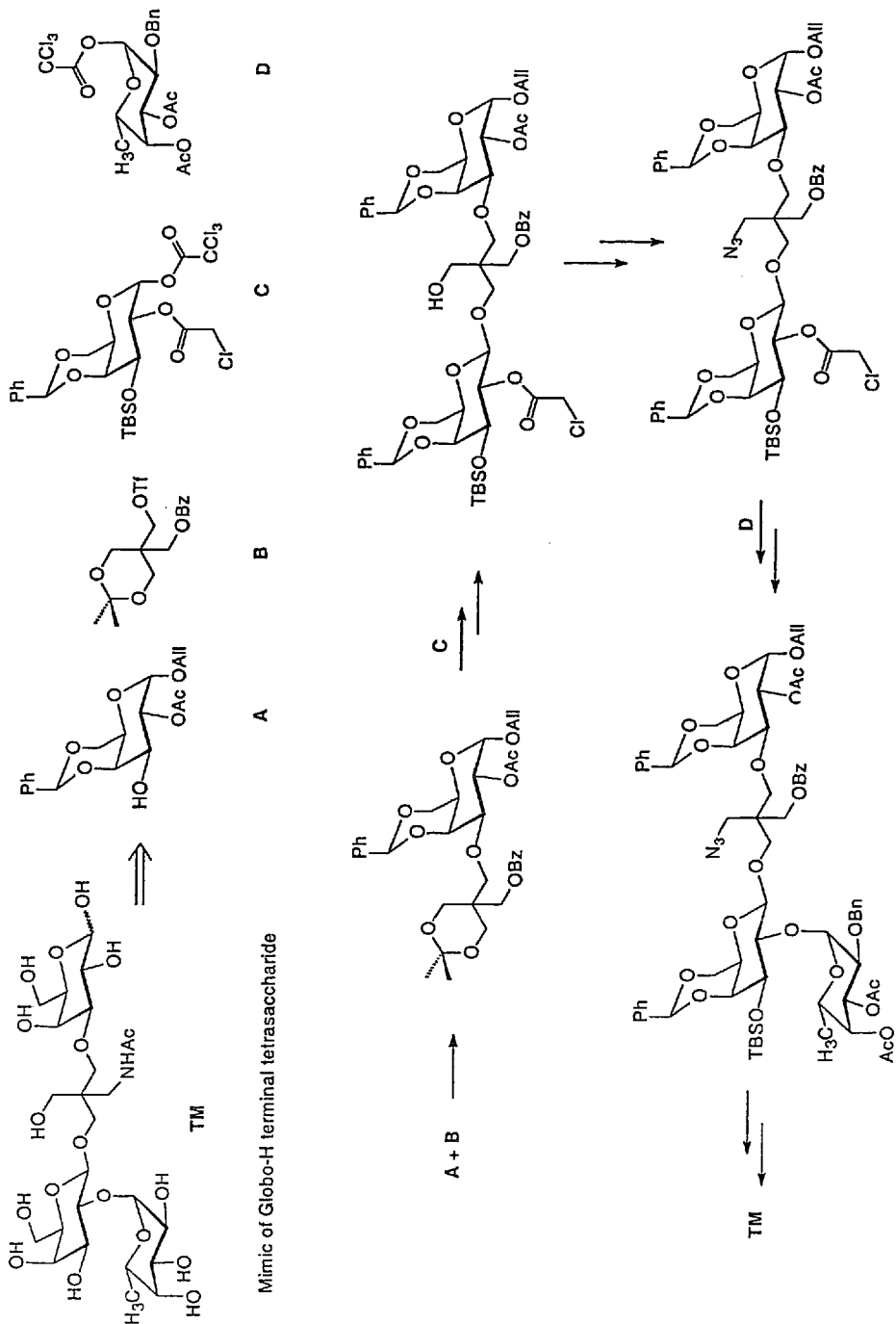
FIG. 17  PetNH₂-containing carbohydrate mimic (TM) of Globo-H terminal tetrasaccharide, a tumor-associated antigen, and its synthetic strategy H2N-STAPPAHGVTSAPPDTRPAPGSTAPPK(Pal)G-OH
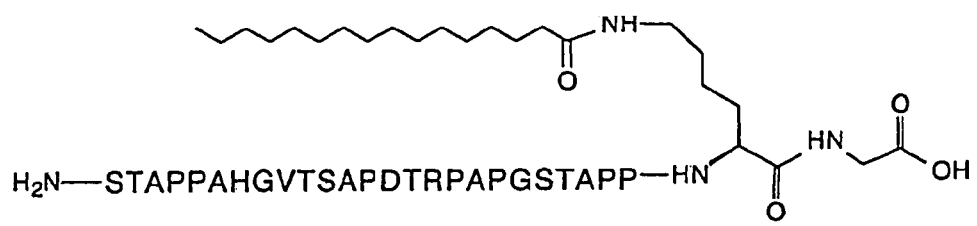
BLP25 lipopeptide
FIG. 18  Structure of lipopeptide BLP25, a modified 25-amino-acid sequence derived from tumor-associated MUC1 mucin (single letter codes of amino acids)

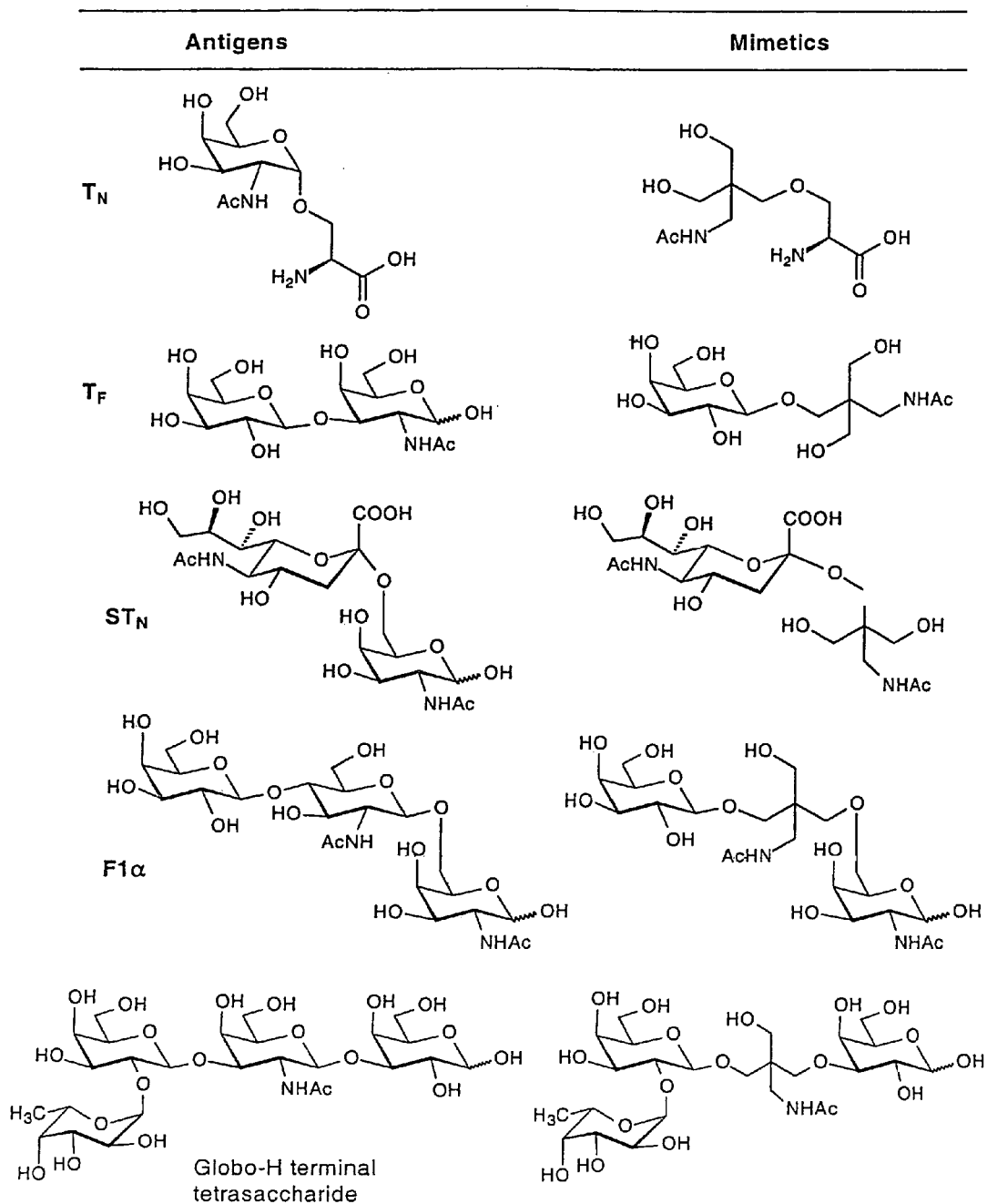
FIG. 19 Tumor-associated carbohydrate antigens and their PetNH₂-containing mimetics

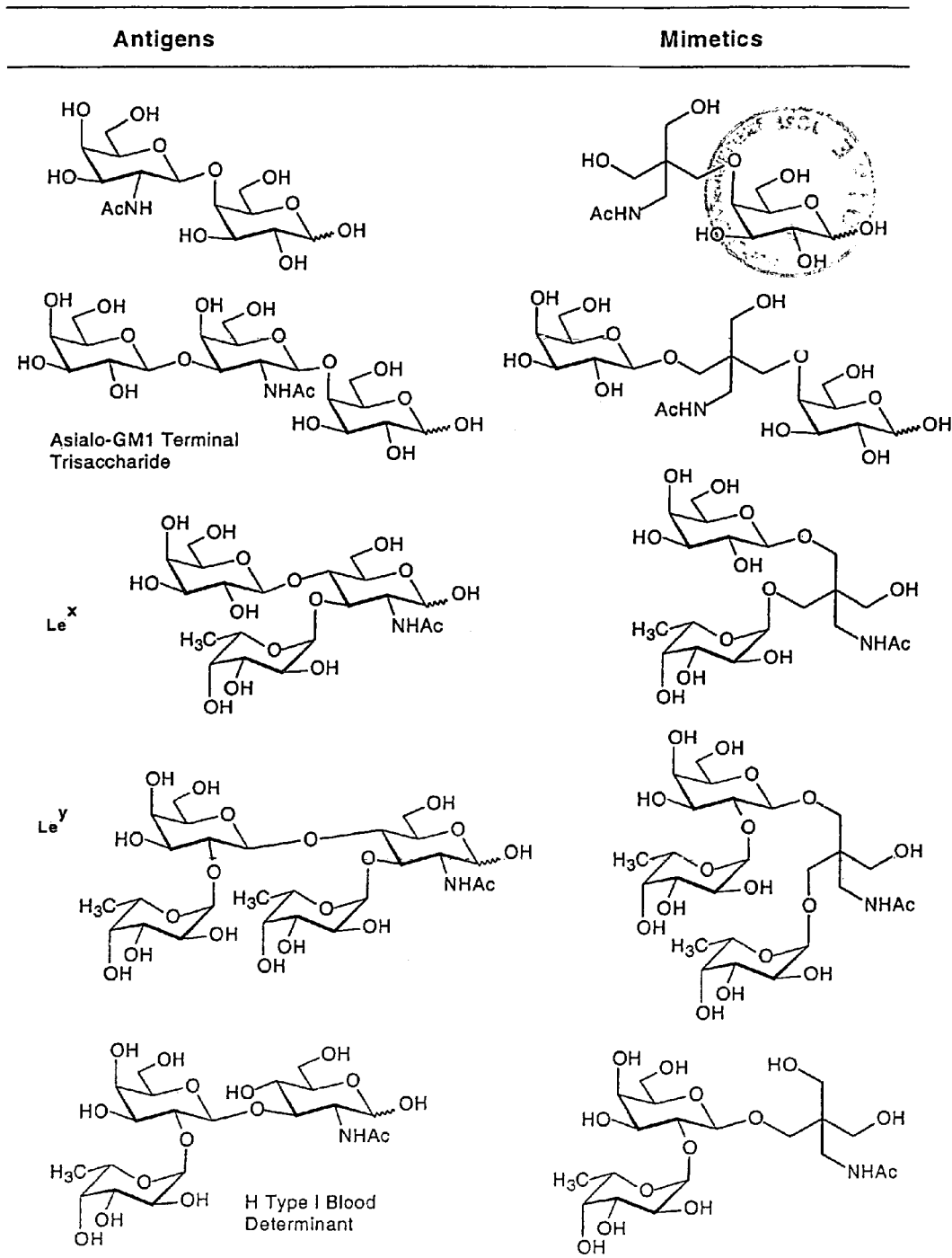
FIG. 20 Carbohydrate antigens involved in bacteria-host adhesion and their PetNH$_2$-containing mimetics

LIPID A AND OTHER CARBOHYDRATE LIGAND ANALOGS

This application is a national stage entry of International Application No. PCT/US03/14633, filed May 9, 2003 and published as Pub. No. WO/2003/94850; and claims the benefit of priority of U.S. Provisional Application Ser. No. 60/378,645, filed May 9, 2002; all of which are hereby incorporated by reference in their entirety.

BACKGROUND OF THE INVENTION

1. Field of the Invention

The present invention relates to lipid A analogs characterized by the replacement of a sugar unit by a derivative of pentaerythritol. It also relates to analogs of carbohydrate ligands, including lipid A, characterized by the replacement of an amino sugar unit by a derivative of pentaerythritylamine.

2. Cross-Reference to Related Applications

Biomira (Jiang, et al.), PCT/US00/31281, filed Nov. 15, 2000 relates to the design and synthesis of some new Lipid-A analogs. The analogs were monophosphorylated, and contained either (1) at least one novel and unnatural lipid (such as lipids I or II) of compounds 33 and 102 (its FIG. 3), or (2) an unnatural combination of lipids. The latter refers to those Lipid-A analogs that carry lipids of uniform chain length. Its Compounds 54 and 86 (its FIG. 4) fall into this category. Its Compound 70 (its FIG. 19) is similar, but it also contains an n-propyl group at 3-O-position and is an example of Lipid-A analog that incorporates a short unnatural alkyl group with an unnatural ether linkage. By using a synthetic lipopeptide antigen, (FIG. 34), a modified 25-amino-acid sequence that is derived from tumor-associated MUC1 mucin, the applicants were able to evaluate the adjuvant properties of certain synthetic Lipid-A analogs disclosed in this invention. Based on the data of T-cell blastogenesis and IFN-γ level obtained through preliminary in vivo/in vitro studies, it was demonstrated that synthetic Lipid-A structures 48, 54, 70, 86, 102 and 104 are as effective, as adjuvants, as the Lipid-A preparations of bacterial origin.

Koganty, et al., U.S. Prov. Appl. No. 60/387,437, filed Jun. 11, 2002 relates to combinatorial peptide and glycopeptide libraries utilizing a pentaerythritol core.

Biomira (Koganty et al.), PCT/US03/10750, filed Apr. 9, 2003 teaches that a glycolipopeptide comprising at least one disease-associated epitope, and characterized by at least one lipidated interior amino acid or by the presence of a MUC1 epitope, may be used in a vaccine, preferably in conjunction with a liposome.

Biomira (Longenecker, et al.), PCT/US95/04540, filed Apr. 12, 1995, discloses that a conjugate of a primary epitope and an immunomodulatory peptide, or a mixture of a primary antigen and an immunomodulatory peptide, may be used to elicit an immune response which is CMI-specific.

Biomira (Jiang et al.), PCT/CA03/00135, filed Feb. 4, 2003, relates to the use of covalently lipidated oligonucleotides comprising the CpG dinucleotide unit, or an analogue thereof, as immunostimulatory agents. It discloses that a Pet structure can be used to link together such units.

The above-noted related applications are hereby incorporated by reference in their entirety.

2. Description of the Background Art

Pentaerythritol. Pentaerythritol (Pet) and di-pentaerythritol (di-Pet) are common polyols and they are widely used in oil industry to produce lubricants and other macromolecules. A derivative, tetrakis-[13-(2'-deoxythymidin-3'-O-yl)-6,9-diaza-2-oxa-5,10,13-trioxotridecyl)-methane (dT$_4$-PE-PLC) has been used as a liquid phase carrier for large-scale oligonucleotide synthesis in solution (Wörl, R. et al, 1999, compound 6). In addition, Pet derivatives, semifluorinated pentaerythritol tetrabenzoates, have been employed to design liquid crystalline structures (Cheng, X. H. et al, 2000) and pentaerythritol lipid derivatives (e.g., dimristoyl-trimethylglycine pentaerythritol) have been used in the preparation of cationic liposomes for the delivery of nucleic acids into mammalian cells (Nantz, M. H. et al, 2001). A triamine derivative of pentaerythritol has been used as a starting material in the preparation of chelating agents (Dunn, et al., 1990).

The four-directional core (the "Pet" unit) of pentaerythritol has been employed successfully as a coupling agent, for example, in the synthesis of multifunctional dendrimers (Armspach, D. et al, 1996 and Kuzdzal, S. A. et al, 1994), and as a molecular scaffold for combinatorial chemistry (Farcy, N. et al, 2001). Furthermore, Ranganathan et al used the Pet unit as a core to design a spiro-self-assembling cyclic peptide for constructing twin nanotubes (Ranganathan, D. et al, 2001).

It is particularly interesting to note the use of the Pet unit to couple sugar units. Lindhorst, et al, Eur. J. Org. Chem., 2027-34 (2000) used the Pet unit as a framework for a cluster of four mannosides. Schmidt, et al., Eur. J. Org. Chem., 669-674 (2002) prepared similar structures in which a lipid group (C16H33) was O-linked to one of the four peripheral carbons, and one to three mannoside residues were O-linked, through an ethyleneoxy oligomeric spacer, to other of the peripheral carbons. Those peripheral carbons which did not link to a lipid or to a sugar-containing moiety were simply hydroxylated. Finally, Hanessian et al. 1996 used a pentaerythritol scaffold to present a cluster of two Tn (the monosaccharide GalNAc) or TF (the disaccharide D-Galβ(1→3)GalNAc) epitopes, each O-linked through a spacer to a peripheral carbon of the Pet core. Of remaining two peripheral carbons, one was O-linked to —CH2CH2NHAc, and the other O-linked to either allyl (Hanessian 33) or 1-octenyl (Hanessian 37). In none of these references was a peripheral carbon of the Pet core N-linked to any moiety.

In the various applications mentioned above, the Pet unit serves as a core to carry other moieties. It may also be used to replace a sugar unit in an oligosaccharide. However, it has never before been used to replace a sugar unit in the lipid A disaccharide. Nor has Pet-NH— been used to replace an amino sugar in any carbohydrate ligand.

Toepfer et al disclosed sialyl-Lewis X and sialyl-Lewis A mimics containing one Pet unit (Toepfer et al. 1995; Toepfer et al. 2000) as new ligands for selectin binding. Thus, in compound 4 of Toepfer et al. 1995, two of the peripheral carbons of the Pet unit are hydroxylated, one is O-linked to a moiety comprising a single sugar unit, and the last one is O-linked to a moiety comprising a disaccharide. It should be noted that in Toepfer's analogs, the Pet unit replaces a normal sugar unit, not an amino sugar as in applicants' carbohydrate ligand analogs. In addition, the only lipophilic groups contemplated by Toepfer et al. are groups customarily used as protecting groups in organic synthesis, such as those resulting in replacement of sugar hydroxyls with —O-All, —O-Tf, or —O-Bn.

Aguilera et al. 1998 reported the testing of analogs of oligosaccharides for anti-mitotic activity. The original oligosaccharides were the tetrasaccharide α-D-GalNac-β-D-Gal-(1→4)-[α-L-Fuc-(1→3)]-β-D-GlcOMe, and a related sulfated trisaccharide (Aguilera compound 1), which contain a Lewis X-type structure. In the analogs of the trisaccharide (Aguilera compounds 13-16), one sugar was replaced with a Pet unit. In the analogs of the tetrasaccharide (17, 18), two of the sugar units were replaced with Pet units. The analogs thus contained the disaccharide in which the α-fucosyl residue was linked to the C-3 position of the GlcNac. In all six analogs, one hydroxyl of the disaccharide moiety was replaced with —O(CH$_2$)$_7$CH$_3$, thus imparting a lipid function. In analogs 14, 16 and 18, three of the four Pet unit peripheral carbons were hydroxylated (the remaining carbon being linked to a group comprising the disaccharide moiety). In Aguilera compounds 13, 15 and 17, two peripheral Pet carbons were hydroxylated and the third was sulfated. However, these compounds were found to be inactive as antimitotic agents in all of the cell types, thus discouraging further use of negatively charged groups in analogs of this family.

*Lipopolysaccharide* (bacterial). Lipopolysaccharide (LPS) is a unique glycolipid found exclusively in the outer leaflet of the outer membrane of Gram-negative bacteria. Structurally, bacterial LPS molecule has three main regions: the O-antigen region, the core region and the Lipid-A region (Stryer, 1981; Raetz, WO86/05687). The O-antigen region is a strain-specific polysaccharide moiety and determines the antigenic specificity of the organism. The core region is an oligosaccharide chain and may play a role in maintaining the integrity of the outer membrane. The Lipid-A region is conserved and functions as a hydrophobic anchor holding lipopolysaccharide in place.

LPS is known to trigger many pathophysiological events in mammals, either when it is injected or when is accumulated due to Gram-negative bacterial infection. Before the discovery of Lipid-A component of LPS the term "endotoxin" was generally used to describe the effects of the LPS. The endotoxin from Gram-negative bacteria is heat-stable, cell associated, pyrogenic and potentially lethal. In addition to its endotoxic activities, LPS also exhibits various biological activities, which include immuno adjuvant activity, B-lymphocyte mitogenesis, macrophage activation, interferon production, tumor regression, etc. While both the O-antigen and the core regions modulate the toxic activity of the LPS, it is generally believed that the hydrophobic Lipid-A moiety is responsible for these pathophysiological effects of the endotoxin (Rietschel, 1992: Takada, 1992).

*Lipid A and Its Synthetic Analogs.* Lipid A is the lipid anchor of lipopolysaccharide (LPS), the outer cell membrane component of Gram-negative bacteria. LPS is a strong activator of the innate immunity of the host following bacterial infection, and its lipid A moiety has been shown to be responsible for the biological activities of LPS in most in vitro and in vivo test systems. The structure-activity relationships of lipid A and its analogs have been extensively studied over the last two decades (Rietschel et al, 1996; Takada & Kotani, 1989).

Lipid-A consists of a β-(1,6)-linked D-glucosamine disaccharide phosphorylated at 1-O— and 4'-O-positions. Hydroxylated and non-hydroxylated fatty acids are linked to the hydroxyl and amino groups of the disaccharide to confer hydrophobicity to the Lipid-A. FIG. 1 of PCT/US00/31281 (Jiang3A-PCT) shows two examples of natural Lipid-A structures, compound A (Imoto, 1985a, b) isolated from *E. coli*, and compound B (Rietschel, 1984a, b; Seydel, 1981; Strain, 1985) isolated from *Salmonella* strains.

A large number of synthetic lipid A analogs have been prepared. For example, Lien et al. 2001 describe the agonist ER-112022, in which the disaccharide backbone of lipid A is replaced with —CH$_2$CH$_2$—NHCO—(CH$_2$)$_4$—CONH—CH$_2$CH$_2$—. The two phosphate groups link this substitute backbone to the lipid chains. Christ et al. 1995 prepared the lipid A antagonist E5531, derived by modification of the structure of the endotoxin-antagonistic *Rhodobacter capsulatus* lipid A, in which the naturally occurring acyl linkages at the C-3 and C-3' carbons were replaced with ether linkages, and the C-6' hydroxyl group was blocked. E5531 had advantages in stability and purity.

Takada and Kotani have conducted a thorough study of structural requirements of Lipid-A for endo-toxicity and other biological activities (Takada & Kotani, 1989), comparing synthetic Lipid-A analogs prepared by various groups (Kotani, 1986a, b; Kiso, 1986: Fujishima, 1987; Charon, 1985: Sato, 1995). They reported that for immunoadjuvant activity, the structural requirements of Lipid-A do not appear to be as rigid as those required for endotoxic activity and IFN-α/β or TNF-alpha inducing properties (Takada, 1989; Ribi, 1982). Removal of all fatty acids, however, abrogates all biological activities normally attributed to Lipid-A.

Ribi et al 1982 showed that the minimal structure required for toxicity was a bisphosphorylated β-(1,6)-linked di-glucosamine core to which long chain fatty acids are attached. It appears that an optimal number of lipid chains, in the form of either hydroxy acyl or acyloxyacyl groups, are required on the disaccharide backbone in order to exert strong endotoxic and related biological activities of Lipid-A (Kotani, 1986a).

In addition, removal of either phosphate group results in significant loss of toxicity without a corresponding loss of adjuvant activity. Bioassays on monophosphoryl Lipid-A showed that, while it was 1000 times less potent on a molar basis in eliciting toxic and pyrogenic responses, it was comparable to diphosphoryl Lipid-A (and endotoxin itself) in immunostimulating activities (Werner, 1996). It is known that the diphosphoryl Lipid-A from *E. coli* and *Salmonella* strains are highly toxic, but the monophosphoryl Lipid-A from *E. coli* has reduced toxicity while retaining the numerous biological activities that are normally associated with LPS (Werner, 1996; Takayama, 1984; Ulrich, 1995; Myerr, 1990).

Recently, it was suggested that the agonistic and antagonist activity of lipid A were governed by the intrinsic conformation of lipid A, which in turn was defined mainly by the number of charges, the number and distribution of acyl chains in the molecule (Seydel et al 2000; Schromm et al, 2000).

Furthermore, lipid A has been suggested to be a ligand for Toll-like receptor 4 (TLR4), a pattern-recognition receptor involved in the mediation of immune responses to LPS/lipid A (Kutuzova et al, 2001).

There is a need for effective treatment for Lipid-A/LPS associated disorders, and for a potent adjuvant without the associated toxicity. The high toxicity of unmodified Lipid-A from natural source discourages its general use as a pharmaceutical.

Another major drawback with the naturally derived Lipid-A is in accessing sufficient material with pharmaceutically acceptable purity, reproducible activity and stability. Naturally derived Lipid-A is a mixture of several components of cell wall including those of Lipid-A with varying number of lipid chains. Such heterogeneity in natural Lipid-A product is attributed to two sources: (1) biosynthetic variability in the assembly of the Lipid-A moiety and (2) loss of fatty acids from Lipid-A backbone during processing and purification. Consequently, it is difficult to control the manufacturing process in terms of reproducibility of composition of the mixture, which has significant bearing in biological activity and toxicity.

SUMMARY OF THE INVENTION

Lipid A Analogs

One object of the present invention is the design, synthesis and use of lipid A analogs in which one or both of the sugar units of the lipid A disaccharide is replaced with at least the carbon skeleton of pentaerythritol (the Pet core). These lipid A analogs may be characterized by additional differences from the natural product, e.g., changes in the number, structure and location of the lipid chains, elimination of one phosphate group, replacement of one or both phosphate groups with a related group (e.g., a sulfate group), and changes in the spacing or linkage of the sugar units (or their replacements).

The present invention also includes lipid A analogs in which one of the sugar units of the lipid A disaccharide is replaced with at least the carbon skeleton of pentaerythritol, and the other unit is omitted.

FIG. 3 shows a few examples of structural analogs of a lipid A disaccharide obtained by employing one or two Pet units.

In some embodiments, the lipid A analog is a derivative of pentaerythritamine (Pet-NH2), which is appropriate as lipid A comprises glucosamine, an amino sugar.

Lipid A analogs having lipid A agonistic activity (immunostimulatory activity) are useful as immunotherapeutic agents for the treatment of infections and cancers. As vaccine adjuvants, they can be formulated together with antigens to provide stronger immune responses to the administered antigens and thereby improve vaccine efficacy. They can also be used as stand-alone therapeutic agents (improving innate immunity). Naturally, they may be used in combination with other therapeutic agents for the treatment of targeted diseases.

Lipid A analogs having lipid A antagonistic activity may be used for the control of LPS-mediated pathophysiological disorders. Due to the exaggerated response to LPS released from Gram-negative bacteria, bacterial infection can sometimes lead to a cascade of pathophysiological events termed sepsis. Sepsis is deadly; it kills tens of thousands annually in the United States alone. Lipid A antagonists may bind to the LPS-binding receptor, Toll-like receptor 4 (TLR4), but such binding will not lead to the un-controlled release of inflammatory cytokines by the immune system. Therefore, these antagonists can be effective therapeutics to treat LPS-mediated disorders, such as inflammation and septic shock symptoms.

In the present invention, we have designed a class of lipid A analogs comprising a Pet core, and synthesized several specific examples (compound 1-4, FIG. 5).

Preliminary biological data show that lipid A mimics 1 and 2, which contain one PetNH$_2$ unit replacing the reducing end glucosamine of lipid A disaccharide, exhibit strong immunostimulatory activities (FIGS. 14 and 15). To further demonstrate the biological activity of the contemplated analogs, each of synthetic lipid A analogs 1 and 2 was incorporated into a liposomal formulation, together with a synthetic tumor-associated lipopeptide antigen derived from tumor-associated MUC1 glycoprotein. This vaccine formulation demonstrates obvious inhibition effect on tumor growth in mice (FIG. 16).

Thus, lipid A analogs, especially compounds 1 and 2, may be used as immunostimulatory adjuvants in treating diseases, as disclosed in this invention. In a preferred embodiment, they are used in liposomal constructs, which comprise totally synthetic immunostimulatory adjuvant(s) and totally synthetic antigen(s), for immunologically treating various diseases, such as infectious diseases and cancers.

Two other lipid A analogs, 3 and 4, have been synthesized. These contain derivatives of a di-pentaerythritol (di-Pet) and a di-pentaerythritamine (di-PetNH$_2$) unit, respectively, replacing the whole lipid A disaccharide backbone. The biological properties of compound 3 and 4 have not been evaluated.

Those analogs that possess lipid A antagonistic activity will be useful in treating lipopolysaccharide (LPS)—endotoxin—related disorders, such as septic shock.

Carbohydrate Hapten Analogs

Another object of the present invention is the design, synthesis and use of analogs of carbohydrate ligands. While a monosaccharide has several chiral centers, the Pet unit does not possess any chiral center due to its high symmetry. It is because of this non-chiral property that Pet can mimic various monosaccharides of different stereochemistry. Similarly, when one arm of the Pet is substituted with an amino group, the resulting pentaerythritamine (PetNH$_2$) unit can mimic various amino-substituted monosaccharides, including 1-amino-1-deoxy-(glycosylamine), 2-amino-2-deoxy-(glycosamine), 3-amino-3-deoxy-monosaccharide, etc. Therefore, structural mimics of almost all naturally occurring carbohydrate molecules can be produced by using a combination of natural monosaccharides and Pet unit(s), or Pet unit(s) alone.

While others have used the Pet unit to replace a sugar unit in a carbohydrate ligand, in every case the Pet unit employed was one retaining all of the hydroxyl oxygens, i.e., (Pet carbon core)(—O—)$_4$. The examples set forth below have demonstrated that derivatives (→Pet-NH—) of pentaerythritamine (PetNH$_2$) can readily mimic the reducing end glucosamine of lipid A disaccharide. Since lipid A is a carbohydrate ligand comprising an amino sugar, it is tempting to assume that PetNH$_2$ can be used to construct analogs of other carbohydrate ligands which comprise amino sugars, with →Pet-NH— replacing at least one of these amino sugars. For example →Pet-NH— can be used to replace N-acetyl-glucosamine and N-acetyl-galactosamine. Derivatives of the form (Pet carbon core) (—O—)$_3$—NH— are of particular interest.

FIG. 19 shows some PetNH$_2$-derived analogs of tumor-associated carbohydrate antigens, which are potentially useful for the development of immunotherapeutics to treat cancers. Similarly, FIG. 20 shows some PetNH$_2$-derived analogs of carbohydrate ligands involved in bacterial adhesion to host. Bacterial infection usually starts with the colonization of bacteria onto the host cells, during which process carbohydrate molecules are used as the binding ligands. Structural analogs of these carbohydrates are potential inhibitors for bacterial adhesion, and therefore can be effectively used as antibiotics to prevent bacterial infection. One advantage of such analogs over the naturally occurring carbohydrates is that the analogs are more resistant to enzymatic degradation in a biological system and therefore their bioavailability is improved.

The objects of the invention include remedying the deficiencies of the background art.

BRIEF DESCRIPTION OF THE DRAWINGS

FIG. 1 shows the structural similarities between a pentaerythritol (Pet) unit and a pentose and/or hexose.

FIG. 2 shows the general lipid A structures of lipopolysaccharides from Gram-negative bacteria. Lipid A consists of a beta-(1,6)-linked D-glucosamine disaccharide phosphorylated at 1-O— and 4'-O-positions, with numerous fatty acyl groups linked to the hydroxyl and amino groups of the disaccharide backbone. Structure A (Imoto et al, 1985) was isolated from *E. coli* and structure B (Seydel et al. 1984) was isolated from *Salmonella minnesota*.

FIG. 3 shows a few structures derived from Pet and di-Pet units to mimic the beta-1,6-diglucosamine disaccharide of lipid A. In structure I-IV, the glucosamine at the reducing end of lipid A disaccharide has been replaced by one Pet or PetNH$_2$ unit; in structure V-VI, the glucosamine unit at non-reducing end has been replaced by one Pet or PetNH2 unit;

and in structure VII-IX, the whole di-glucosamine disaccharide has been replaced by di-Pet, di-PetNH$_2$, or Pet-PetNH$_2$ unit. In structure III and IV, the non-reducing end glucosamine of lipid A disaccharide is also replaced by glucose. In order to demonstrate the rationale of the design, a few lipid A mimics (FIGS. 4 and 5) have been prepared based on structure I, VII and IX.

FIG. 4 shows examples of lipid structures that can be incorporated into lipid A molecules. Lipid A molecules carrying both naturally occurring lipids or un-natural lipids are well-tolerated by its binding receptor (Toll-like receptor 4) involved in immune stimulation. Lipid length is also variable, but most preferably in the range of 12 to 16 carbons. Those fatty acyl groups shown in FIG. 4 can be attached to both hydroxyl and amino groups of lipid A disaccharide backbone, while the alky group is preferably attached to a hydroxyl group through an ether linkage.

FIG. 5 shows four lipid A mimics (1-4) prepared as examples. Both 1 and 2 are designed as close structural mimics of natural lipid A (compound A or B, FIG. 2). Compound 2 retains both phosphoryl groups of natural lipid A while compound 1 represents 1-O-de-phosphorylated analog. In addition, the PetNH$_2$ unit in 1 retains its non-chiral property while the PetNH$_2$ in 2 becomes chiral, which ultimately results in the formation of a diastereomeric mixture of 2 if not separated. Structure 3 and 4 are derived from di-pentaerythritol (di-Pet) unit, carrying two phosphoryl groups but with fewer numbers of lipid chains.

FIG. 6 describes the synthesis of glycosylation donor 12 with benzyl protected phosphate group at 4-O-position. The coupling of 6 with lipid acid 7 afforded 8 in high yield. Selective opening of benzylidene ring in 8 using sodium cyanoborohydride and dry HCl (g) gave compound 9 in good yield. Benzyl protected phosphate group was then introduced into 4-O-position to form 10 in 86% yield. De-allylation followed by the reaction with trichloroacetonitrile and DBU provided the glycosylation donor 12.

FIG. 7 describes the synthesis of glycosylation acceptor 18, a Pet derivative. Benzyl substituted pentaerythritol 13 was prepared according to a literature procedure (Dunn et al, 1990). Dimethyl acetal formation from 13 gave the mono-hydroxyl compound 14, which was converted to its tosylate derivative 15. Reaction of 15 with sodium azide in the presence of phase transfer catalyst ALIQUAT™ provided azido-substituted intermediate 16, which was reduced to its free amine and then reacted with trichloroethoxycarbonyl chloroformate to give 17. The removal of the dimethyl acetal protecting group provided the di-hydroxyl compound 18 as a glycosylation acceptor for the preparation of designed lipid A mimic 1 and 2.

FIG. 8 describes the synthesis of intermediate 20. The glycosylation reaction of 12 with excess 18 (4.0 eq.) gave the desired mono-glycosylated product 19 in the presence of TMSOTf as catalyst in 81% yield. Treatment of 19 with zinc powder in acetic acid resulted in the removal of both Troc- group to give di-amine intermediate, which was then coupled with lipid acid 7 to provide intermediate 20. $^1$H NMR spectrum data of 20 showed two sets of doublet at d 4.35 (J=8.0 Hz) and d 4.65 (J=8.0 Hz), which confirmed the presence of two diastero-isomers in about 1:1 ratio, with both having b-linkage.

FIG. 9 shows the final preparation of the designed compound 1 and 2. Hydrogenolytic debenzylation of 20 in the presence of palladium on charcoal gave 1 in quantitative yield. On the other hand, the introduction of another benzyl-protected phosphate group into the free hydroxyl group of 20 provided 21, which was de-protected to afford the final product 2. The structure of both 1 and 2 were confirmed by $^1$H NMR and ESIMS spectra data.

FIG. 10 describes the synthesis of lipid A mimic 3. Di-pentaerythritol was first protected as di-benzylidene acetal 22 which was reacted with tetradecyl bromide in the presence of sodium hydride to give di-lipidated compound 23. Reductive ring opening of benzylidene acetals by treating 23 with sodium cyanoboronhydride and trifluoroacetic acid afforded 24 in moderate yield. Introduction of two benzyl-protected phosphate groups into 24 gave the precursor 25 which upon the treatment with palladium on charcoal under hydrogen atmosphere resulted in the designed product 3.

FIG. 11 describes the synthesis of the intermediate 29. Compound 22 was treated with tosyl chloride and pyridine to give the di-tosylate 26, which was converted to di-azide 27 by reacting with sodium azide in the presence of the phase catalyst Aliquat™ 336. Azide reduction with dithiopropane afforded the di-amine compound 28, which upon the coupling with di-lipo acid 7 provided the intermediate 29 in 66% yield.

FIG. 12 describes the synthesis of di-Pet derived lipid A mimic 4. Through the same reaction steps as described for the preparation of compound 3 (FIG. 10), compound 29 was converted to the target molecule 4 in overall good yield.

FIG. 13 shows some more structures designed as lipid A mimics (X-XII) containing PetNH$_2$ and di-PetNH$_2$. Structure X and XI are based on di-Pet skeleton with unsymmetrical lipid distribution. In structure XII, the PetNH$_2$ unit has replaced the non-reducing-end glucosamine of the lipid A disaccharide.

FIG. 14 exhibits the potency of lipid A mimic 1 and 2 in inducing the in vitro secretion of cytokines by adherent cells isolated from human peripheral blood. R595 lipid A, a natural lipid A product isolated from *Salmonella minnesota*, R595 (Avanti Polar Lipids, Inc.), was also tested along for comparison. The secretion pattern was determined for (a) secretion of tumor-necrosis factor-alpha (TNF-alpha, pg/mL); (b) secretion of IL-6 (pg/mL); (c) secretion of IL-8 (pg/mL). The data shows that lipid A mimic 1 and 2 are comparable to R595 lipid A in activation of secretion of all three cytokines, TNF-alpha, IL-6 and IL-8. It is quite reasonable to believe that mimic 1 and 2 activate these human monocytes by similar mechanism as their natural counterparts.

FIG. 15 shows the induction of antigen specific T cell proliferation response by synthetic liposomal vaccine BLP25 containing lipid A mimic 1 or 2 as an adjuvant. A MUC1 derived 25-mer lipopeptide, H$_2$N-STAPPAHGVTSAPDTR-PAPGSTAPPK(palmitoyl)G-OH, was used as the antigen. T cell proliferation data presented in FIG. 15 clearly demonstrates that C57BL/6 mice immunized with one dose of BLP25 liposomal vaccine produces a potent T cell response specific to MUC1 antigen. The response in the mice immunized with liposomal formulation containing synthetic lipid A mimic 1 or 2 is comparable to that in the group of mice immunized with formulation containing R595 lipid A. When the liposomal formulation contains no lipid A analog as an adjuvant, the antigen specific T cell proliferation response is very low (data not shown).

FIG. 16 shows the inhibitory effect on tumor growth of a liposomal vaccine containing a lipid A analog as an adjuvant. The liposomal vaccine BLP25 contains a MUC1 derived 25-mer lipopeptide and lipid A mimic 1 or 2, or R595 lipid A. Active specific immunotherapy of MC-38 MUC1 tumor bearing mice was performed by immunizing intradermally with BLP25 liposomal formulation. Mice were challenged with tumor on day 0 and immunized on day 7, 14 and 21. On day 34, tumor diameters (length & width) were taken and tumor size was expressed as mm$^2$ (length width). As presented in FIG. 16, BLP25 liposomal vaccine adjuvanted with synthetic lipid A mimic 1 or 2 produces tumor inhibition effect comparable to that produced by BLP25 formulation adjuvanted with R595 lipid A. In the control group of mice immunized with saline alone, tumor size is about the double of those immunized with BLP25 vaccine adjuvanted with lipid A mimic 1 or 2.

FIG. 17 shows a synthetic strategy for preparing one PetNH$_2$-containing carbohydrate mimic, TM. TM is based on the terminal tetrasaccharide of the tumor-associated Globo-H antigen in which the N-acetyl-galactosamine is replaced by PetNHAc. One arm of the PetNH$_2$-core is linked to the reducing-end galactose through an ether linkage while another arm is linked to the disaccharide through a glycosidic bond. Different methodologies are employed to construct this two different types of bonds. The ether bond may be constructed by classical S$_N$1/S$_N$2 substitution reaction while the glycosidic bond can be constructed through glycosylation reactions by using various kinds of glycosylation donor (e.g. trichloroacetimidate method as shown in FIG. 17). Standard protecting group manipulation, step-wide coupling, and final deprotection would result in the fully deprotected product TM.

FIG. 18 shows the structure of BLP25 lipopeptide (SEQ ID NO:1) derived from MUC1 mucin. The lipopeptide is a synthetic tumor-associated antigen used for the biological evaluation of lipid A mimic 1 and 2. A liposomal formulation containing BLP25 lipopeptide and either lipid A mimic 1 or 2 shows therapeutic effect in inhibiting tumor growth in mice.

FIG. 19 shows some examples of PetNH$_2$-containing new structures derived from tumor-associated carbohydrate antigens. These carbohydrates are associated with cancer progression and are expressed at higher level on cancer cells than on normal cells. Great efforts have been made to develop potential therapeutic agents for cancer treatment from these carbohydrates. (S. J. Danishefsky & J. R. Allen, *Angew. Chem. Int. Ed.* 2000, 39, 836-863). Structural mimetics are expected to exert similar immunological significance. Immune responses directed toward these mimetic structures are deemed to recognize their natural counterparts. For example, antibodies raised against the mimetic structure (TM, FIG. 17) of the Globo-H terminal tetrasaccharide is expected to cross-react with the cancer cells expressing Globo-H antigen.

FIG. 20 shows some new structures derived from those carbohydrates involved in the event of bacterial adhesion onto host cells. Glycosphingolipids (e.g., GM1, GM2, and GM3) and Lewis series carbohydrates (e.g., Le$^a$, Le$^b$, Le$^x$, Le$^y$, sialyl Le$^x$, etc.) are well known to play important roles in bacterial colonization onto host cells. It is general believed that molecules that inhibit this colonization process can be effective anti-bacterial agents in that they prevent the entry of bacteria to the host. Carbohydrate ligands in its natural form are poor inhibitors due to their low binding constants and their instability toward enzymatic degradation. Thus, synthetic mimetics of these natural carbohydrate ligands offer an opportunity to improve their low binding constant and low bioavailability in the biological system. For example, H type I blood determinant trisaccharide (FIG. 20) is implicated in adhesion involving the pathogenic bacteria *Helicobacter pylori*. Its structural mimetic provides an alternative skeleton where further chemical modifications can be maneuvered in order to find new molecules with higher inhibition efficiency.

DETAILED DESCRIPTION OF THE PREFERRED EMBODIMENTS OF THE INVENTION

For the sake of clarity, it should be noted that when the abbreviation "Pet" is used in the context of a structural component of the lipid A analogs of the present invention, what is intended is the "residue" of pentaerythritol, i.e., pentaerythritol less one or more of its hydrogens, so that it can be incorporated into a larger chemical entity. Moreover, the term "Pet", when used in this context, includes the disclosed modified moieties which retain the Pet five carbon core (2,2-dimethylpropane), but in which one or more of the hydroxyl oxygens is replaced with a spacer moiety Y1-Y4 as defined below.

Likewise, when the abbreviation "Pet-NH2" is used in the context of a structural component of the carbohydrate ligand analogs (including lipid A analogs) of the present invention, what is intended is the "residue" of pentaerythritamine, i.e., the latter less one of the amino hydrogens, and optionally less one or more of the hydroxyl hydrogens. Moreover, the term "Pet-NH2", when used in this context, includes the disclosed modified moieties in which one or more of the hydroxyl oxygens are replaced with a spacer moiety Y1-Y4 as defined below. The symbol →Pet-NH— is sometimes used to indicate that the amino function must be present, but that the other functions are subject to modification.

It should further be evident that the term "Pet" includes "Pet-NH2" as a special case, i.e., one in which one hydroxyl oxygen is replaced by nitrogen. If it is necessary to refer specifically to the situation in which none of the Pet carbons is aminated, one may use "Pet-OH" or "Pet-chal", the "chal" denoting chalcogen.

Lipid A Analogs

Bacterial Lipid-A compositions are widely used as adjuvants to enhance the immune responses to various antigens used in vaccine formulations.

The present invention relates to novel synthetic structural analogs of bacterial Lipid-A, especially *E. coli* lipid A, and methods of synthesis of such analogs. These lipid A analogs may be agonists or antagonists of bacterial lipid A. Agonists are likely to have a higher degree of structural similarity to lipid A than are antagonists.

Synthetic Lipid-A analogs have several advantages over naturally derived adjuvant preparations. A synthetic compound is chemically defined with single structure and thus facilitates its tracking and control from manufacturing to final formulation. Synthetic product is cost effective and is easily adaptable for commercial scale-up while maintaining the consistency in both quality and performance.

An invariant structural feature of the natural *E. coli* Lipid-A molecule is its β-(1,6)-linked D-glucosamine disaccharide backbone. However, it has been shown that monosaccharide analogs can express endotoxic activities. See, e.g., Matsuura, et al., Infect. & Immun. 63: 1446-51 (1995); Funatogawa, et al., Infect. & Immun., 66: 5792-98 (1998). Moreover, lipid A agonists are known in which the entire disaccharide unit has been replaced with an acyclic backbone, see Hawkins, J. Pharmacol. Exp. Therap. 300: 655-61 (2002).

The Lipid A analogs of the present invention replace at least one of the sugar units of natural Lipid A with the five carbon backbone (core) of pentaerythritol (Pet). This features a central carbon, singly bonded to four peripheral carbons:

These carbons are, in turn, be joined to other moieties.

The remaining sugar unit may be retained (possibly in a modified form), likewise replaced with Pet, or omitted altogether.

Thus, the lipid A analogs of the present invention have the structure

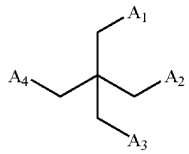

(Formula G-1)

where A1-A4 are hereafter defined. Each of A1-A4 may be considered a "primary branch" of the analog. Note that none of A1-A4 are merely hydrogen.

Since conservation of the sugar units is not considered important, one or both sugar units of lipid A may be replaced in the analog by a Pet unit, or one may be so replaced and the other omitted without replacement.

In general, to preserve structural similarity to lipid A, the following further limitations apply to A1-A4:

(1) at least one of A1-A4 comprises at least one phosphate equivalent (a phosphate group, or an analog thereof as described below), and (2) at least one of A1-A4 comprises at least one strongly lipophilic group as defined below.

With regard to limitation (1), natural lipid A is diphosphorylated, but it is known that the monophosphorylated analog is active, and applicants believe that certain phosphate analogs will also be efficacious.

With regard to limitation (2), natural lipid A is, plainly, lipidated, and if delipidated loses its immunostimulatory activity.

In a preferred embodiment, $A_1$ is $Y_1R_1$, $A_2$ is $Y_2R_2$, $A_3$ is $Y_3R_3$ and $A_4$ is $Y_4R_4$, where $Y_1$-$Y_4$ are spacers as hereafter defined. Preferably, each of $R_1$-$R_4$ is, independently, selected from the group consisting of hydrogen, an organic group, or a group which in conjunction with the adjacent Y group forms a phosphate, sulfate or borate. To put it another way, preferably each of R1-R4 is independently selected from the group consisting of hydrogen, —P(═O)(OH)OH, —C(═O)OH, —S(═O)(═O)OH, —B(OH)OH, or an organic group. Preferably, each of these organic groups has not more than 200 atoms other than hydrogen, more preferably, not more than 150, still more preferably, not more than 100.

The Pet unit may be considered to be the Pet backbone (core) as defined above, together with the $Y_1$-$Y_4$ groups which correspond to or replace the hydroxyl oxygens of unmodified Pet:

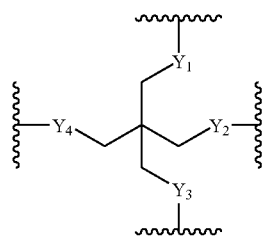

It is further noted that there may be more Pet units in the analog than those used to replace one or both sugar units of lipid A. Such "extra" Pet units may be useful as scaffolds for the attachment of phosphate-equivalents, strongly lipophilic groups, and other useful chemical moieties. Preferably, there are not more than two "extra" Pet units (i.e., a total of three Pet units if the analog includes a sugar unit, or a total of four Pet units if it doesn't). More preferably, there is just one, and most preferably, there is no "extra" Pet unit.

When there are two or more Pet units in an analog, they may be adjacent, or separated by another moiety. If they are adjacent, then one of the spacers Y1-Y4 of one Pet unit serves also as one of the spacers Y1-Y4 of the adjacent Pet unit, as seen, for example, in FIG. 3, compounds VII-IX, and FIG. 5, compounds 3 and 4.

Alternatively, there may be another chemical moiety connecting the spacer of one Pet unit and the spacer of the other Pet unit. This moiety may, but need not, comprise a sugar unit, a strongly lipophilic group, and/or a phosphate equivalent.

When there are more than two Pet units in an analog, they may be connected linearly (Pet1 . . . Pet2 . . . Pet3), cyclically (Pet1 . . . Pet2 . . . Pet3 . . . Pet1), or in a branched form (Pet1 . . . Pet2( . . . Pet3) . . . Pet4), or in some combination thereof. Note that in the above, " . . . " denotes a connection that may be adjacent or through some other chemical moiety.

In a preferred embodiment, if the lipid A analog comprises a sugar unit, the lipid analog is one such that if prepared as a thin multilayer film as described by Seydel et al., Eur. J. Biochem. 267: 3032-39 (2000), the tilt angle of the sugar backbone of the analog relative to the "membrane" surface, determined as taught by Seydel, is at least 35°, more preferably over 50°, if an agonist is sought, and the tilt angle is less than 25° if an antagonist is desired. It must be emphasized that this is merely a preferred embodiment and it is not necessary that the tilt angle be determined, or, if determined, that it be in the ranges suggested above.

Primary Arms

The numbering of the primary arms A1-A4 and their components Y1-Y4 and R1-R4 is completely arbitrary.

One approach to classifying the analogs is one the basis of whether they provide one sugar unit, a second Pet core, or neither.

Another approach to classification is on the basis of the number of the R groups R1-R4 which are H.

In a first class of analogs, R1-R3 are H, and R4 comprises the strongly lipophilic group(s), the phosphate equivalent, and, optionally, the sugar unit or second Pet core. In this class, it is preferable that either all of A1-A3 be —OH, or that two be —OH and the third —NH2. In R4, the component proximal to the Pet core may be the strongly lipophilic group, the phosphate equivalent, or, if present, the sugar unit or second Pet core. Preferably, R4 includes a sugar or second Pet core, and more preferably this is the component proximal to the first Pet core, and the phosphate equivalent and at least one strongly lipophilic group are connected to it.

In a second class of analogs, just two of the R1-R4 are H (and preferably the corresponding Y groups are —O—), and therefore the strongly lipophilic group, the phosphate equivalent, and optionally, the sugar unit or second Pet core, are distributed among the remaining two arms. Thus, in compound 1, one arm consists of an NH linked strongly lipophilic group, and a second consists of an O-linked phosphated and lipidated sugar unit.

In a third class of analogs, just one of the R1-R4 is H (and preferably the corresponding Y group is —O—), and the strongly lipophilic group(s), the phosphate equivalent(s), and, optionally, the sugar unit or second Pet core, are distributed among the remaining three arms.

Thus, in compound 2, one arm is phosphate (note that one of the phosphate oxygens does double duty as the Y group), a second arm is an NH-linked strongly lipophilic group, and the final arm is an O-linked sugar which is both lipidated (through —NH—) and phosphated. Compound 4 is similar, except that it is a second Pet core, rather than a sugar unit, which is lipidated and phosphated. Compound 3 differs from 4 in that the lipid is O- rather than NH-linked to the Pet cores.

In a fourth class of analogs, none of R1-R4 is H. Since at most one arm can comprise a sugar unit or a second Pet core, this implies that the other three arms comprise phosphate equivalents and/or strongly lipophilic groups. And that in turn implies that there must be at least two phosphate equivalents or at least two strongly lipophilic groups.

A third approach to classification is on the basis of the number and location of the phosphate equivalents. The classes are then (1) one phosphate equivalent, (2) two phosphate equivalents, but on the same arm, (3) two phosphate equivalents, on different arms, or (3) more than two phosphate equivalents. We may further subdivide them on the basis of whether phosphate equivalent is connected to a sugar unit or not.

A fourth approach to classification is on the basis of the number and location of the strongly lipophilic groups. For example, in compounds 1 and 2 there are three strongly lipophilic groups, and in compounds 3 and 4 there are two. Also, they may be connected to the Pet core (through a Y spacer), to a sugar unit, or to a phosphate equivalent.

Connection of Major Elements

In this specification, four major elements of the lipid A analog are defined: a Pet unit, a sugar unit, a strongly lipophilic group, and a phosphate equivalent. When it is said that two major elements are connected, it means without any other major element intervening. There may be some other chemical moiety, such as the disclosed linkers and spacers, in-between them.

Thus, when it is said that a strongly lipophilic group is connected to a phosphate equivalent, it means, without any intervening sugar unit or Pet unit. Likewise, when it is said that a strongly lipophilic group is connected to a sugar unit, it means, without any intervening Pet unit or phosphate equivalent. Conversely, when it is said that a strongly lipophilic group is connected to a Pet unit, it means, without any intervening sugar unit or phosphate equivalent. Analogous examples can be given for the other possible two-way connections of four kinds of major elements.

The specification may also identify two elements as being linked by a third element, in which case each of the former elements are connected to the latter.

Spacers (Y1-Y4)

Pentaerythritol can be considered to be the compound of general formula I in which A1-A4 are all —OH. Equivalently, it is the compound of that formula in which Y1-Y4 are all —O— and R1-R4 are all —H.

While pentaerythritol per se is not one of the lipid A analogs of the present invention, the latter does contemplate the incorporation of spacers Y1-Y4 which are —O— or analogs thereof.

In a preferred embodiment, each of spacers Y1-Y4 is independently selected from the group consisting of —(CH$_2$)$_n$O—, —(CH$_2$)$_n$S—, and —(CH$_2$)$_n$NH—, where n is, independently, 0 to 4. More preferably, each of these spacers is —O—, —S— or —NH— (i.e., n is 0). Even more preferably, each of these spacers is —O— or —NH—. Most preferably, either (a) all of these spacers are —O—, or (b) one spacer is —NH— and the other spacers are —O—.

Phosphate Equivalents in Lipid A Analogs

Natural Lipid A features two phosphate groups, each attached to a sugar unit (Lipid A being a disaccharide). However, it has been shown that monophosphoryl lipid A (MPLA) has adjuvanting activity and is less toxic than the natural diphosphorylated molecule. Also, we believe that one or more of the phosphate group(s) of lipid A and MPLA can be replaced by certain related chemical moieties.

Hence, in the lipid A analogs of the present invention, at least one of A1, A2, A3 and A4 comprises at least one —O—P(=O)(OH)—O—, —C(=O)OH, —O—S(=O)$_2$—O—, or —O—B(OH)—O— moiety, these being listed in order from most to least preferred. A phosphate analog is here defined as such a moiety, other than phosphate itself. A phosphate equivalent is here defined to include both phosphate and the phosphate analogs.

Preferably, if the lipid A analog lacks any sugar unit, at least one phosphate equivalent comprises a —O—P(=O)(OH)—O—, —O—S(=O)$_2$—O—, or —O—B(OH)—O— moiety.

The three aforementioned structures can be used to link the Pet core to a chemical moiety comprising at least one strongly lipophilic group, and/or a sugar equivalent selected from the group consisting of a sugar unit and a second Pet core. In such instance, one of the —O—'s of the phosphate equivalent is deemed the spacer Y1-Y4 referred to elsewhere.

Alternatively, the phosphate equivalent can be essentially a terminal moiety (the —C(=O)OH always is). Thus, in some preferred embodiments, at least one phosphate equivalent is of the form —OB(OH)OR, —OP(=O)(OH)OR or —OS(=O)(OH)OR, where R is hydrogen, or a substituted or unsubstituted alkyl group of 1-4 carbons. If R is hydrogen, then three of these moieties reduce to inorganic moieties: borate, phosphate and sulfate. If R is a substituted group, then the substitutions are preferably —OH or —NH2. An R group of particular interest is CH$_2$CH$_2$NH$_2$. Another structure of interest is —OP(=O)(OH)—O—P(=O)(—OH)—O—R, disclosed by Ulmer.

In other preferred embodiments, at least one phosphate equivalent is of the form —R'—C(O)OH, where R' is a substituted or unsubstituted alkyl group of 1-4 carbons. More preferably, R' is —CH$_2$—.

The lipid A analogs of the present invention preferably have one or two phosphate equivalents, and if they have more than one, they may be the same or different. Thus, they could have one phosphate and one phosphate analog. If there is more than one, the phosphate equivalents may be incorporated into the same or, more preferably, different primary branches of the analog.

In some preferred embodiments, at least one of A1-A4 will be the phosphate equivalent. In that case, one of the oxygens of the phosphate equivalents also serves as the Y1-Y4 spacer for that arm.

In other preferred embodiments, the phosphate equivalent will be a substituent of a larger moiety which connects to the aforementioned spacer. In an especially preferred sub-embodiment, this larger moiety is the aforementioned sugar or sugar analog, as, in natural lipid A, the phosphate group is attached to a sugar unit. In *E coli* lipid A, phosphate groups are attached to the C-1 and C-4' carbons of the core disaccharide.

In still other preferred embodiments, at least one phosphate equivalent is incorporated into at least one of the aforementioned lipophilic groups.

Optional Sugar Unit of Lipid A Analogs

It should be noted that natural lipid A is a disaccharide, and the required Pet unit of the analog replaces one of the two sugar units of that disaccharide. Hence, the lipid A analog will have either one or no sugar units. If it has no sugar units, it is because the second sugar unit of natural lipid A was replaced by a Pet core, or was omitted altogether.

If the analog includes a sugar, it need not be the same sugar as in native lipid A, i.e., a glucosamine. However, it is preferable that it be a hexose and/or a cyclic sugar (especially a pyranose), and more preferable that it be a glucose or glucose derivative, and still more preferable that it be a glucosamine.

If the analog comprises only one Pet unit, then preferably the phosphate equivalent is not —COOH, and preferably the analog does not comprise any nucleobase.

Lipid Complement of Lipid A Analogs

Lipid diversity contributes to by far the most significant variations among natural Lipid-A structures. While they are all linked through ester and amide bonds to the hydroxy and amino groups of the sugar respectively, variations include the number of lipids attached, the length of each lipid chain and the functional groups contained within the lipid chains. It is believed that these variations contribute to various biological functions of the entire Lipid-A molecule and more importantly to its adjuvant properties.

In some preferred embodiments, the lipid A analog comprises at least one strongly lipophilic group which is identical to a lipid chain occurring in a natural Lipid A structure. In a sub-embodiment, all of the strongly lipophilic groups of the lipid A analog are groups which occur in natural Lipid A structures, but it is not required that they all occur in the same natural lipid A molecule, or even in the contingent of lipids found in the natural lipid A molecules of the same bacterium. However, these further restrictions may be considered further sub-embodiments.

A major advantage provided by the synthesis of a Lipid-A analog is that a molecule may be designed to achieve effectiveness as an adjuvant, safety and stability by modifying lipid chains and their linkages.

Hence, in other preferred embodiments, the lipid A analog comprises at least one strongly lipophilic group which is not found in any natural Lipid A structure. The difference may be, but is not limited to, a difference in the length of the chain, the degree of branching of the chain, the presence or location of unsaturated linkages, or the presence or location of —COO— (ester), —O— (ether) or —NH— (amino) linkages.

Chemically speaking, ester linkages are labile as they are vulnerable to hydrolysis under physiological conditions. Gradual loss of lipid chains may slowly reduce the activity of the adjuvant under long storage of the vaccines thus diminishing their shelf life. Introduction of unnatural but stable ether linkages in place of esters may therefore be advantageous.

In the major form of natural *E. coli* lipid A, the discaccharide backbone is composed of two glucosamines, which we will call sugar II (it has a phosphate on the 4' carbon) and sugar I (it has a phosphate on the 1 carbon). The lipid component takes the form of six carbon chains, linked to the 2' and 3' carbons of sugar II and the 2 and 3 carbons of sugar I.

A branched lipid, is O-linked to the 3'-carbon. A similar branched lipid is N-linked to the 2' carbon. In both branched lipids, the primary chain (the one linked to the sugar ring carbon) is an acyl chain. A secondary acyl chain is O-linked to the C-3 carbon of the primary acyl chain (the carbonyl carbon being C-1). Thus, a total of four carbon (acyl) chains are linked directly or indirectly to sugar II.

Additionally, an unbranched but hydroxylated acyl chain is O-linked to the 3 carbon of the sugar ring and another such acyl chain is N-linked to the 2 carbon of the sugar ring. Thus, a total of two carbon (acyl) chains are linked to sugar I.

Since there are four acyl chains on one sugar, and two on the other, purified *E. coli* lipid A (Alexander, 2002, FIG. 2A; Se3ydel, 2000, FIG. 1A, "hexaacyl lipid A") is said to have an asymmetric hexaacyl lipid complement, and, more specifically, a 4/2 distribution. (All references to "lipid A" are, unless qualified, to this purified *E. coli* lipid A as described above.)

The lipid complement of the present Lipid A analogs consists essentially of one or more strongly lipophilic groups as defined in a later section. Each strongly lipophilic group preferably provides one or more major carbon chains as hereafter defined. Collectively, the lipid complement of the present lipid A analogs preferably provides one, two, three, four, five, six, seven, eight or more major carbon chains, with three to six being most preferred. Preferably, each strongly lipophilic group provides one, two or three major carbon chains. Preferably, these major carbon chains are each 10-20, more preferably 12-16 carbons.

In *E coli* lipid A, the lipid groups provide 82 carbon atoms, and in *S. minnesota* lipid A, 98 carbons (7 acyl chains), while in *R. capsulatus* lipid A, which is an endotoxin antagonist, they provide 60 carbon atoms. There are monosaccharide analog lipid A agonists whose lipid groups provide 42 carbon atoms.

Hence, preferably, the major carbon chains of the strongly lipophilic groups collectively provide at least 20, at least 30, at least 40, at least 50, at least 60, at least 70, or at least 80 carbon atoms. Desirably, they provide not more than 120, not more than 110, not more than 100, not more than 90, not more than 80, not more than 70 or not more than 60.

Preferably the sum of the predicted logPs (see belwo) for the strongly lipophilic groups is at least 10, at least 15, at least 20, at least 25, at least 30, at least 40, or at least 50. Preferably, it is not more than 60, not more than 40, not more than 40 or not more than 30.

Each strongly lipophilic group is preferably connected to the remainder of the analog by a proximal linker selected from the group consisting of —O—, —S—, and —NH—.

It may be so connected to the carbon of a sugar or Pet core, or to the sulfur, phosphorus or boron atom of a divalent phosphate equivalent. In the case of connection to a sugar, the proximal linker is the oxygen of a sugar hydroxyl, the sulfur of a thio sugar, or the nitrogen of an amino sugar. In the case of conncection to the Pet core, the proximal linker is a portion of the spacer Y1-Y4. In the case of connection to the aforementioned atom of a phosphate equivalent, the proximal linker is an —O— of said phosphate equivalent.

This proximal linker may be bonded directly to a major carbon chain as defined below, or to a distal linker. The distal linker may be divalent, trivalent, tetravalent, etc. Usually it will be at least trivalent, thus serving to connect the remainder of the analog to at least two different major carbon chains of the lipophilic group. The distal linker consists of two or more elements independently selected from the group consisting of alkyl of 1-5 carbon atoms, —O—, —S—, —C(=O)—, —C(=S)—, —NH—, and —N<, with the caveat that the atoms of the distal linker connected directly to the major carbon chains of the lipophilic group are not carbon atoms (if they were, then those atoms would be part of the carbon chain, not part of the distal linker).

In FIG. 4, the seventh and eighth structures feature distal linkers. In the seventh structure, it is the trivalent —C(=O)—CH(—CH$_2$—O—)—CH$_2$—O—. In the eighth structure, it is the trivalent —C(=O)—CH2-CH(—NH—)—C(=O)O—.

For the purpose of determining whether a group attached to a sugar is a strongly lipophilic group, the proximal linker is disregarded, but the distal linker is considered part of the group. Likewise, for a group attached to the Pet core, the intervening spacer is disregarded.

If the lipid A analog provides a sugar, at least one of the following sites on the sugar carbon skeleton may be linked to a strongly lipophilic group:

(A) the anomeric ring carbon (B) the other ring carbon immediately adjacent to the ring eteroatom (usually oxygen)

(C) a ring carbon other than those of (A) or (B) above (D) a sugar carbon other than a ring carbon.

It will be understood that such linkage will usually be through a linker such as the "proximal linker" defined herein, but a connection without a linker (i.e., a C-substituted amino acid) is not absolutely excluded.

If the sugar is a hexose and a pyranose, like glucose, at least one of the following sites may be linked to a strongly lipophilic group:

(1) the C-2 or C-2' carbon of the sugar rings (i.e., one of the sites at which natural lipid A is N-lipidated);

(2) the C-3 or C-3' carbon of the sugar rings (i.e., one of the sites at which natural lipid A is O-lipidated);

(3) the C-1' (anomeric) carbon of the sugar II ring (in natural lipid A, this carbon is linked to the C-6 of the sugar I, but if the sugar I is omitted, then this carbon is free);

(4) the C-1 (anomeric carbon) of the sugar I ring (in natural lipid A, this carbon is phosphorylated);

(5) the C-6 non-ring carbon of the sugar I (in natural lipid A, this carbon is linked to the C-1 of the sugar II, but if the sugar II is omitted, then this carbon is free);

(6) the C-6' non-ring carbon of the sugar II (in the lipid A disaccharide based on natural lipid A, this bears just —OH, but this is normally the site of attachment of the lipid A disaccharide to the remainder of the LPS molecule);

(7) the C-4' carbon of the sugar II ring (in natural lipid A, this is phosphated);

(8) the C-4 carbon of the sugar I ring (in natural lipid A, this bears a free hydroxyl).

Preferably, the strongly lipophilic groups are attached to the C-2 and C-3 of sugar I and the C-2' and C-3' of sugar II.

The use of a phosphate linker satisfies the requirement for a phosphate equivalent, but other phosphate equivalents may be provided, if desired. The use of a phosphate linker is preferred in the case of substitutions at the 4' ring carbon.

The —O— linker is preferred at the 4, 3 and 3' carbons, and the —NH— linker at the 2 and 2' carbons. It should be appreciated that if the NH2 group on these carbons is lipidated, the NH2 becomes an NH linker. Likewise, if the 4-OH is lipidated, the —OH becomes an —O— linker.

There is no particular preference with regard to the linker at the anomeric carbon or at the non-ring carbons of the sugar.

Alternatively or additionally, at least one lipophilic group may be incorporated into one or more of the primary arms of the Pet unit, without becoming a substituent of the sugar unit, if any. The primary arm in question may consist essentially of the strongly lipophilic group.

The strongly lipophilic group will in general comprise one or more carbon chains. Each carbon chain will be composed of carbon atoms linked sequentially by single, double or triple bonds.

Carbon chains which are at least six carbons in length are considered "major" carbon chains. Other carbon chain are considered "minor" carbon chains. The strongly lipophilic group preferably comprises at least one major carbon chain. There is no preference one way or another as to the presence of minor carbon chains.

Minor carbon chains can be considered a species of linker. In the seventh and eighth structures in FIG. 4, there are minor chains.

Preferably, no more than one bond of a particular carbon chain is a double or triple bond, and more preferably, the carbon chain is fully saturated. Double bonds are preferred over triple bonds.

The carbon atoms of a carbon chain may be bonded to 3, 2, 1 or 0 hydrogens. In a major carbon chain, the —CH< and >C< carbons are usually branching points for the attachment (with or without a linker) of another carbon chain. They may also be substituted with a side group, such as amino or hydroxyl.

Purely as a matter of definition, the strongly lipophilic group cannot comprise a Pet unit (it may comprise a Pet core if it lacks one or more of the required spacers Y1-Y4). However, what might otherwise have been interpreted as one large strongly lipophilic group comprising a Pet unit may be reinterpreted as a Pet unit with one or more smaller strongly lipophilic groups attached to it.

The carbon atoms of any major carbon chain may include one or more carbonyl or thiocarbonyl carbons, i.e., —C(=O)— or —C(=S)—. Carbonyl is preferred. If there is only one carbonyl or thiocarbonyl carbon, it is preferably at the beginning of the chain, so the chain is an acyl chain (saturated or unsaturated). Thus, if the linker is —O—, the attachment to carbonyl forms an ester (—O—(C=O)—), and if it is —NH—, the attachment forms an amide (—NH—(C=O)—.

A particular lipophilic group may be a simple (unbranched, acyclic) lipid, or a complex (branched and/or cyclic, including partially aromatic) lipid.

If the lipophilic group comprises more than one major carbon chain, the major chain beginning closest to the sugar or pet core is considered the primary major chain of the group. Any chains attached to the primary major chain are considered secondary major chains. Any major chains attached to the secondary major chains are considered tertiary major chains, etc. (Reference to primary, secondary, etc. chains hereafter is to major chains unless otherwise indicated.)

It is possible that several major chains will be equally close to the sugar or Pet core, in which case they will each be primary chains.

A secondary chain may be attached to the distal end (relative to the sugar or Pet core) of the primary chain, in which case the lipophilic group remains linear (absent other moieties). Or it may be attached to an interior carbon of the primary chain, in which case the lipophilic group is a branched lipid.

A secondary chain may be attached to a primary chain by a simple —O—, —S— or —NH— linker, or it may be attached directly without a linker (i.e., C—C). It also may be attached by a complex linker, i.e., a combination of a simple linker and the distal linker previously defined. A tertiary chain may be attached to a secondary chain in the same manner, and so on. A preferred point of attachment of a higher order chain to a lower order chain (e.g. secondary to primary) is at the C-3 carbon of the lower order (e.g., primary) chain.

Like a primary chain, a secondary or higher order chain may comprise doubly or triply bonded carbon atoms, and/or carbonyl or thiocarbonyl carbons.

The various carbon chains referred to above may be substituted with hydroxyl or amino groups, with hydroxyl being preferred. Preferred positions for the hydroxyl group would be as substituents on the C-2 or C-3 carbon of the chain.

The strongly lipophilic group may be entirely aliphatic or it may be partially aromatic in character. If it includes an aromatic structure, that structure is deemed a separate major carbon chain even if directly attached to an aliphatic chain. An entirely aliphatic group is preferred.

Fatty acid groups of the form —O—CO-Q, where Q is primarily alkyl but may include alkenyl, alkynyl, or ether linkages, are of particular interest. The fatty acids are carboxylic acids, often derived from or contained in an animal or vegetable fat or oil. All fatty acids are composed of a chain of hydrocarbon groups containing from 4 to 22 carbon atoms and characterized by a terminal carboxyl radical. They may be designated by "the number of carbon atoms: number of double bonds", and optionally the locations of cis/trans isomerism. Thus, suitable fatty acids include those with designations 4:0, 6:0, 8:0, 10:0, 12:0, 14:0, 16:0, 16:1 (9c), 18:0, 18:1 (9c), 18:2 (9c, 12c), 18:3 (9c, 12c, 15c), 18:4 (6c, 9c, 12c, 15c), 18:3 (9c, 11t, 13t), 18:1 (9c) 12-OH, 20:1 (9c), 20:1 (11c), 20:4 (8c, 11c, 14c, 17c), 20:5 (5c, 8c, 11c, 14c, 17c), 22:0, 22:1 (11c), 22:1 (13c), 22:5 (7c, 10c, 13c, 16c, 19c) and 22:6 (4c, 7c, 10c, 13c, 16c, 19c), all of which are found in naturally occurring glycosides.

The lipid structures which occur in natural lipid A from various species include 10:0, 12:0, 14:0, 16:0, 18:0, 20:0 fatty acids. Secondary acyl groups are usually 3-O-attached. Hydroxylation is usually 3-OH or 2-OH. A number of lipid As (e.g., *Rhodobacter capsulatus* and *Rhodobacter sphaeroides*) include 12:1 of 14:1 secondary acyl groups. See Alexander, et al., Trends in Glycoscience and Glycotechnology, 14: 69-86 (March 2002).

In a preferred embodiment, at least one strongly lipophilic group of the lipid A analog is a strongly lipophilic group not used as a protecting group in carbohydrate synthesis. Protecting groups used in carbohydrate synthesis include methyl, benzyl, allyl, trityl (triphenylmethyl), various acetates, benzoate, etc. Benzylidene and isopropylidene protecting groups may simultaneously protect two adjacent hydroxyl oxygens. See generally Harwood, *Modern Methods in Carbohydrate Synthesis* (1996); Dekker, *Preparative Carbohydrate Chemistry* (1997); Blackie, *Carbohydrate Chemistry* (1998).

The following generic structures are of interest:

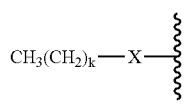

(i)

where X is —CO— or —CH$_2$—, k is an integer 4-30;

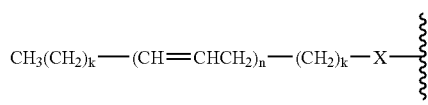

(ii)

where n is an integer 0-6, k is an integer 0-30 and 2k+3n is an integer 4-30;

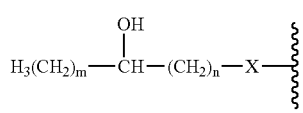

(iii)

where m and n are integers (0-6 for n and 0-30 for m), and m+n+1 is 4-30;

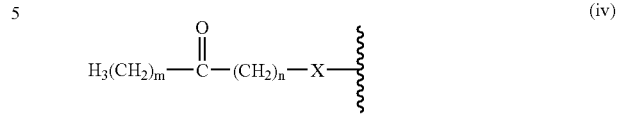

(iv)

where m+n+1 is 4-30;

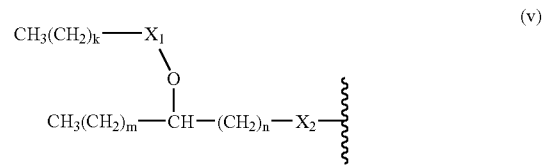

(v)

where X$_1$ and X$_2$ are independently —CO— or —CH$_2$—, and m+n+k+1 is 4-30;

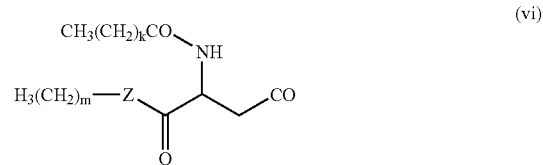

(vi)

where Z is —NH— or —O—, and k+m+2 is 4-30.

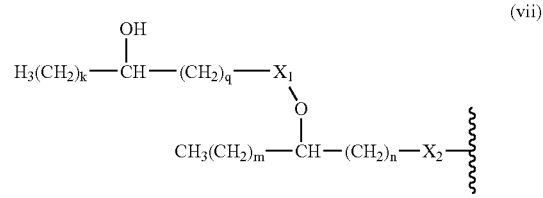

(vii)

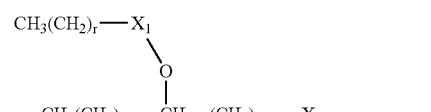

where q is an integer 0-6, and k+q+m+n is 4-30.

(viii)

where X$_1$, X$_2$, and X$_3$ are independently —CO— or —CH$_2$—, r is an integer 0-6, and r+k+q+m+n is 5-30.

In each of cases (i)-(viii), previously defined parameters retain their meaning.

See also the lipid A analog substituents suggested in U.S. Pat. No. 6,235,724.

It will be understood that these groups must still qualify as strongly lipophilic groups, which may further constrain the parameters indicated above.

The lipid structures depicted in our FIG. 4 are of particular interest. All of them qualify as strongly lipophilic groups.

Lipid Component of Other Carbohydrate Ligand Analogs

The lipid A analogs of the present invention are required to comprise at least one strongly lipophilic group. The carbohydrate ligand analogs of the present invention which are not lipid A analogs may, but need not, comprise a strongly lipophilic group. This can facilitate integration into a liposome. It should be noted that, for the purpose of determining whether an analog comprises a strongly lipophilic group, the required Pet core is disregarded.

Definition of Lipophilic and Strongly Lipophilic Groups

Groups may be classified as lipophilic (hydrophobic), lipophobic (hydrophilic), or neutral. The lipophilicity of groups may be determined by measuring the partition coefficient of the molecule HZ (where Z is the side chain in question) between a nonpolar solvent (e.g., ethanol, dioxane, acetone, benzene, n-octanol) and water, at STP. The lipophilicity may be defined as the logarithm of this partition coefficient; it will then be positive for molecules which prefer the nonpolar solvent. Thus, a lipophilic group is one for which logP is greater than zero.

The partition coefficient (P) is defined as the ratio of the equilibrium concentrations of a dissolved substance in a two-phase system consisting of two largely immiscible solvents. One such system is n-octanol:water; the octanol phase will contain about 20% water and the water phase about 0.008% octanol. Thus, the relevant partition coefficient (Pow) is the ratio of the molar concentration of the solute in octanol saturated with water to its molar concentration in water saturated with octanol. N-octanol is a useful surrogate for biological membranes because it, like many membrane components, is amphiphilic. (Reference hereafter to log P shall mean log Pow, unless otherwise stated.)

For more information on methods of determining Pow, see Sangster, J., *Octanol-Water Partition Coefficients: Fundamentals and Physical Chemistry* (April 1997) (ISBN 0-471-9739).

For tabulations of octanol-water partition coefficients, see the EPA "Chemicals in the Environment: OPPT Chemicals Fact Sheets" the USDA Pesticide Properties Database, Sangster, J., "Octanol-Water Partition Coefficients of Simple Organic Compounds", *J. Phys. Chem. Ref. Data*, 18:1111-1230 (1989); Verbruggen, E. M. J., et al., "Physiochemical Properties of Higher Nonaromatic Hydrocarbons: Literature Study," *J. Phys. Chem. Ref. Data*, 29:1435-46 (2000). For more sources, see references cited at Penn State University Libraries, Physical Sciences Library, octanol-water Partition Coefficients (last updated Aug. 21, 2001), at the URL libraries.psu.edu/crsweb/physci/coefficients.htm. It should be noted that the Pow values compiled for different compounds may have been determined by different methodologies.

To avoid the need for experimental determinations of log Pow, for the purpose of the present invention, the value predicted by Meylan's method will be used.

In Meylan's method, the predicted log Pow is obtained by adding weighted coefficients for each fragment (the raw coefficient multiplied by the number of copies of that fragment) to the constant 0.2290. The fragments considered include aliphatically attached —CH3 (0.5473), —CH2- (0.4911), —CH (0.3614), —OH (−1.4086), —NH2 (−1.4148), —C(=O)N (−0.5236), —SH (−0.0001), —NH— (−1.4962), N=C (−0.0010), —O— (−1.2566), —CHO (−0.9422), -tert C so 3+ attached (0.2676), C no H not tert (0.9723), —C(=O)O— (−0.9505), —C(=O)— (−1.5586), =CH or C< (0.3836), #C (0.1334), —C(=O)N (−0.5236), —O—CO—C—N—CO (−0.5), —SO—O (−9), —O—P (−0.0162); O=P (−2.4239), phosphate attached —OH (0.475); aromatic C (0.2940), aromatic N (5 membered ring) (−0.5262), and aromatically attached —OH (−0.4802)

The Meylan algorithm is implemented in the program LogPow (KowWin). An online version of the program, available at esc.syrres.com/interkow/kowdemo.htm accepts either CAS registry numbers or SMILES structure notations. The program also reports experimentally determined values, if in its database.

A group is expected to be a lipophilic group if its logP, as predicted by the Meylan algorithm, is greater than zero.

For the purpose of this disclosure, a strongly lipophilic group is defined as being a group, comprising at least five atoms other than hydrogen, for which the predicted log P is at least 3.

Preferably, the logP predicted by the Meylan algorithm is at at least 4, at least 5, at least 6, at least 7, at least 8, at least 9, or at least 10, the higher the more preferred.

Preferably, the strongly lipophilic group will comprise not more than 100 atoms other than hydrogen, more preferably, not more than 80 such atoms, still more preferably, not more than 60 such atoms, even more preferably not more than 40 such atoms.

As noted previously, the strongly lipophilic group must comprise at least five atoms other than hydrogen. Preferably, it comprises at least six, more preferably at least 8, still more preferably at least 9, even preferably, it comprises at least 11 such atoms, still more preferably at least 13 such atoms, most preferably at least 21 such atoms.

Preferably, the strongly lipophilic group has an elemental composition limited to the elements carbon, silicon, hydrogen, oxygen, nitrogen, sulfur, and phosphorous. Preferably, the majority of the bonds within the side chain which do not involve hydrogen are carbon-carbon bonds.

Since the presence of oxygen, nitrogen, sulfur and phosphorous tends to reduce lipophilicity, in the strongly lipophilic group, preferably more than 50%, still more preferably more than 75%, of the non-hydrogen atoms are carbon atoms.

For the same reason, the strongly lipophilic group preferably comprises at least 5, at least 6, at least 7, at least 8, at least 9, or at least 10 carbon atoms.

Application of Definition of Lipophilicity

Using the program LogKow, we have calculated (see below) low Pow values for the structures set forth in FIG. 4, or otherwise deemed worthy of comparison.

| SMILES (lower case is arom) | Comments | Pred LogP |
|---|---|---|
| CCCCC | alkyl (C5) | 2.80 |
| CCCCC C | alkyl (C6) | 3.29 |
| CCCCC CCCCC CCCCC CCCCC | alkyl (C20) | 10.16 |
| CCCC O CCCC | | 3.01 |
| CC(C) (C)C | Pet Core | 2.69 |
| FIG. 4 structures | | |
| CCCCC CCCCC CCCC | alkyl (C14) | 7.22 |
| O=C CCCCC CCCCC CCC | acyl (14:0) | 5.73 |
| CO CC(O) CCCCC CCCCC C | 14:0, 3-OH | 4.19 |
| O=C CC(=O) CCCCC CCCCC | | 3.68 |
| O=C CC(O C(=O)CCCCC CCCCC CCC) CCCCC CCCCC C | 14:0 3-O-(14:0) | 11.09 |
| O=C CC(O C(=O)CCCCC C=CCCC CCC) CCCCC CCCCC C | 14:0 3-O-(14:1) | 10.87 |

-continued

| SMILES (lower case is arom) | Comments | Pred LogP |
|---|---|---|
| O=C C(COC(=O)CCCCC CCCCC CCC) CO C(=O) CCCCC CCCCC CCC | | 11.61 |
| O=C CC(NC(=O)CCCCC CCCCC CCC) C(=O)O CCCCC CCCCC C | N-linked secondary acyl | 9.57 |
| O=C CC(OC(=O)CC(O CCCCC CCCCC CC) CCCCC CCCCC C)CCCCC CCCCC C | has O-linked tertiary acyl chain | 15.65 |

The predicted logP is used even if an experimental logP is available, e.g., for Pet core, it is 3.11.

Reference Carbohydrate Ligands; Carbohydrate Ligand Analogs

A reference carbohydrate ligand, for the purpose of the present invention, is a compound comprising one or more amino sugar units as hereafter defined, and which does not comprise a Pet core, which is capable of binding specifically to a receptor as a result, at least in part, of the presence of said sugar units. This reference ligand may, but need not, occur in nature.

The receptor may be a cellular receptor, or it may be an antibody. The antibody may, but need not, be naturally occurring, e.g., as part of the immune response to a disease. When the receptor is an antibody, the ligand may be considered an antigen. If it is able to elicit an immune response on its own, it is considered an immunogen. Otherwise, it is considered a hapten.

The reference carbohydrate ligand preferably has a specific binding activity for such receptor (desirably, with a binding affinity characterized by a $K_d$ less—i.e., better-than 10-3 liters/mole) and, more preferably, a biological or immunological activity attributable to such receptor binding.

Some reference carbohydrate ligands are set forth in the section "Carbohydrate Haptens" below, and others are in FIGS. 19 and 20.

In addition, one may consider antibiotics which contain carbohydrate, such as the pure sugar nojirimycin, the aminoglycosides streptomycin, kanamycin and gentamycin C, the N-glycoside streptothricin, the C-glycoside vancomycin, and the glycolipid moenomycin A.

It may also be an antitumor ligand, such as various sulfated oligosaccharides, in particular phosphomannopentaose sulfate (PI-88) and maltohexaose sulfate. See Parish, et al., Cancer Res., 59: 3433-41 (1999).

Or it may be an antiviral ligand, such as the azasugar 6-O-benzoyl castanospermine, an anti-Parkinson's disease agent, such as glycolipid ganglioside G, an anti-convulsant, such as topiramate, or a glycosidase inhibitor for diabetes therapy, such as an aza sugar, or an anti-thrombotic, such as the glycosylaminoglycan heparin.

The carbohydrate ligand analogs of the present invention are compounds which can compete with a reference carbohydrate ligand, as defined above, for binding to a receptor, and which differ from the reference carbohydrate ligand in that at least one amino sugar unit of the reference carbohydrate ligand is replaced with a (Pet core)-NH-moiety. They usually will be substantially identical to the reference carbohydrate ligand, disregarding such replacement.

The reference carbohydrate ligand may comprise sugar units which are not amino sugars. It may also comprise substantial non-carbohydrate moieties, such as, without limitation, lipids, sulfates, phosphates, amino acids, and nucleobases. It thus may be a glycolipid or glycopeptide.

A carbohydrate ligand analog may be considered substantially identical to the reference carbohydrate ligand if:

(1) for each sugar unit in the reference ligand, there is either a corresponding, substantially identical sugar unit or a corresponding Pet unit in the analog.

(2) The basic topology of the sugar units of the reference ligand is substantially identical to that of the corresponding sugar or Pet units in the analog.

One sugar unit is considered substantially identical to another if (1) they are both open or both cyclic, (2) if both cyclic, the ring sizes are the same and the ring heteroatoms are the same (usually oxygen), (3) if the configuration of a ring hydroxyl is constrained (axial or equatorial) in the reference ligand sugar, the hydroxyl is either retained in the analog sugar unit, or is replaced with halogen or with thiol, (4) if the constrained configuration hydroxyl is retained in the analog sugar unit, it is constrained the same way (axial or equatorial) in the analog sugar unit, (5) ring carbons which are aminated in the reference ligand sugar unit are aminated in the analog sugar unit, and no other ring carbons are aminated;

(6) the configuration (alpha or beta) of the anomeric carbon in the reference ligand sugar unit is retained in the analog sugar unit.

Permissible modifications include (1) replacement or deletion of substituents, other than hydroxyl, on ring carbons of the reference ligand sugar unit, (2) replacement or deletion of substituents on the ring carbons immediately adjacent to the ring heteroatom. Replacement can be with a larger chemical moiety than the original moiety.

By way of example, galactose, glucose and fucose are all hexoses (6 carbon sugar units), aldoses and pyranoses (with 6 membered rings; one oxygen, five carbon atoms). They differ in that Gal has an axial 4-OH, Glc has an equatorial 4-OH, and Fuc has an axial 4-OH but is missing a 6-OH, i.e., it is 6-deoxy-L-galactose. The carbons immediately adjacent to the ring oxygen are the C-1 and C-5 carbons. The C-1 substituent is OH, and the C-5 substituent is $CH_2OH$ in Gal and Glc, and $CH_3$ in Fuc.

These C-1 and C-5 substituents can be freely deleted or replaced, except that they cannot be aminated directly. The C-2, C-3 and C-4 atoms each bear configuration-constrained hydroxyls. These can be replaced only with thiol or halogen.

The replacement or deletion of substituents is further limited if the substituent of the ring carbon of the reference ligand sugar unit comprises another sugar unit. The substituent then cannot be deleted altogether, and it can be replaced only by a substituent which comprises a sugar unit or a Pet unit.

The basic topology is substantially identical if for each pair of sugar units which are linked directly in the reference ligand, the corresponding sugar units (or Pet units) must be linked directly in the analog. Linkages are considered direct if they do not comprise another sugar unit or Pet unit and if the most direct chain of atoms between the two units is not more than three times the length of the original linkage. It is not necessary that the chemical nature of the linkage be the same, e.g., a glycosidic linkage can be replaced by an ether linkage.

By way of example, in an analog of Lewis X, there is only one amino sugar (GlcNAc), so it is replaced with Pet-NH—.

There was also a Fuc alpha-O-linked 1→4 to the amino sugar, and a Gal beta-O-linked 1→3 to the same sugar. The analog would be Fuc alpha, linked through its C-1 carbon to a moiety comprising Pet, the latter being linked to the C-1 carbon of Gal beta. In both retained sugars, the C-5 substituent could be replaced or even eliminated (the sugars would then be pentoses rather than hexoses). Additionally, any of the C-2, C-3 and C-4 hydroxyls could be replaced with thiol or halogen.

It should be noted that the Lewis-X analogs would also be Lewis-a analogs.

Pharmaceutically Acceptable Salts

The ligand analogs of the present invention also include pharmaceutically acceptable salts of the disclosed compounds. Pharmaceutically acceptable salts include, but are not limited to, sodium, potassium, calcium and magnesium salts.

Carbohydrate

The term "carbohydrate" (sugar) includes monosaccharides, oligosaccharides and polysaccharides, as well as substances derived from the monosaccharides by reduction of the carbonyl group (alditols), by oxidation of one or more terminal groups to carboxylic acids, or by replacement of one or more hydroxy groups by a hydrogen atom, an amino group, a thiol group, or similar heteroatomic groups. It also include derivatives of the foregoing.

Monosaccharides

Parent monosaccharides are polyhydroxy aldehydes (H[CHOH]$_n$—CHO) or polyhydroxy ketones (H—[CHOH]$_n$—CO—[CHOH]$_m$—H) with three or more carbon atoms. The term "monosaccharide unit", "carbohydrate unit" or "sugar unit" refers to a residue of a monosaccharide, including the derivatives of monosaccharides contemplated herein.

Each monosaccharide unit is preferably a triose (e.g., glyceraldehyde), tetrose (e.g., erythrose, threose), pentose (e.g., ribose, arabinose, xylose, lyxose), hexose (e.g., allose, altrose, glucose, mannose, gulose, idose, galactose, talose), heptose, or octose. More preferably it is a pentose or hexose.

Each monosaccharide unit may be an aldose (having an aldehydic carbonyl or potential aldehydic carbonyl group) or a ketose (having a ketonic carbonyl or potential ketonic carbonyl group). (Fructose is an example of a ketose.) The monosaccharide unit further may have more than one carbonyl (or potential carbonyl) group, and hence may be a dialdose, diketose, or aldoketose. The term "potential aldehydic carbonyl group" refers to the hemiacetal group arising from ring closure, and the ketonic counterpart (the hemiketal structure).

The monosaccharide unit may be a cyclic hemiacetal or hemiketal. Cyclic forms with a three membered ring are oxiroses; with four, oxetoses, with five, furanoses; with six, pyranoses; with seven, septanoses, with eight, octaviruses, and so forth. The locants of the positions of ring closure may vary. Note that in the more common cyclic sugars, the ring consists of one ring oxygen, the remaining ring atoms being carbon; hence, in pyranose, there is one ring oxygen and five ring carbons.

The monosaccharide unit may further be a deoxy sugar (alcoholic hydroxy group replaced by hydrogen), amino sugar (alcoholic hydroxy group replaced by amino group), a thio sugar (alcoholic hydroxy group replaced by thiol, or C=O replaced by C=S, or a ring oxygen of cyclic form replaced by sulfur), a seleno sugar, a telluro sugar, an aza sugar (ring carbon replaced by nitrogen), an imino sugar (ring oxygen replaced by nitrogen), a phosphano sugar (ring oxygen replaced with phosphorus), a phospha sugar (ring carbon replaced with phosphorus), a C-substituted monosaccharide (hydrogen at a non-terminal carbon atom replaced with carbon), an unsaturated monosaccharide, an alditol (carbonyl group replaced with CHOH group), aldonic acid (aldehydic group replaced by carboxy group), a ketoaldonic acid, a uronic acid, an aldaric acid, and so forth. Amino sugars include glycosylamines, in which the hemiacetal hydroxy group is replaced.

Derivatives of these structures include O-substituted derivatives, in which the alcoholic hydroxy hydrogen is replaced by something else. Possible replacements include alkyl, acyl, phosphate, phosphonate, phosphinate, and sulfate. Likewise, derivatives of amino sugars include N-substituted derivatives, and derivatives of thio sugars include S-substituted derivatives.

Sialic acid, also known as N-acetyl neuraminic acid (NANA), is of particular interest. It is the terminal sugar on several tumor-associated carbohydrate epitopes.

Combinations

Any of the carbohydrate ligand analogs of the present invention may be used in combination with each other, with other carbohydrate ligands (including, but not limited to, the reference carbohydrate ligands and to other analogs thereof), and other pharmaceutical agents. When the ligand analog is used as an immunological agent, it may be used in combination with other immunological agents. Immunological agents include antigens (including both immunogens and haptens), adjuvants, and other immodulatory molecules (including cytokines).

Any of the lipid A analogs of the present invention may be used in combination with each other, with other lipid A analogs, with natural lipid A molecules, and other pharmaceutical agents. The latter may be immunological agents.

A combination may be a covalent conjugate, a noncovalent conjugate, a simple mixture, or use such that all of the elements of the combination are simultaneously active in the subject to which they are administered. Simultaneous activity may, but need not, be achieved by simultaneous administration. Compounds may be simultaneously active even if they are not simultaneously administered, e.g, compound A with a long half-life is administered prior to compound B with a short half-life, but A is still present in the body at an effective level when B is administered.

Immunogen

The immunogen of the present invention is a molecule, comprising at least one disease-associated B or T cell epitope, as defined below, and which, when suitably administered to a subject (which, in some cases, may mean associated with a liposome or with an antigen-presenting cell), elicits a humoral and/or cellular immune response which is protective against the disease.

The present invention contemplates (1) the use of the disclosed lipid A analogs to stimulate innate immunity, (2) the use of the disclosed lipid A analogs to adjuvant the specific immune response to an administered immunogen, and (3) the use of an immunogen comprising at least one of disclosed carbohydrate ligand analogs to elicit a specific immune response, with or without the use of the disclosed lipid A/Pet analogs as adjuvants. (In case (3), the carbohydrate ligand analog comprises a disease-associated carbohydrate epitope as hereafter defined.)

If the epitope is a carbohydrate epitope, it may be an analog of a naturally occurring epitope containing at least one amino sugar, in which at least one amino sugar is replaced with an aminated Pet unit.

Epitope

The epitopes of the present invention may be B-cell or T-cell epitopes, and they may be of any chemical nature, including without limitation peptides, carbohydrates, lipids, glycopeptides and glycolipids. The epitope may be identical to a naturally occurring epitope, or a modified form of a naturally occurring epitope.

A term such as "MUC1 epitope", without further qualification, is intended to encompass, not only a native epitope of MUC1, but also a mutant epitope which is substantially identical to a native epitope. Such a mutant epitope must be cross-reactive with a native MUC1 epitope. Likewise, a term such as "tumor-associated epitope" includes both native and mutant epitopes, but the mutant epitope must be cross-reactive with a native tumor-associated epitope.

B-Cell Epitopes

B-cell epitopes are epitopes recognized by B-cells and by antibodies. B-cell peptide epitopes are typically at least five amino acids, more often at least six amino acids, still more often at least seven or eight amino acids in length, and may be continuous ("linear") or discontinuous ("conformational") (the latter being formed by the folding of a protein to bring noncontiguous parts of the primary amino acid sequence into physical proximity). B-cell epitopes may also be carbohydrate epitopes.

T-Cell Epitopes

The T cell epitope, if any, may be any T cell epitope which is at least substantially the same as a T-cell epitope of an antigen including a hapten) which is associated with a disease or adverse condition to a degree such that it could be prophylactically or therapeutically useful to stimulate or enhance a cellular immune response to that epitope. Such diseases and conditions include, but are not limited to parasitic diseases such as schistosomiasis and leishmania, fungal infections such as candidiasis, bacterial infections such as leprosy, viral infections such as HIV infections, and cancers, especially solid tumors. Of course, the greater the degree of specificity of the epitope for the associated disease or adverse condition, the more likely it is that the stimulation of an immune response to that epitope will be free of adverse effects.

The epitope must, of course, be one amenable to recognition by T-cell receptors so that a cellular immune response can occur. For peptides, the T-cell epitopes may interact with class I or class II MHC molecules. The class I epitopes usually 8 to 15, more often 9-11 amino acids in length. The class II epitopes are usually 5-24 (a 24 mer is the longest peptide which can fit in the Class II groove), more often 8-24 amino acids. If the immunogen is larger than these sizes, it will be processed by the immune system into fragments of a size more suitable for interaction with MHC class I or II molecules.

The carbohydrate T-cell epitopes may be as small as a single sugar unit (e.g., Tn). They are preferably no larger than five sugars.

Many T-cell epitopes are known. Several techniques of identifying additional T-cell epitopes are recognized by the art. In general, these involve preparing a molecule which potentially provides a T-cell epitope and characterizing the immune response to that molecule. Methods of characterizing the immune response are discussed in a later section.

The reference to a CTL epitope as being "restricted" by a particular allele of MHC Class I molecules, such as HLA-A1, indicates that such epitope is bound and presented by the allelic form in question. It does not mean that said epitope might not also be bound and presented by a different allelic form of MHC, such as HLA-A2, HLA-A3, HLA-B7, or HLA-B44.

Disease-Associated and Disease-Specific Epitopes

A disease is an adverse clinical condition caused by infection or parasitization by a virus, unicellular organism, or multicellular organism, or by the development or proliferation of cancer (tumor) cells.

The unicellular organism may be any unicellular pathogen or parasite, including a bacteria, fungus or protozoan. The multicellular organism may be any pathogen or parasite, including a protozoan, worm, or arthropod. Multicellular organisms include both endoparasites and ectoparasites. Endoparasites are more likely to elicit an immune response, but, to the extent they can elicit a protective immune response, ectoparasites and their antigens are within the purview of the present invention.

An epitope may be said to be directly associated with a viral disease if it is presented by a virus particle, or if it is encoded by the viral genome and expressed in an infected cell.

An epitope may be said to be directly associated with a disease caused by a unicellular or multicellular organism if it presented by an intracellular, surface, or secreted antigen of the causative organism.

An epitope may be said to be directly associated with a particular tumor if it is presented by an intracellular, surface or secreted antigen of said tumor. It need not be presented by all cell lines of the tumor type in question, or by all cells of a particular tumor, or throughout the entire life of the tumor. It need not be specific to the tumor in question. An epitope may be said to be "tumor associated" in general if it is so associated with any tumor (cancer, neoplasm).

Tumors may be of mesenchymal or epithelial origin. Cancers include cancers of the colon, rectum, cervix, breast, lung, stomach, uterus, skin, mouth, tung, lips, larynx, kidney, bladder, prostate, brain, and blood cells.

An epitope may be indirectly associated with a disease if the epitope is of an antigen which is specifically produced or overproduced by infected cells of the subject, or which is specifically produced or overproduced by other cells of the subject in specific, but non-immunological, response to the disease, e.g., an angiogenic factor which is overexpressed by nearby cells as a result of regulatory substances secreted by a tumor.

The term "disease associated epitope" also includes any non-naturally occurring epitope which is sufficiently similar to an epitope naturally associated with the disease in question so that antibodies or T cells which recognize the natural disease epitope also recognize the similar non-natural epitope. Similar comments apply to epitopes associated with particular diseases or classes of diseases.

An epitope may be said to be specific to a particular source (such as a disease-causing organism, or, more particular, a tumor), if it is associated more frequently with that source than with other sources, to a detectable and clinically useful extent. Absolute specificity is not required, provided that a useful prophylactic, therapeutic or diagnostic effect is still obtained.

In the case of a "specific tumor-specific" epitope, the epitope is more frequently associated with that tumor that with other tumors, or with normal cells. Preferably, there should be a statistically significant (p=0.05) difference between its frequency of occurrence in association with the tumor in question, and its frequency of occurrence in association with (a) normal cells of the type from which the tumor is derived, and (b) at least one other type of tumor. An epitope may be said to be "tumor-specific" in general is it is associated more frequently with tumors (of any or all types) than with normal cells. It need not be associated with all tumors.

The term "tumor specific epitope" also includes any non-naturally occurring epitope which is sufficiently similar to a naturally occurring epitope specific to the tumor in question (or as appropriate, specific to tumors in general) so that antibodies or T cells stimulated by the similar epitope will be essentially as specific as CTLs stimulated by the natural epitope.

In general, tumor-versus-normal specificity is more important than tumor-versus-tumor specificity as (depending on the route of administration and the particular normal tissue affected), higher specificity generally leads to fewer adverse effects. Tumor-versus-tumor specificity is more important in diagnostic as opposed to therapeutic uses.

The term "specific" is not intended to connote absolute specificity, merely a clinically useful difference in probability of occurrence in association with a pathogen or tumor rather than in a matched normal subject.

In one embodiment, the epitope is a parasite-associated epitope, such as an epitope associated with leishmania, malaria, trypanosomiasis, babesiosis, or schistosomiasis. In another embodiment, the epitope is a viral epitope, such as an epitope associated with human immunodeficiency virus (HIV), Epstein-Barr virus (EBV), or hepatitis.

The epitope may also be associated with a bacterial antigen, such as an antigen of the tuberculosis bacterium, *Staphylococcus, E. coli* or *Shigella sonnei*.

In another embodiment, the epitope is associated with a cancer (tumor), including but not limited to cancers of the respiratory system (lung, trachea, larynx), digestive system (mouth, throat, stomach, intestines) excretory system (kidney, bladder, colon, rectum), nervous system (brain), reproductive system (ovary, uterus, cervix), glandular system (breast, liver, pancreas, prostate), skin, etc. The two main groups of cancers are sarcomas, which are of mesenchymal origin and affect such tissues as bones end muscles, and carcinomas, which are of epithelial origin and make up the great majority of the glandular cancers of breasts, stomach, uterus, skin and tongue. The sarcomas include fibrosarcomas, lymphosarcomas, osteosarcomas, chondrosarcomas, rhabdosarcomas and liposarcomas. The carcinomas include adenocarcinomas, basal cell carcinomas and squamous carcinomas.

Cancer-associated epitopes include, but are not limited to, peptide epitopes such as those of mutant p53, the point mutated Ras oncogene gene product, her 2/neu, c/erb2, and the MUC1 core protein, and carbohydrate epitopes such as sialyl Tn (STn), TF, Tn, CA 125, sialyl Le$^x$, sialyl Le$^a$ and P97.

Identification of Natural Epitopes

Naturally occurring epitopes may be identified by a divide-and-test process. One starts with a protein known to be antigenic or immunogenic. One next tests fragments of the protein for immunological activity. These fragments may be obtained by treatment of the protein with a proteolytic agent, or, if the peptide sequence is known, one may synthetically prepare smaller peptides corresponding to subsequences of the protein. The tested fragments may span the entire protein sequence, or just a portion thereof, and they may be abutting, overlapping, or separated.

If any of the fragments are immunologically active, the active fragments may themselves be subjected to a divide-and-test analysis, and the process may be continued until the minimal length immunologically active sequences are identified. This approach may be used to identify either B-cell or T-cell epitopes, although the assays will of course be different. Geysen teaches systematically screening all possible oligopeptide (pref. 6-10 a.a.) abutting or overlapping fragments of a particular protein for immunological activity in order to identify linear epitopes. See WO 84/03564.

It is also possible to predict the location of B-cell or T-cell peptide epitopes if an amino acid sequence is available. B-cell epitopes tend to be in regions of high local average hydrophilicity. See Hopp and Wood, Proc. Nat. Acad. Sci. (USA) 78: 3824 (1981); Jameson and Wolf, CABIOS, 4: 181 (1988). T-cell epitopes can be predicted on the basis of known consensus sequences for the peptides bound to MHC class I molecules of cells of a particular haplotype. See e.g., Slingluff, WO98/33810, especially pp. 15-16; Parker, et al., "Scheme for ranking potential HLA-A2 binding peptides based on independent binding of individual peptide side chains", J. Immunol. 152: 163 (1994).

Naturally occurring T-cell epitopes may be recovered by dissociating them from their complexes with MHC class I molecules and then sequencing them, e.g., by mass spectroscopic techniques.

Generally speaking, in addition to epitopes which are identical to the naturally occurring disease- or tumor-specific epitopes, the present invention embraces epitopes which are different from but substantially identical with such epitopes, and therefore disease- or tumor-specific in their own right. It also includes epitopes which are not substantial identical to a naturally occurring epitope, but which are nonetheless cross-reactive with the latter as a result of a similarity in 3D conformation.

Peptide Epitopes

A peptide epitope is considered substantially identical to a reference peptide epitope (e.g., a naturally occurring epitope) if it has at least 10% of an immunological activity of the reference epitope and differs from the reference epitope by no more than one non-conservative substitution.

Carbohydrate Haptens; Epitopes

The carbohydrate hapten of the present invention is a carbohydrate which comprises (and preferably is identical to) a carbohydrate epitope, but which does not elicit a humoral immune response by itself.

Normally, a carbohydrate hapten will not be a polysaccharide, as a polysaccharide is usually large enough to be immunogenic in its own right. The borderline between an oligosaccharide and a polysaccharide is not fixed, however, we will define an oligosaccharide as consisting of 2 to 20 monosaccharide (sugar) units.

The hapten may be a monosaccharide (without glyosidic connection to another such unit) or an oligosaccharide. If an oligosaccharide, it preferably is not more than 10 sugar units.

Tumor associated carbohydrate epitopes are of particular interest.

A variety of carbohydrates can be conjugated according to the present invention, for use particularly in detecting and treating tumors. The Tn, T, sialyl Tn and sialyl (2→6)T haptens are particularly preferred.

In particular, for detecting and treating tumors, the three types of tumor-associated carbohydrate epitopes which are highly expressed in common human cancers are conjugated to aminated compounds. These particularly include the lacto series type 1 and type 2 chain, cancer associated ganglio chains, and neutral glycosphingolipids.

Examples of the lacto series Type 1 and Type 2 chains are as follows: Lewis a, dimeric Lewis a, Lewis b, Lewis b/Lewis a, Lewis x, Lewis, y, Lewis a/Lewis x, dimeric Lewis x, Lewis y/Lewis x, trifucosyl Lewis y, trifucosyl Lewis b, sialosyl Lewis x, sialosyl Lewis y, sialosyl dimeric Lewis x, Tn, sialosyl Tn, sialosyl TF, TF. Examples of cancer-associated ganglio chains are as follows: GM3. GD3, GM2, GM4, GD2, GM1, GD-1a, GD-1b. Neutral sphingolipids include globotriose, globotetraose, globopentaose, isoglobotriose, isoglobotetraose, mucotriose, mucotetraose, lactotriose, lactotetraose, neolactotetraose, gangliotriose, gangliotetraose, galabiose, and 9-O-acetyl-GD3.

Numerous antigens of clinical significance bear carbohydrate determinants. One group of such antigens comprises the tumor-associated mucins (Roussel, et al., *Biochimie* 70, 1471, 1988).

Generally, mucins are glycoproteins found in saliva, gastric juices, etc., that form viscous solutions and act as lubricants or protectants on external and internal surfaces of the body. Mucins are typically of high molecular weight (often >1,000,000 Dalton) and extensively glycosyiated. The glycan chains of mucins are O-linked (to serine or threonine residues) and may amount to more than 80% of the molecular mass of the glycoprotein. Mucins are produced by ductal epithelial cells and by tumors of the same origin, and may be secreted, or cell-bound as integral membrane proteins (Burchell, et al., *Cancer Res.*, 47, 5476, 1987; Jerome, et al., *Cancer Res.*, 51, 2908, 1991).

Cancerous tissues produce aberrant mucins which are known to be relatively less glycosylated than their normal counter parts (Hull, et al., *Cancer Commun.*, 1, 261, 1989). Due to functional alterations of the protein glycosylation machinery in cancer cells, tumor-associated mucins typically contain short, incomplete glycans. Thus, while the normal mucin associated with human milk fat globules consists primarily of the tetrasaccharide glycan, gal β1-4 glcNAcp1-6 (gal β1-3) gal NAc-α and its sialylated analogs (Hull, et al.), the tumor-associated Tn hapten consists only of the monosaccharide residue, α-2-acetamido-3-deoxy-D-galactopyranosyl, and the T-hapten of the disaccharide β-D-galactopyranosyl-(1-3)α-acetamido-2-deoxy-D-galactopyranosyl. Other haptens of tumor-associated mucins, such as the sialyl-Tn and the sialyl-(2-6)T haptens, arise from the attachment of terminal sialyl residues to the short Tn and T glycans (Hanisch, et al., *Biol. Chem. Hoppe-Seyler,* 370, 21, 1989; Hakormori, *Adv. Cancer Res.*, 52:257, 1989; Torben, et al., *Int. J. Cancer,* 45 666, 1980; Samuel, et al., *Cancer Res.*, 50, 4801, 1990).

The T and Tn antigens (Springer, *Science*, 224, 1198, 1984) are found in immunoreactive form on the external surface membranes of most primary carcinoma cells and their metastases (>90% of all human carcinomas). As cancer markers, T and Tn permit early immunohistochemical detection and prognostication of the invasiveness of some carcinomas (Springer). Recently, the presence of the sialyl-Tn hapten on tumor tissue has been identified as an unfavorable prognostic parameter (Itzkowitz, et al. *Cancer,* 66, 1960, 1990; Yonezawa, et al., *Am. J. Clin. Pathol.*, 98 167, 1992). Three different types of tumor-associated carbohydrate antigens are highly expressed in common human cancers. The T and Tn haptens are included in the lacto series type, and type 2 chains. Additionally, cancer-associated ganglio chains and glycosphingolipids are expressed on a variety of human cancers.

The altered glycan determinants displayed by the cancer associated mucins are recognized as non-self or foreign by the patient's immune system (Springer). Indeed, in most patients, a strong autoimmune response to the T hapten is observed. These responses can readily be measured, and they permit the detection of carcinomas with greater sensitivity and specificity, earlier than has previously been possible. Finally, the extent of expression of T and Tn often correlates with the degree of differentiation of carcinomas. (Springer).

An extensive discussion of carbohydrate haptens appears in Wong, U.S. Pat. No. 6,013,779. A variety of carbohydrates can be incorporated into a synthetic glycolipopeptide immunogen, according to the present invention, for use particularly in detecting and treating tumors. The Tn, T, sialyl Tn and sialyl (2→6)T haptens are particularly preferred. In particular, for detecting and treating tumors, the three types of tumor-associated carbohydrate epitopes which are highly expressed in common human cancers are conjugated to aminated compounds. These particularly include the lacto series type 1 and type 2 chain, cancer associated ganglio chains, and neutral glycosphingolipids.

Examples of the lacto series. Type 1 and Type 2 chains are as follows:

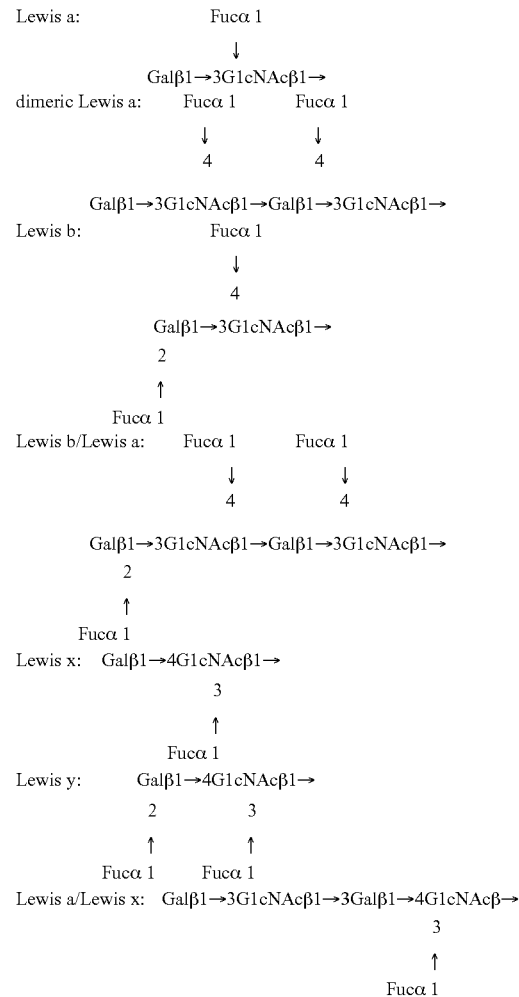

-continued

Lewis y/Lewis x:

Galβ1→4GlcNAcβ1→3Galβ1→4GlcNAcβ
    2            3             3
    ↑           ↑            ↑
Fucα1    Fucα1    Fucα1

Trifucosyl Lewis y:

Galβ1→4GlcNAcβ1→3Galβ1→4GlcNAcβ→3Galβ1→4Glcβ1→
    2            3             3
    ↑           ↑            ↑
Fucα1    Fucα1    Fucα1

Trifucosyl Lewis b:

Fucα1
↓
Galβ1→3GlcNAcβ1→3Galβ1→4GlcNAcβ1→3Galβ1→4Glcβ1→
    2            3             3
    ↑           ↑
Fucα1    Fucα1

Sialosyl Le$^x$:

NeuAcα2→3Galβ1→4GlcNacβ1→
                           3
                           ↑
                      Fucα1

Sialosyl Le$^a$:

Fucα1
↓
4
NeuAcα2→3Galβ1→3GlcNacβ1→

Sialosyl Dimeric Le$^x$:

NeuAcα2→3Galβ1→4GlcNacβ1→3Galβ1→4GlcNAcβ1→
                       3                 3
                       ↑                 ↑
                 Fucα1           Fucα1

Tn:    GalNAcα1→

Sialosyl-Tn:    NeuAcα→6GalNAcα1→

Sialosyl-T:    NeuAcα→6(Galβ1-3)GalNAcα1→

NeuAcα→6GalNAcα1→
           3
           ↓
          Galβ1

T:    Galβ1→3GalNAcα1→

Examples of cancer-associated ganglio chains that can be conjugated to aminated compounds according to the present invention are as follows:

CANCER ASSOCIATED GANGLIO CHAINS

GM3:    NeuAcα2→3Galβ1→4Glcβ1→
GD3:    NeuAcα2→8NeuAcα2→3Galβ1→4Glcβ1→
GM2:    GalNAcβ1→4Galβ1→4Glcβ1→
                        3
                        ↓
                  NeuAcα2

-continued

GM4:    NeuAcα2→3Galβ1→
GD2:    GalNAcβ1→4Galβ1→4Glcβ1→
                     3
                     ↓
          NeuAcα2→8NeuAcα2
GM1:    Galβ1→3GalNAcβ1→4Galβ1→4Glcβ1→
                           3
                           ↑
                   NeuAcα2
GD-1a:    NeuAcα2→3Galβ1→3GalNAcβ1→4Galβ1→4Glcβ1→
                                     3
                                   ↑
                          NeuAcα2
GD-1b:    Galβ1→3GalNAcβ1→4Galβ1→4Glcβ1→
                         3
                       ↑
          NeuAcα2→8NeuAcα2

In addition to the above, neutral glycosphingolipids can also be conjugated to aminated compounds according to the present invention:

Selected Neutral Glycosphingolipids

Globotriose: Galα→4Galβ1→4Glcβ1→

Globotetraose: GalNAcβ1→3Galα→4Galβ1→4Glcβ1→

Globopentaose:
GalNAcα1→3GalNAcβ1→3Galα→4Galβ1→4Glcβ1→

Isoglobotriose: Galα→3Galβ1→4Glcβ1→

Isoglobotetraose:
GalNAcβ1→3Galα1→3Galα1→4Glcβ1→

Mucotriose: Galβ1→4Galβ1→4Glcβ1→

Mucotetraose: Galβ1→3Galβ1→4Galβ1→4Glcβ1→

Lactotriose: GalNAcβ1→3Galβ1→4Glcβ1→

Lactotetraose:
GalNAcβ1→3GalNAcβ1→3Galβ1→4Glcβ1→

Neolactotetraose:
Galβ1→4GlcNAcβ1→3Galβ1→4Glcβ1→

Gangliotriose: GalNAcβ1→4Galβ1→4Glcβ1→

Gangliotetraose: Galβ1→GlcNAcβ1→4Galβ1→4Glcβ1→

Galabiose: Galα→4Galβ1→

9-O-Acetyl-GD3:    9-O—Ac-NeuAcα2→8NeuAcα2→3Galβ1→4Glcβ1→

Immunoconjugates

The immunogen of the present invention may be an immunoconjugate in which one or more epitopes are joined with other chemical moieties to create a molecule with different immunological properties, such as increased ability to elicit a humoral immune response. For example, one or more epitopes may be conjugated to a macromolecular carrier, such as albumin, keyhole limpet hemocyanin (KLH) or polydextran. Or several epitopes may be joined to a branched lysine core, such as a MAP-4 peptide. Or several epitopes may simply be conjugated together using some other linker or molecular scaffold.

Adjuvants

It is generally understood that a synthetic antigen of low molecular weight can be weakly immunogenic, which is the biggest obstacle to the success of a fully synthetic vaccine. One way to improve the imunogenicity of such a synthetic antigen is to deliver it in the environment of an adjuvant.

As conventionally known in the art, adjuvants are substances that act in conjunction with specific antigenic stimuli to enhance the specific response to the antigen. An ideal adjuvant is believed to non-specifically stimulate the immune system of the host, which upon the subsequent encounter of any foreign antigen can produce strong and specific immune response to that foreign antigen. Such strong and specific immune response, which is also characterized by its memory, can be produced only when T-lymphocytes (T-cells) of the host immune system are activated.

T-cell blastogenesis and IFN-gamma production are two important parameters for measuring the immune response. Experimentally, T-cell blastogenesis measures DNA synthesis that directly relates to T-cell proliferation, which in turn is the direct result of the T-cell activation. On the other hand, IFN-gamma is a major cytokine secreted by T-cells when they are activated. Therefore, both T-cell blastogenesis and IFN-gamma production indicate T-cell activation, which suggests the ability of an adjuvant in helping the host immune system to induce a strong and specific immune response to any protein-based antigen.

The compound is considered an adjuvant if it significantly ($p=0.05$) increases the level of either T-cell blastogenesis or of interferon gamma production in response to at least one liposome/immunogen combination relative to the level elicited by the immunogen alone. Preferably, it does both. Preferably, the increase is at least 10%, more preferably at least 50%, still more preferably, at least 100%.

Preferably, the toxicity of the lipid compounds of the present invention is not more than 50% that of said natural Lipid-A product; more preferably it is less than 10% that of the latter.

A large number of adjuvants are known in the art, including Freund's complete adjuvant, saponin, DETOX (Ribi Immunochemicals), Montanide ISA-51, -50 and -70, QS-21, monophosphoryl lipid A and analogs thereof. A lipid adjuvant can be presented in the context of a liposome.

The present liposomal vaccines may be formulated advantageously with an adjuvant. Monophosphoryl lipid A (MPLA), for example, is an effective adjuvant that causes increased presentation of liposomal antigen to specific T Lymphocytes. Alving, C. R., Immunobiol., 187:430-446, (1993). The skilled artisan will recognize that lipid-based adjuvants, such as Lipid A and derivatives thereof, are also suitable. A muramyl dipeptide (MDP), when incorporated into liposomes, has also been shown to increase adjuvanticity (Gupta R K et al., Adjuvants-A balance between toxicity and adjuvanticity," Vaccine, 11, 293-306 (1993)).

Use of an adjuvant is not required for immunization.

Liposome Formulations

Liposomes are microscopic vesicles that consist of one or more lipid bilayers surrounding aqueous compartments. See e.g., Bakker-Woudenberg et al., Eur. J. Clin. Microbiol. Infect. Dis. 12 (Suppl. 1): S61 (1993) and Kim, Drugs, 46: 618 (1993). Because liposomes can be formulated with bulk lipid molecules that are also found in natural cellular membranes, liposomes generally can be administered safely and are biodegradable.

Liposomes are globular particles formed by the physical self-assembly of polar lipids, which define the membrane organization in liposomes. Liposomes may be formed as unilamellar or multi-lamellar vesicles of various sizes. Such liposomes, though constituted of small molecules having no immunogenic properties of their own, behave like macromolecular particles and display strong immunogenic characteristics.

Depending on the method of preparation, liposomes may be unilamellar or multilamellar, and can vary in size with diameters ranging from about 0.02 microm to greater than about 10 microm. A variety of agents can be encapsulated in liposomes. Hydrophobic agents partition in the bilayers and hydrophilic agents partition within the inner aqueous space(s). See e.g., Machy et al., Liposomes in Cell Biology and Pharmacology (John Libbey, 1987), and Ostro et al., American J. Hosp. Pharm. 46: 1576 (1989).

Liposomes can adsorb to virtually any type of cell and then release an incorporated agent. Alternatively, the liposome can fuse with the target cell, whereby the contents of the liposome empty into the target cell. Alternatively, a liposome may be endocytosed by cells that are phagocytic. Endocytosis is followed by intralysosomal degradation of liposomal lipids and release of the encapsulated agents. Scherphof et al., Ann. N.Y. Acad. Sci., 446: 368 (1985).

Other suitable liposomes that are used in the methods of the invention include multilamellar vesicles (MLV), oligolamellar vesicles (OLV), unilamellar vesicles (UV), small unilamellar vesicles (SUV), medium-sized unilamellar vesicles (MUV), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubble-somes (BSV). The skilled artisan will recognize that the techniques for preparing these liposomes are well known in the art. See Colloidal Drug Delivery Systems, vol. 66 (J. Kreuter, ed., Marcel Dekker, Inc., 1994).

A "liposomal formulation" is an in vitro-created lipid vesicle in which a pharmaceutical agent, such as an antigen, of the present invention can be incorporated or to which one can be attached. Thus, "liposomally-bound" refers to an agent that is partially incorporated in or attached to a liposome. The immunogen of the present invention may be a liposomally-bound antigen which, but for said liposome, would not be an immunogen, or it may be immunogenic even in a liposome-free state. Several different agents may be incorporated into or attached to the same liposome, or different agents may be associated with different liposomes, and the liposomes administered separately or together to a subject.

A lipid-containing molecule can be incorporated into a liposome because the lipid portion will spontaneously integrate into the lipid bilayer. Thus, a lipid-containing agent may be presented on the "surface" of a liposome. Alternatively, an agent may be encapsulated within a liposome.

Formation of a liposome requires one or more lipids. Any lipids may be used which, singly or in combination, can form a liposome bilayer structure. Usually, these lipids will include at least one phospholipid. The phospholipids may be phospholipids from natural sources, modified natural phospholipids, semisynthetic phospholipids, fully synthetic phospholipids, or phospholipids (necessarily synthetic) with nonnatural head groups. The phospholipids of greatest interest are phosphatidyl cholines, phosphatidyl phosphatidyl ethanolamines, phosphatidyl serines, phosphatidyl glycerols, phosphatidic acids, and phosphatidyl inositols.

The liposome may include neutral, positively charged, and/or negatively charged lipids. Phosphatidyl choline is a neutral phospholipid. Phosphatidyl glycerol is a negatively charged glycolipid. N-[1-(2,3-dioleylox)propyl]-N,N,N-trimethylammonium chloride is a positively charged synthetic lipid. Another is 3-beta-[N—(N',N"-dimethylaminoethane)-carbamoyl]-cholesterol.

Usually, the lipids will comprise one or more fatty acid groups. These may be saturated or unsaturated, and vary in carbon number, usually from 12-24 carbons. The phospholipids of particular interest are those with the following fatty acids: C12:0, C14:0, C16:0, C18:0, C18:1, C18:2, C18:3 (alpha and gamma), C20:0, C20:1, C20:3, C20:4, C20:5, C22:0, C22:5, C22:6, and C24:0, where the first number refers to the total number of carbons in the fatty acids chain, and the second to the number of double bonds. Fatty acids from mammalian or plant sources all have even numbers of carbon atoms, and their unsaturations are spaced at three carbon intervals, each with an intervening methylene group.

Cholesterol reduces the permeability of "fluid-crystalline state" bilayers.

A liposome may include lipids with a special affinity for particular target cells. For example, lactosylceramide has a specific affinity for hepatocytes (and perhaps also for liver cancer cells).

In a preferred liposome formulation, the component lipids include phosphatidyl choline. More preferably they also include cholesterol, and still more preferably, also phosphatidyl glycerol. Taking advantage of the self-assembling properties of lipids, one or more immunogens may be attached to the polar lipids that in turn become part of the liposome particle. Each immunogen comprises one or more antigenic determinants (epitopes). These epitopes may be B-cell epitopes (recognized by antibodies) or T-cell epitopes (recognized by T-cells). The liposome can act to adjuvant the immune response elicited by the associated immunogens. It is likely to be more effective than an adjuvant that is simply mixed with an immunogen, as it will have a higher local effective concentration.

Moreover, a hapten may be attached in place of the aforementioned immunogen. Like an immunogen, a hapten comprises an antigenic determinant, but by definition is too small to elicit an immune response on its own (typically, haptens are smaller than 5,000 daltons). In this case, the lipid moiety may act, not only as an adjuvant, but also as an immunogenic carrier, the conjugate of the hapten and the lipid acting as a synthetic immunogen (that is, a substance against which humoral and/or cellular immune responses may be elicited).

Even if the lipid does not act as an immunogenic carrier, the liposome borne hapten may still act as a synthetic antigen (that is, a substance which is recognized by a component of the humoral or cellular immune system, such as an antibody or T-cell). The term "antigen" includes both haptens and immunogens.

Thus, in some embodiments, the invention contemplates a liposome whose membrane comprises a Lipid A analog as disclosed herein, and at least one B-cell or T-cell epitope. The epitope may be furnished by a lipopeptide, glycolipid or glycolipopeptide.

The lipidation of an immunogen normally will facilitate the incorporation of the immunogen into a liposome, which in turn can improve the immune presentation of the immunogen. For most efficient incorporation, at least one strongly lipophilic group of the immunogen preferably should be similar in size to at least one of the lipid components of the liposome. For example, the size should be in the range of 50%-200% of the size of the reference lipid component of the liposome. Size may be measured by counting the number of non-hydrogen atoms of each, by calculating the molecular weight of each, or by calculating (with the aid of 3D molecular models) the molecular volume or longest dimension of each.

Preferably, the lipidated immunogen comprises a lipophilic moiety which adjuvants the humoral or cellular immune response to the immunogen.

Unlike the bacterial adjuvant preparations, a synthetic Lipid-A analog contributes a structurally well-defined lipid to the liposome membrane. Such defined structures not only reduce the burden of re-affirming the 'active' membrane components after formulation, but also contribute to the definition of liposome membrane. Such liposomes may be designated as 'totally synthetic vaccine formulations' containing synthetic Lipid-A analog as an adjuvant and a synthetic lipid-containing antigen.

Characterizing the Immune Response

The cell-mediated immune response may be assayed in vitro or in vivo. The conventional in vitro assay is a T cell proliferation assay. A blood sample is taken from an individual who suffers from the disease of interest, associated with that disease, or from a vaccinated individual. The T cells of this individual should therefore be primed to respond to a new exposure to that antigen by proliferating. Proliferation requires thymidine because of its role in DNA replication.

Generally speaking, T cell proliferation is much more extensive than B cell proliferation, and it may be possible to detect a strong T cell response in even an unseparated cell population. However, purification of T cells is desirable to make it easier to detect a T cell response. Any method of purifying T cells which does not substantially adversely affect their antigen-specific proliferation may be employed. In our preferred procedure, whole lymphocyte populations would be first obtained via collection (from blood, the spleen, or lymph nodes) on isopycnic gradients at a specific density of 10.7, ie Ficoll-Hypague or Percoll gradient separations. This mixed population of cells could then be further purified to a T cell population through a number of means. The simplest separation is based on the binding of B cell and monocyte/macrophage populations to a nylon wool column. The T cell population passes through the nylon wool and a >90% pure T population can be obtained in a single passage. Other methods involve the use of specific antibodies to B cell and or monocyte antigens in the presence of complement proteins to lyse the non-T cell populations (negative selection). Still another method is a positive selection technique in which an anti-T cell antibody (CD3) is bound to a solid phase matrix (such as magnetic beads) thereby attaching the T cells and allowing them to be separated (e.g., magnetically) from the non-T cell population. These may be recovered from the matrix by mechanical or chemical disruption.

Once a purified T cell population is obtained it is cultured in the presence of irradiated antigen presenting cells (splenic macrophages, B cells, dendritic cells all present). (These cells are irradiated to prevent them from responding and incorporating tritiated thymidine). The viable T cells (100,000-400,000 per well in 100 µl media supplemented with IL2 at 20 units) are then incubated with test peptides or other antigens for a period of 3 to 7 days with test antigens at concentrations from 1 to 100 µg/mL.

At the end of the antigen stimulation period a response may be measured in several ways. First the cell free supernatants may be harvested and tested for the presence of specific cytokines. The presence of α-interferon, IL2 or IL12 are indicative of a Th helper type 1 population response. The presence of IL4, IL6 and IL10 are together indicative of a T helper type 2 immune response. Thus this method allows for the identification of the helper T cell subset.

A second method termed blastogenesis involves the adding tritiated thymidine to the culture (e.g., 1 μcurie per well) at the end of the antigen stimulation period, and allowing the cells to incorporate the radiolabelled metabolite for 4-16 hours prior to harvesting on a filter for scintillation counting. The level of radioactive thymidine incorporated is a measure of the T cell replication activities. Negative antigens or no antigen control wells are used to calculated the blastogenic response in terms of a stimulation index. This is CPM test/CPM control. Preferably the stimulation index achieved is at least 2, more preferably at least 3, still more preferably 5, most preferably at least 10.

CMI may also be assayed in vivo in a standard experimental animal, e.g., a mouse. The mouse is immunized with a priming antigen. After waiting for the T cells to respond, the mice are challenged by footpad injection of the test antigen. The DTH response (swelling of the test mice is compared with that of control mice injected with, e.g., saline solution.

Preferably, the response is at least 0.10 mm, more preferably at least 0.15 mm, still more preferably at least 0.20 mm, most preferably at least 0.30 mm.

The humoral immune response, in vivo, is measured by withdrawing blood from immunized mice and assaying the blood for the presence of antibodies which bind an antigen of interest.

For example, test antigens may be immobilized and incubated with the samples, thereby capturing the cognate antibodies, and the captured antibodies then measured by incubating the solid phase with labeled anti-isotypic antibodies.

Preferably, the humoral immune response, if desired, is at least as strong as that represented by an antibody titer of at least 1/100, more preferably at least 1/1000, still more preferably at least 1/10,000.

Lipid A Analogs as Immunostimulating Agents

Lipid A analogs which have LPS/lipid A agonistic activities can be used as immune stimulatory agents. They are potentially useful as immunotherapeutic agents for the treatment of a wide range of diseases, e.g., infections and cancers. As demonstrated herein, these lipid A analogs are potent vaccine adjuvants. An immunostimulatory adjuvant stimulates the production of cytokines required for antigen specific antibody response, and cell-mediated immune responses including a cytotoxic-lymphocytes, in the immunized host.

The compounds of the present invention can be formulated with a pharmaceutically acceptable carrier for injection or ingestion. The pharmaceutically acceptable carrier is a medium that does not interfere with the immunomodulatory activity of the active ingredient and is not toxic to the host to which it is administered. Pharmaceutically acceptable carriers include without limitation oil-in-water or water-in-oil emulsions, aqueous compositions, liposomes, micro beads and microsomes. As vaccine adjuvants, they can be formulated together with antigens to provide stronger immune responses and improve vaccine efficacy. Typically, an antigen is formulated in combination or separately with an immunostimulatory adjuvant compounds such as those described in the present invention, to provide the pharmaceutical composition. In other formulations, an antigen may be covalently linked to an amino, carboxyl, hydroxyl, and/or phosphate moiety of the adjuvant compounds of the present invention.

Antigens may be derived from pathogenic and non-pathogenic organisms, viruses, and fungi, or may be the whole organism. More specifically, the antigenic agent may be selected from the group consisting of: (1) live, heat killed, or chemically attenuated viruses, bacteria, mycoplasmas, fungi, and protozoa; (2) fragments, extracts, subunits, metabolites and recombinant constructs of (1); (3) fragments, subunits, metabolites and recombinant constructs of mammalian proteins and glycoproteins; (4) tumor-associated and tumor-specific antigens; and (5) nucleic acids.

The therapeutic composition may therefore utilize any suitable antigen or vaccine component in combination with an immunostimulating compound of the present invention as an adjuvant. Such therapeutic compositions may suitably comprise proteins, peptides, glycopeptides and glycolipids which are pharmaceutically active for disease states and conditions such as cancers, malaria, smallpox, anthrax, and SARS (sudden acute respiratory syndrome).

The modes of administration may comprise the use of any suitable means and/or methods for delivering the immunostimulatory adjuvant, adjuvant containing vaccine, or adjuvant and/or antigen to the host. Delivery modes may include, but not limited to, parenteral administration methods, such as subcutaneous (SC) injection, transcutaneous, intranasal (IN), ophthalmic, transdermal, intramuscular (IM), intradermal (ID), intraperitoneal (IP), intravaginal, pulmonary, and rectal administration, as well as non-parenteral, e.g., oral administration.

The immunostimulatory agents of the present invention may be usefully administered to the host with other therapeutic agents for the treatment of targeted diseases in combined therapy to achieve better efficacy. For example, they can be used in combination with antibiotics, anti-viral agents, and anti-inflammatory agents to provide better treatment for infections and autoimmune diseases. Formulation comprising of the immunostimulatory compounds of the present invention can include additional components such as saline, oil, squalene, and other immunostimulatory compounds such as muramyl peptide analogs, bacterial DNA, CpG-oligonucleotide analogs, QS-21 (an immunostimulatory adjuvant derived from plant), and lipid A analogs not of the present invention disclosure.

Lipid A Analogs as Bacterial Endotoxin Antagonists

Lipid A analogs with LPS/lipid A antagonistic activity may be used for the control of LPS-mediated pathophysiological disorders. Upon Gram-negative bacterial infection in humans, bacterial endotoxin, lipopolysaccharides (LPS), are released into the blood streams. Acute inflammatory responses to LPS or its active principle lipid A result in the release of cytokines and other cellular mediators, including tumor necrosis factor-$\alpha$ (TNF-$\alpha$), interleukun-1 (IL-1), IL-6 and leukotrienes from monocytes and macrophages. At extreme levels, these cytokines and cellular mediators are known to trigger many pathophysiological events including fever, shock, hypotension, and organ failure (R. C. Bone, *Clin. Microbiol. Rev.* 1993, 6, 57). These events are generally termed as septic syndrome. Sepsis is deadly and kills tens of thousands of people annually in US alone.

One strategy to control LPS-mediated disorders is to prevent LPS/lipid A binding to receptors with inactive competitors (antagonists) of LPS/lipid A. Lipid A analogs disclosed herein, due to their structural similarity to the natural lipid A molecules, are expected to bind to the LPS-binding receptor, Toll-like receptor 4 (TLR4), but without triggering the uncontrolled release of inflammatory cytokines by the immune system. As LPS/lipid A-antagonists, such lipid A analogs can inhibit LPS-induced production of cytokines and thus confer benefits in controlling LPS-mediated pathophysiological disorders.

As LPS-antagonists to neutralize the toxicity of bacterial endotoxin, such lipid A compositions are expected to display higher therapeutic benefits when administered at early stage of bacterial infections. In addition, such lipid A analogs could be administered in conjunction with common antibiotics to relieve the burden to the host caused by the infections. In short, the lipid A analogs described herein as LPS-antagonists are useful therapeutic agents for the treatment or prevention of LPS-mediated disorders resulting from Gram-negative bacterial infections. Such disorders include, without limitation, fever, generalized inflammation, disseminated intravascular coagulation, hypotension, acute renal failures, acute respiratory distress syndrome, hepatocellular destruction, and cardiac failure.

Another embodiment of the application of lipid A analogs disclosed herein is to suppress LPS-mediated virus production. LPS potently stimulates the production of viruses which reside in monocytes or macrophages (Ponerantz et al. *J. Exp. Med.* 1990, 127, 253). In the case of HIV-1, increased viral production likely results from activation of cells by both a direct activation by LPS and the LPS-mediated elevation in TNF-α levels. Cellular activation promotes increased binding of trans-acting factors to the HIV-1 NF-κB binding site, which in turn leads to increased viral transcription and replication (Duh et al.; *Proc. Natl. Acad. Sci. USA,* 1989, 85, 5974). Thus, as LPS-antagonists, the lipid A analogs disclosed herein can inhibit an LPS-mediated increase in HIV-1 replication. Similarly, these lipid A analogs may be used to suppress the activation of any virus whose replication is directly or indirectly controlled by an NF-κB regulatory region. Such viruses include, without limitation, cytomegalovirus or Herpes viruses. Furthermore, LPS has been implicated in influenza virus activation (Nain et al., *J. Immunol.* 1990, 145, 1921), and an enhanced release of TNF-α has been suggested to be related with the observed complications of combined influenza and bacterial infections. Therefore the lipid A analogs with LPS-antagonistic activities disclosed herein may be used to suppress influenza virus activation as well. In brief, the compositions of the present invention can provide useful therapeutics for the treatment or prevention of LPS-mediated exacerbation of latent or active viral infections, e.g., infection with HIV-1, cytomegaloviruses, herpes simplex viruses, and influenza virus.

Pharmaceutical Subjects, Preparations and Methods

Applicants hereby incorporate by reference the discussion at pp. 32-46 of WO98/33810.

Subjects

The recipients of the vaccines of the present invention may be any vertebrate animal which can acquire specific immunity via a humoral or cellular immune response.

Among mammals, the preferred recipients are mammals of the Orders Primata (including humans, apes and monkeys), Arteriodactyla (including horses, goats, cows, sheep, pigs), Rodenta (including mice, rats, rabbits, and hamsters), and Carnivora (including cats, and dogs). Among birds, the preferred recipients are turkeys, chickens and other members of the same order. The most preferred recipients are humans.

The preferred animal subject of the present invention is a primate mammal. By the term "mammal" is meant an individual belonging to the class Mammalia, which, of course, includes humans. The invention is particularly useful in the treatment of human subjects, although it is intended for veterinary uses as well. By the term "non-human primate" is intended any member of the suborder Anthropoidea except for the family Hominidae. Such non-human primates include the superfamily Ceboidea, family Cebidae (the New World monkeys including the capuchins, howlers, spider monkeys and squirrel monkeys) and family Callithricidae (including the marmosets); the superfamily Cercopithecoidea, family Cercopithecidae (including the macaques, mandrills, baboons, proboscis monkeys, mona monkeys, and the sacred hunaman monkeys of India); and superfamily Hominoidea, family Pongidae (including gibbons, orangutans, gorillas, and chimpanzees). The rhesus monkey is one member of the macaques.

Pharmaceutical Compositions

Pharmaceutical preparations of the present invention, comprise at least one immunogen in an amount effective to elicit a protective immune response. The response may be humoral, cellular, or a combination thereof. The composition may comprise a plurality of immunogens.

At least one immunogen will be either a glycolipopeptide which is immunogenic per se, or a glycolipopeptide which is immunogenic as a result of its incorporation into a liposome.

The composition preferably further comprises a liposome. Preferred liposomes include those identified in Jiang, et al., PCT/US00/31281, filed Nov. 15, 2000, and Longenecker, et al., Ser. No. 08/229,606, filed Apr. 12, 1994, and PCT/US95/04540, filed Apr. 12, 1995.

The composition may comprise antigen-presenting cells, and in this case the immunogen may be pulsed onto the cells, prior to administration, for more effective presentation.

The composition may contain auxiliary agents or excipients which are known in the art. See, e.g., Berkow et al, eds., *The Merck Manual,* 15th edition, Merck and Co., Rahway, N.J., 1987; Goodman et al., eds., *Goodman and Gilman's The Pharmacological Basis of Therapeutics,* 8th edition, Pergamon Press, Inc., Elmsford, N.Y., (1990); *Avery's Drug Treatment: Principles and Practice of Clinical Pharmacology and Therapeutics,* 3rd edition, ADIS Press, LTD., Williams and Wilkins, Baltimore, Md. (1987), Katzung, ed. *Basic and Clinical Pharmacology,* Fifth Edition, Appleton and Lange, Norwalk, Conn. (1992), which references and references cited therein, are entirely incorporated herein by reference.

A composition may further comprise an adjuvant to non-specifically enhance the immune response. Some adjuvants potentiate both humoral and cellular immune response, and others are specific to one or the other. Some will potentiate one and inhibit the other. The choice of adjuvant is therefore dependent on the immune response desired.

A composition may include immunomodulators, such as cytokines which favor or inhibit either a cellular or a humoral immune response, or inhibitory antibodies against such cytokines.

A pharmaceutical composition according to the present invention may further comprise at least one cancer chemotherapeutic compound, such as one selected from the group consisting of an anti-metabolite, a bleomycin peptide antibiotic, a podophyllin alkaloid, a Vinca alkaloid, an alkylating agent, an antibiotic, cisplatin, or a nitrosourea. A pharmaceutical composition according to the present invention may further or additionally comprise at least one viral chemotherapeutic compound selected from gamma globulin, amantadine, guanidine, hydroxybenzimidazole, interferon-α, interferon-β, interferon-γ, thiosemicarbarzones, methisazone, rifampin, ribvirin, a pyrimidine analog, a purine analog, foscarnet, phosphonoacetic acid, acyclovir, dideoxynucleosides, or ganciclovir. See, e.g., Katzung, supra, and the references cited therein on pages 798-800 and 680-681, respectively, which references are herein entirely incorporated by reference.

Anti-parasitic agents include agents suitable for use against arthropods, helminths (including roundworms, pinworms, threadworms, hookworms, tapeworms, whipworms, and Schistosomes), and protozoa (including amebae, and malarial, toxoplasmoid, and trichomonad organisms). Examples include thiabenazole, various pyrethrins, praziquantel, niclosamide, mebendazole, chloroquine HCl, metronidazole, iodoquinol, pyrimethamine, mefloquine HCl, and hydroxychloroquine HCl.

Pharmaceutical Purposes

A purpose of the invention is to protect subjects against a disease. The term "protection", as in "protection from infection or disease", as used herein, encompasses "prevention," "suppression" or "treatment." "Prevention" involves administration of a Pharmaceutical composition prior to the induction of the disease. "Suppression" involves administration of the composition prior to the clinical appearance of the disease. "Treatment" involves administration of the protective composition after the appearance of the disease. Treatment may be ameliorative or curative.

It will be understood that in human and veterinary medicine, it is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis." See, e.g., Berker, supra, Goodman, supra, Avery, supra and Katzung, supra, which are entirely incorporated herein by reference, including all references cited therein.

The "protection" provided need not be absolute, i.e., the disease need not be totally prevented or eradicated, provided that there is a statistically significant improvement (p=0.05) relative to a control population. Protection may be limited to mitigating the severity or rapidity of onset of symptoms of the disease. An agent which provides protection to a lesser degree than do competitive agents may still be of value if the other agents are ineffective for a particular individual, if it can be used in combination with other agents to enhance the level of protection, or if it is safer than competitive agents.

The effectiveness of a treatment can be determined by comparing the duration, severity, etc. of the disease post-treatment with that in an untreated control group, preferably matched in terms of the disease stage.

The effectiveness of a prophylaxis will normally be ascertained by comparing the incidence of the disease in the treatment group with the incidence of the disease in a control group, where the treatment and control groups were considered to be of equal risk, or where a correction has been made for expected differences in risk.

In general, prophylaxis will be rendered to those considered to be at higher risk for the disease by virtue of family history, prior personal medical history, or elevated exposure to the causative agent.

Pharmaceutical Administration

At least one protective agent of the present invention may be administered by any means that achieve the intended purpose, using a pharmaceutical composition as previously described.

Administration may be oral or parenteral, and, if parenteral, either locally or systemically. For example, administration of such a composition may be by various parenteral routes such as subcutaneous, intravenous, intradermal, intramuscular, intraperitoneal, intranasal, transdermal, or buccal routes. Parenteral administration can be by bolus injection or by gradual perfusion over time. A preferred mode of using a pharmaceutical composition of the present invention is by subcutaneous, intramuscular or intravenous application. See, e.g., Berker, supra, Goodman, supra, Avery, supra and Katzung, supra, which are entirely incorporated herein by reference, including all references cited therein.

A typical regimen for preventing, suppressing, or treating a disease or condition which can be alleviated by an immune response by active specific immunotherapy, comprises administration of an effective amount of a pharmaceutical composition as described above, administered as a single treatment, or repeated as enhancing or booster dosages, over a period up to and including between one week and about 24 months.

It is understood that the effective dosage will be dependent upon the age, sex, health, and weight of the recipient, kind of concurrent treatment, if any, frequency of treatment, and the nature of the effect desired. The ranges of effective doses provided below are not intended to limit the invention and represent preferred dose ranges. However, the most preferred dosage will be tailored to the individual subject, as is understood and determinable by one of skill in the art, without undue experimentation. This will typically involve adjustment of a standard dose, e.g., reduction of the dose if the patient has a low body weight. See, e.g., Berkow et al, eds., *The Merck Manual,* 15th edition, Merck and Co., Rahway, N.J., 1987; Goodman et al., eds., *Goodman and Gilman's The Pharmacological Basis of Therapeutics,* 8th edition, Pergamon Press, Inc., Elmsford, N.Y., (1990); *Avery's Drug Treatment: Principles and Practice of Clinical Pharmacology and Therapeutics,* 3rd edition, ADIS Press, LTD., Williams and Wilkins, Baltimore, Md. (1987), Ebadi, *Pharmacology,* Little, Brown and Co., Boston, (1985); Chabner et al., supra; De Vita et al., supra; Salmon, supra; Schroeder et al., supra; Sartorelli et al., supra; and Katsung, supra, which references and references cited therein, are entirely incorporated herein by reference.

Prior to use in humans, a drug will first be evaluated for safety and efficacy in laboratory animals. In human clinical studies, one would begin with a dose expected to be safe in humans, based on the preclinical data for the drug in question, and on customary doses for analogous drugs (if any). If this dose is effective, the dosage may be decreased, to determine the minimum effective dose, if desired. If this dose is ineffective, it will be cautiously increased, with the patients monitored for signs of side effects. See, e.g., Berkow, et al., eds., *The Merck Manual,* 15th edition, Merck and Co., Rahway, N.J., 1987; Goodman, et al., eds., *Goodman and Gilman's The Pharmacological Basis of Therapeutics,* 8th edition, Pergamon Press, Inc., Elmsford, N.Y., (1990); *Avery's Drug Treatment: Principles and Practice of Clinical Pharmacology and Therapeutics,* 3rd edition, ADIS Press, LTD., Williams and Wilkins, Baltimore, Md. (1987), Ebadi, *Pharmacology,* Little, Brown and Co., Boston, (1985), which references and references cited therein, are entirely incorporated herein by reference.

The total dose required for each treatment may be administered in multiple doses (which may be the same or different) or in a single dose, according to an immunization schedule, which may be predetermined or ad hoc. The schedule is selected so as to be immunologically effective, i.e., so as to be sufficient to elicit an effective immune response to the antigen and thereby, possibly in conjunction with other agents, to provide protection. The doses adequate to accomplish this are defined as "therapeutically effective doses." (Note that a schedule may be immunologically effective even though an individual dose, if administered by itself, would not be effective, and the meaning of "therapeutically effective dose" is best interpreted in the context of the immunization schedule.) Amounts effective for this use will depend on, e.g., the peptide composition, the manner of administration, the stage and severity of the disease being treated, the weight and general state of health of the patient, and the judgment of the prescribing physician.

Typically, the daily dose of an active ingredient of a pharmaceutical, for a 70 kg adult human, is in the range of 10 nanograms to 10 grams. For immunogens, a more typical daily dose for such a patient is in the range of 10 nanograms to 10 milligrams, more likely 1 microgram to 10 milligrams. However, the invention is not limited to these dosage ranges.

It must be kept in mind that the compositions of the present invention may generally be employed in serious disease states, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions.

The doses may be given at any intervals which are effective. If the interval is too short, immunoparalysis or other adverse effects can occur. If the interval is too long, immunity may suffer. The optimum interval may be longer if the individual doses are larger. Typical intervals are 1 week, 2 weeks, 4 weeks (or one month), 6 weeks, 8 weeks (or two months) and one year. The appropriateness of administering additional doses, and of increasing or decreasing the interval, may be reevaluated on a continuing basis, in view of the patient's immunocompetence (e.g., the level of antibodies to relevant antigens).

A variety of methods are available for preparing liposomes, as described in, e.g., Szoka et al., *Ann. Rev. Biophys. Bioeng.* 9:467 (1980), U.S. Pat. Nos. 4,235,871, 4,501,728, 4,837,028, and 5,019369, incorporated herein by reference.

The appropriate dosage form will depend on the disease, the immunogen, and the mode of administration; possibilities include tablets, capsules, lozenges, dental pastes, suppositories, inhalants, solutions, ointments and parenteral depots. See, e.g., Berker, supra, Goodman, supra, Avery, supra and Ebadi, supra, which are entirely incorporated herein by reference, including all references cited therein.

The antigen may be delivered in a manner which enhance, e.g., delivering the antigenic material into the intracellular compartment such that the "endogenous pathway" of antigen presentation occurs. For example, the antigen may be entrapped by a liposome (which fuses with the cell), or incorporated into the coat protein of a viral vector (which infects the cell).

Another approach, applicable when the antigen is a peptide, is to inject naked DNA encoding the antigen into the host, intramuscularly. The DNA is internalized and expressed.

It is also possible to prime autologous PBLs with the compositions of the present invention, confirm that the PBLs have manifested the desired response, and then administer the PBLs, or a subset thereof, to the subject.

EXAMPLES

General: Melting points were not corrected. All air and moisture sensitive reactions were performed under nitrogen atmosphere. Anhydrous THF, DMF and dichloromethane were purchased from Aldrich and other dry solvents were prepared in the usual way. ACS grade solvents were purchased from Fisher and used for chromatography without distillation. TLC plates (silica gel 60 $F_{254}$, thickness 0.25 mm, Merck) and flash silica gel 60 (35-75 mm) for column chromatography were purchased from Rose Scientific, Canada. $^1H$ and $^{31}P$ spectra were recorded either on a Brucker AM 300 MHz or Varian Unity 500 MHz or Brucker DRX 600 MHz spectrometers with TMS as internal standard for proton chemical shifts. Optical rotations were measured on a Perkin-Elmer 241 Polarimeter at room temperature (20-22° C.). Elemental analysis data were obtained from the Micro-analytical laboratory in the University of Alberta. Electron-spray mass spectrometric analyses were performed either on a MS50B or MSD1 SPC mass spectrometers.

Example 1

Preparation of Compound 8

Compound 6 (312 mg, 0.65 mmol), 7 (200 mg, 0.44 mmol), DCC (136 mg, 0.66 mmol) and DMAP (27 mg, 0.22 mmol) were dissolved in dry dichloromethane (5 ml). The mixture was stirred at room temperature for 4 h. The solid was filtered off and washed with ethyl acetate (5 ml). The filtrate was concentrated and the residue was purified by flash chromatography (hexane:ethyl acetate, 8:1) to give 8 (398 mg, 98%). TLC: $R_f$=0.69 (hexane:ethyl acetate, 3:1). $[a]_D^{22}$=+32.0 (c 0.5, chloroform). $^1H$ NMR (300 MHz, $CDCl_3$): d 0.90 (t, J=6.5 Hz, 6H, $2CH_3$), 1.25 (m, 38H, $19CH_2$), 1.52 (m, 4H, $2CH_2$), 2.16 (t, J=7.5 Hz, 2H, $CH_2$), 2.50 (dd, J=16.0, 6.0 Hz, 1H, CHH), 2.63 (dd, J=16.0, 6.0 Hz, 1H, CHH), 3.71 (dd, J=9.5, 9.5 Hz, 1H, H-4), 3.78 (dd, J=10.0, 10.0 Hz, 1H, H-6a), 3.94 (m, 1H, H-5), 3.98-4.08 (m, 2H, H-2, CHHCH=$CH_2$), 4.21 (m, 1H, CHHCH=$CH_2$), 4.29 (dd, J=10.0, 5.0 Hz, 1H, H-6b), 4.69, 4.76 (2 d, J=12.0 Hz, each 1H, Troc-$CH_2$), 4.94 (d, J=3.6 Hz, 1H, H-1), 5.16 (m, 1H, lipid-3-H), 5.30 (m, 2H, CH=$CH_2$), 5.39 (dd, J=9.5, 9.5 Hz, 1H, H-3), 5.42 (d, J=10.0 Hz, 1H, NH), 5.53 (s, 1H, CHPh), 5.90 (m, 1H, CH=$CH_2$), 7.30-7.35 (m, 15H, Ar—H). Anal. calcd for $C_{47}H_{74}Cl_3NO_{10}$ (919.46): C, 61.40; H, 8.11; N, 1.52. Found: C, 61.40; H, 8.19; N, 1.58.

Example 2

Preparation of Compound 9

To a solution of 8 (1.45 g, 1.60 mmol) in dry THF (20 ml) was added molecular sieves (4 A, 3.0 g). The mixture was stirred at room temperature under nitrogen for 20 min. Sodium cyanoborohydride (1.0 g, 15.96 mmol) was added and the mixture was cooled to 0° C. HCl (g)/$Et_2O$ solution was added drop wise slowly till no gas was evolved. The mixture was then poured into saturated sodium bicarbonate solution (50 ml) and extracted with dichloromethane (100 ml×3). Combined organic layers were washed with saturated sodium chloride solution (20 ml) and dried with sodium sulfate, and concentrated. The residue was purified by flash silica gel chromatography (initially with hexane:ethyl acetate, 5:1 and then 4:1) to give 9 (1.23 g, 85%). TLC: $R_f$=0.20 (hexane:ethyl acetate, 4:1). $[a]_D^{20}$=+47.5 (c 1.0, $CHCl_3$). $^1H$ NMR (300 MHz, $CDCl_3$): d 0.88 (t, J=6.5 Hz, 6H, $2CH_3$), 1.25 (br s, 38H, $19CH_2$), 1.50 (m, 4H, $2CH_2$), 2.28 (t, J=7.5 Hz, 2H, $CH_2$), 2.48 (dd, J=14.0, 4.0 Hz, 1H), 2.58 (dd, J=14.0, 7.5 Hz, 1H), 3.27 (d, J=3.5 Hz, 1H, OH), 3.70-3.86 (m, 4H), 3.92-4.03 (m, 2H), 4.58 (d, J=12.0 Hz, 1H), 4.64 (d, J=12.0 Hz, 1H), 4.66 (d, J=12.0 Hz, 1H), 4.76 (d, J=12.0 Hz, 1H), 4.92 (d, J=3.5 Hz, 1H, H-1), 5.13 (m, 2H), 5.19-5.31 (m, 2H), $CH_2$=CH), 5.40 (d, J=9.5 Hz, 1H, NH), 5.88 (m, 1H, $CH_2$=CH), 7.30 (m, 5H, Ar—H). ES-MS calcd for $C_{47}H_{76}Cl_3NO_{10}$: 919.5. Found: 920.8 (M+H).

Example 3

Preparation of Compound 10

To compound 9 (1.20 g, 1.30 mmol) in dry dichloromethane (20 ml) were added 1H-tetrazole (273 mg, 3.90 mmol) and dibenzyl diisopropylphosphoramidite (900 mg, 0.875 ml, 2.61 mmol). The mixture was stirred at room temperature for 30 min and then cooled to 0° C. m-Chloroperbenzoic acid (m-CPBA, 1.63 g, 55%, 5.22 mmol) was added and the mixture was stirred for 30 min at 0° C. The mixture was then poured into 10% sodium hydrogen sulfite (40 ml) and extracted with dichloromethane (40 ml×3). The organic layer was washed with saturated sodium bicarbonate solution (20 ml), dried with sodium sulfate and concentrated. The residue was purified by repeated flash chromatography (initially hexane:ethyl acetate, 4:1 and then 3:1). TLC: $R_f$=0.31 (hexane:ethyl acetate, 3:1) to give 10 (1.33 g, 86%). $[a]_D^{20}$=+35.0 (c 1.0, $CHCl_3$). $^1$H NMR (300 MHz, $CDCl_3$): d 0.88 (t, J=6.5 Hz, 6H, $2CH_3$), 1.24 (br s, 38H, $19CH_2$), 1.50 (m, 4H, $2CH_2$), 2.17 (t, J=7.0 Hz, 2H, $CH_2$), 2.41 (dd, J=16.5, 5.5 Hz, 1H), 2.51 (dd, J=16.5, 7.5 Hz, 1H), 3.66 (dd, J=11.0, 4.5 Hz, 1H), 3.74 (dd, J=11.0, 2.0 Hz, 1H), 3.91 (m, 1H), 4.00 (m, 2H), 4.20 (m, 1H), 4.44 (d, J=12.0 Hz, 1H), 4.53 (m, 1H, H-4), 4.54 (d, J=12.0, 1H), 4.63 (d, J=12.0, 1H), 4.88-4.95 (m, 5H), 5.11 (m, 1H), 5.20-5.32 (m, 2H, $CH_2$=CH), 5.35 (dd, J=10.5, 9.0 Hz, 1H, H-3), 5.41 (d, J=9.5 Hz, 1H, NH), 5.88 (m, 1H, $CH_2$=CH), 7.30 (m, 15H, Ar—H). ES-MS calcd for $C_{61}H_{89}Cl_3NO_{13}P$: 1179.6. Found: 1181.0 (M+H).

Example 4

Preparation of Compound 11

[Bis(methyldiphenylphosphine)](1,5-cyclooctadiene) iridium(I) hexafluorophosphate (14 mg, 0.0165 mmol) was suspended in dry THF (5 ml) and hydrogen gas was bubbled in for 5 min to give a yellowish solution, which was added to the solution of 10 (1.30 g, 1.10 mmol) in dry THF (10 ml). The mixture was stirred at room temperature for 2 hours. Water (0.5 ml) and N-bromosuccinimide (NBS, 294 mg, 1.62 mmol) were then added and the reaction was stirred for 1 hour longer. Remainder obtained from solvent removal was dissolved in ethyl acetate (200 ml) and washed with saturated sodium bicarbonate solution (20 ml×2). Combined organic layers were dried with sodium sulfate and concentrated. The residue was purified by flash chromatography (hexane:ethyl acetate, 2:1) to give 11 (950 mg, 76%). TLC: $R_f$=0.31 (ethyl acetate:hexane, 1:2). $[a]_D^{20}$=+17.5 (c 1.0, $CHCl_3$). $^1$H NMR (300 MHz, $CDCl_3$): d 0.88 (t, J=6.5 Hz, 6H, $2CH_3$), 1.24 (br s, 38H, $19CH_2$), 1.50 (m, 4H, $2CH_2$), 2.18 (t, J=7.0 Hz, 2H, $CH_2$), 2.39 (m, 2H, $CH_2$), 3.59 (dd, J=11.0, 6.0 Hz, 1H), 3.71 (dd, J=11.0, 1.5 Hz, 1H), 3.94 (m, 1H), 4.16 (m, 1H), 4.40 (m, 3H), 4.49 (d, J=12.0 Hz, 1H), 4.65 (d, J=12.0 Hz, 1H), 4.72 (d, J=12.0 Hz, 1H), 4.90 (m, 4H), 5.09 (m, 1H), 5.39 (t, J=3.5 Hz, 1H, H-1), 5.37 (dd, J=10.0, 9.5 Hz, 1H, H-3), 5.70 (d, J=9.5 Hz, 1H, NH), 7.30 (m, 15H, Ar—H). ES-MS calcd for $C_{58}H_{85}Cl_3NO_{13}P$: 1139.5. Found: 1141.0 (M+H).

Example 5

Preparation of Compound 12

To a solution of 11 (920 mg, 0.81 mmol) in dry dichloromethane (10 ml), trichloroacetonitrile (2 ml) and DBU (4 drops) were added. The mixture was stirred at room temperature for 2 h and concentrated in vacuo (not to dryness). The residue was purified by flash chromatography (hexane:ethyl acetate, 4:1, 3.5:1 and 3:1, with 0.5% of triethyl amine) to give 12 (700 mg, 68%). TLC: $R_f$=0.36 (hexane:ethyl acetate, 3:1). $[a]_D^{20}$=+12.5 (c 0.4, $CHCl_3$). $^1$H NMR (300 MHz, $CDCl_3$): d 0.88 (t, J=6.5 Hz, 6H, $2CH_3$), 1.24 (br s, 38H, $19CH_2$), 1.50 (m, 4H, $2CH_2$), 2.19 (t, J=7.0 Hz, 2H, $CH_2$), 2.46 (m, 2H, $CH_2$), 3.71 (m, 2H), 4.04 (m, 1H). 4.15 (ddd, J=1.0, 8.5, 3.5 Hz, 1H, H-2), 4.43 (d, J=12.0 Hz, 1H), 4.52 (d, J=12.0 Hz, 1H), 4.61 (d, J=12.0 Hz, 1H), 4.71 (ddd, J=9.5, 9.5, 9.5 Hz, 1H, H-4), 4.77 (d, J=12.0 Hz, 1H). 4.94 (m, 4H), 5.12 (m, 1H), 4.39 (dd, J=10.0, 9.5 Hz, 1H, H-3), 5.65 (d, J=8.5 Hz, 1H, NH), 6.47 (d, J=3.5 Hz, 1H, H-1), 7.32 (m, 15H, Ar—H), 8.72 (s, 1H, NH). ES-MS calcd for $C_{60}H_{85}Cl_6N_2O_{13}P$: 1282.4. Found: 1284.0 (M+H).

Example 6

Preparation of Compound 14

Compound 13 (672 mg, 2.97 mmol) was dissolved in dry acetonitrile (10 ml) and 2,2-dimethoxypropane (560 mg, 0.66 ml, 5.35 mmol) and p-toluenesulfonic acid (56 mg, 0.279 mmol) were added. The mixture was stirred at room temperature for 1 h and then triethylamine (0.5 ml) was added to quench the reaction. The mixture was concentrated in vacuo and the residue purified by flash chromatography (hexane/ethyl acetate, 2:1) to give 14 (614 mg, 82%). $R_f$=0.67 (hexane/ethyl acetate, 1:2). $^1$H NMR (300 MHz, $CDCl_3$): d=1.41 (s, 3H, $CH_3$), 1.42 (s, 3H, $CH_3$), 2.40 (br s, 1H, OH), 3.59 (s, 2H, $CH_2$), 3.69 (s, 2H, $CH_2$), 3.74 (s, 4H, $2CH_2$), 4.55 (s, 2H, $CH_2Ph$), 7.30 (m, 5H, Ar—H).

Example 7

Preparation of Compound 15

Compound 14 (572 mg, 2.26 mmol) was dissolved in dry pyridine (3 ml) and cooled to 0° C. P-Toluenesulfonyl chloride (5.7 mg, 2.71 mmol) was added and the mixture was stirred for 3 h. More p-toluenesulfonyl chloride (430 mg, 2.26 mmol) was added and the reaction mixture was stirred at room temperature overnight. Methanol (1 ml) was then added to quench the reaction and the solvent was removed in vacuo by co-distillation with toluene. The residue was dissolved in dichloromethane (100 ml) and washed with sat. $NaHCO_3$ (aq.) (30 ml). The aqueous layer was extracted with dichloromethane (30 ml) and the combined organic layer was dried with sodium sulfate and concentrated. The residue was purified by flash chromatography (hexane/ethyl acetate, 5:1) to give 15 (930 mg, 98%). $R_f$=0.65 (hexane/ethyl acetate, 2:1). $^1$H NMR (300 MHz, $CDCl_3$): d=1.30 (s, 3H, $CH_3$), 1.40 (s, 3H, $CH_3$), 2.42 (s, 3H, $CH^3$), 3.35 (s, 2H, $CH_2$), 3.63 (d, J=12.0 Hz, 2H), 3.72 (d, J=12.0 Hz, 2H), 4.20 (s, 4H, $2CH_2$), 4.50 (s, 2H, $CH_2Ph$), 7.30 (m, 7H, Ar—H), 7.78 (m, 2H, Ar—H). ES-MS calcd for $C_{22}H_{28}O_6S$: 420.2. found: 443.2 (M+Na).

Example 8

Preparation of Compound 16

Compound 15 (907 mg, 2.16 mmol) was dissolved in toluene (30 ml) and sat. NaHCO3 (aq.) (30 ml), sodium azide (561 mg, 8.63 mmol), and phase transfer catalyst ALIQUAT (433 mg, 0.49 ml, 1.08 mmol) were added. The mixture was refluxed for 16 h and more sodium azide (1.40 g, 21.60 mmol) was added. The reaction was continued for 24 h and then cooled to room temperature. The organic layer was separated and the aqueous layer was extracted with ethyl acetate (30 ml×3). The combined organic layer was washed with water (30 ml), dried with sodium sulfate, and concentrated in vacuo. The residue was purified by flash chromatography (hexane/ethyl acetate, 8:1) to give 16 (440 mg, 70%) and the starting material 15 (163 mg, 18%). $R_f$=0.34 (hexane/ethyl acetate, 6:1). $^1$H NMR (500 MHz, CDCl$_3$): d=1.42 (s, 6H, 2CH$_3$), 3.40 (s, 2H, CH$_2$), 3.52 (s, 2H, CH$_2$), 3.64 (d, J=12.0 Hz, 2H), 3.73 (d, J=12.0 Hz, 2H), 4.50 (s, 2H, CH$_2$Ph), 7.30 (m, 5H, Ar—H) ES-MS calcd for C$_{15}$H$_{21}$N$_3$O$_3$: 291.2. found: 314.1 (M+Na). ES-MS calcd for C$_{15}$H$_{21}$N$_3$O$_3$: 291.2. found: 314.1 (M+Na).

Example 9

Preparation of Compound 17

Compound 16 (40 mg, 0.137 mmol) was dissolved in acetic acid (10 ml) and zinc powder (1.0 g) was added. The mixture was stirred at room temperature for 1 h and the solid was filtered out and washed with acetic acid (10 ml). The filtrate was concentrated in vacuo. The residue was dissolved in dioxane-sat. NaHCO$_3$(aq.) (2:1, 6 ml, PH 8~9) and 2,2,2-trichloroethoxylchloroformate (123 mg, 0.08 ml, 0.568 mmol) was added. The mixture was stirred at room temperature for 6 h. The dioxane was then removed in vacuo and water (10 ml) was added. The mixture was extracted with ethyl acetate (10 ml×3) and the organic layer was dried with sodium sulfate and concentrated in vacuo. The residue was purified by flash chromatography (hexane/ethyl acetate, 4:1) to give 17 (28 mg, 47%). $R_f$=0.17 (hexane/ethyl-acetate, 6:1). $^1$H NMR (300 MHz, CDCl$_3$): d=1.39 (s, 3H, CH$_3$), 1.41 (s, 3H, CH$_3$), 3.32 (d, J=6.0 Hz, 2H, CH$_2$), 3.54 (s, 2H, CH$_2$), 3.67 (d, J=12.0 Hz, 2H), 3.75 (d, J=12.0 Hz, 2H), 4.57 (s, 2H), 4.72 (s, 2H), 5.50 (t, J=6.0 Hz, 1H, NH), 7.35 (m, 5H, Ar—H). ES-MS calcd for C$_{18}$H$_{24}$Cl$_3$NO$_5$: 439.1. found: 462.1 (M+Na), 464.1 (M+Na, $^{37}$Cl).

Example 10

Preparation of Compound 18

Compound 17 (18.3 mg, 0.0417 mmol) was dissolved in acetic acid-water (4:1, 10 ml) and treated at 60° C. for 45 min. The solvent was removed in vacuo and the residue was purified by flash chromatography (hexane/ethyl acetate, 1:1) to give 18 (15 mg, 90%). $^1$H NMR (300 MHz, CDCl$_3$): d=3.03 (t, J=6.5 Hz, 2H, 2OH), 3.43 (s, 2H, CH$_2$), 3.44 (d, J=6.5 Hz, 2H, CH$_2$NH), 3.51 (d, J=6.5 Hz, 4H, 2CH$_2$OH), 4.55 (s, 2H), 4.73 (s, 2H), 5.35 (t, J=6.5 Hz, 1H, NH), 7.35 (m, 5H, Ar—H). ES-MS calcd for C$_{15}$H$_{20}$Cl$_3$NO$_5$: 399.0. found: 422.0 (M+Na), 424.0 (M+Na, $^{37}$Cl).

Example 11

Preparation of Compound 19

To a solution of 12 (620 mg, 0.484 mmol) and 18 (750 mg, 1.936 mmol) in dry dichloromethane (15 ml) was added molecular sieves (4 A, 2.0 g) and the mixture was stirred under nitrogen for 10 min at room temperature. Trimethysilyl trifluoromethanesulfonate (TMSOTf) solution (0.01 M in dichloromethane) (3.0 ml) was added drop wise within 5 min. The mixture was stirred at room temperature for 1 h and saturated sodium bicarbonate solution (10 ml) was added to quench the reaction. Usual aqueous work-up and flash chromatography (hexane/acetone, 2.8:1 and 2:1) afforded 19 (590 mg, 81) as a diastereomeric mixture in a ratio of about 1:1. $R_f$=0.27 (hexane/acetone, 2.5:1). $[a]_D^{20}$=−7.6 (c 0.8, chloroform). $^1$H NMR (300 MHz, CDCl$_3$): d=0.88 (t, J=6.5 Hz, 6H, 2CH$_3$), 1.25 (br s, 36H, 18CH$_2$), 1.45 (m, 2H, CH$_2$), 1.58 (m, 2H, CH$_2$), 1.68 (m, 2H, CH$_2$), 2.23 (t, J=7.5 Hz, 2H, CH$_2$), 2.41 (m, 2H, CH$_2$), 3.10 (m, 0.5H), 3.30-3.62 (m, 7.5 Hz), 3.68-3.83 (m, 2H), 4.40-4.56 (m, 7H), 4.65-4.80 (m, 5H), 4.90 (m, 5H), 5.19 (m, 2H), 5.53 (d, J=9.0 Hz, 0.5H, NH), 5.72 (m, 1.5H, NH), 7.30 (m, 20H, Ar—H). ES-MS calcd for C$_{73}$H$_{103}$C$_{16}$N$_2$O$_{17}$P: 1520.5. found: 1543.5 (M+Na, 42), 1544.4 (M+Na, $^{13}$C-isotope, 34), 1545.5 (M+Na, $^{37}$Cl-isotope, 100).

Example 12

Preparation of Compound 20

Compound 19 (450 mg, 0.30 mmol) was dissolved in acetic acid (50 ml) and zinc power (4.0 mg) was added. The mixture was stirred at room temperature for 1 h and the solid was filtered out. The solid was further washed with acetic acid (50 ml) and the filtrate was concentrated in vacuo. The residue was dissolved in dichloromethane (150 ml) and the solution was washed with saturated aqueous sodium bicarbonate solution (20 ml). The aqueous layer was back washed with dichloromethane (20 ml×2). The combined organic layer was dried with sodium sulphate and concentrated in vacuo to give the di-amine intermediate (346 mg) A mixture of the di-amine (346 mg) and lipid acid 7 (545 mg, 1.20 mmol) and DCC (371 mg, 1.80 mmol) in dry dichloromethane (10 ml) was stirred at room temperature for 20 h. Water (0.05 ml) was added and the reaction mixture was stirred for 10 min. The solid was filtered out through a sintered glass funnel bedded with sodium sulphate. The filtrate was concentrated and the residue purified by flash chromatography (hexane/acetone, 5:1 and 4.5:1) to give 20 (390 mg, 64%). $R_f$=0.20 (hexane/acetone, 4:1). $[a]_D^{20}$=−9.4 (c 0.5, chloroform). $^1$H NMR (500 MHz, CDCl$_3$): d=0.88 (t, J=7.0 Hz, 18H, 6CH$_3$), 1.25-1.50 (m, 112H, 56CH$_2$), 1.58 (m, 11H), 1.71-1.81 (m, 3H), 1.97 (m, 1H, OH), 2.21 (t, J=7.5 Hz, 2H, CH$_2$), 2.24-2.63 (m, 10H, 5CH$_2$), 3.06 (dd, J=14.0, 5.0 Hz, 0.5H), 3.17 (dd, J=14.0, 6.0 Hz, 0.5 Hz), 3.30-3.40 (m, 3H), 3.43-3.53 (m, 2H), 3.57-3.63 (m, 2.5H), 3.67-3.80 (m, 2H), 3.87 (m, 1H), 3.97 (m, 0.5H), 4.35 (d, J=8.0 Hz, 0.5H, H-1), 4.38-4.53 (m, 5H), 4.65 (d, J=8.0 Hz, 0.5H, H-1), 4.90 (m, 4H), 5.07-5.24 (m, 4H), 6.04 (d, J=8.5 Hz, 0.5H, NH), 6.38 (d, J=7.5 Hz, 0.5H, NH), 6.65 (dd, J=6.5, 6.5 Hz, 0.5H, NH), 6.79 (dd, J=7.0, 6.0 Hz, 0.5H, NH), 7.30 (m, 20H, Ar—H). ES-MS calcd. for C$_{123}$H$_{205}$N$_2$O$_{19}$P: 2045.5. found: 2068.5 (M+Na, 63), 2069.5 (M+Na, $^{13}$C-isotope, 100).

Example 13

Preparation of Compound 21

To a solution of compound 20 (220 mg, 0.108 mmol) in dry dichloromethane (5 ml) were added dibenzyl diisopropyl phosphoramidite (74.3 mg, 74.3 µl, 0.215 mmol) and 1H-tetrazole (22.7 mg, 0.324 mmol). The mixture was stirred at room temperature for 30 min and then cooled to 0° C. m-Chloroperbenzoic acid (m-CPBA, 55%, 118 mg, 0.379 mmol) was added and the mixture was stirred at 0° C. for 30 min. The mixture was diluted with dichloromethane (100 ml) and washed with aqueous sodium bisulphite solution (10%, 20 ml) and the aqueous layer was extracted with dichloromethane (20 ml). The combined organic layer was then washed with saturated sodium bicarbonate solution (20 ml) and aqueous layer was back washed with dichloromethane (20 ml). The combined organic layer was then dried with sodium sulphate and concentrated in vacuo. The residue was purified by repeated flash chromatography (hexane/acetone, 5:1 and then 4.5:1; dichloromethane/methanol, 100:1 and then 100:1.5; exane/ethyl acetate, 2:1 and then 1.5:1) to give 21 (200 mg, 80%) as a diastereomeric mixture in a ratio of about 1:1. $R_f$ (upper spot)=0.29 and $R_f$ (lower spot)=0.25 (hexane/acetone, 3:1). $[a]_D^{20}$ (~1:1 mixture)=−7.6 (c 0.5, chloroform). $^1$H NMR (300 MHz, CDCl$_3$): d=0.87 (t, J=6.5 Hz, 18H, 6CH$_3$), 1.30 (m, 108H, 54CH$_2$), 1.48-1.70 (m, 18H), 2.10-2.53 (m, 11H), 2.90-3.35 (m, 5H), 3.55 (m, 2H), 3.75-3.90 (m, 4H), 4.00 (m, 1H), 4.36-4.52 (m, 6H), 4.85-5.01 (m, 8H), 5.08-5.22 (m, 4H), 6.30 (m, 1H, NH), 6.88 (d, J=8.5 Hz, 0.5H, NH), 7.00 (d, J=8.0 Hz, 0.5H, NH), 7.30 (m, 30H, Ar—H). ES-MS calcd. for $C_{137}H_{218}N_2O_{22}P$: 2305.5. found: 2328.5 (M+Na, 78), 2329.5 (M+Na, $^{13}$C-isotope, 100).

Example 14

Preparation of Compound 1

Compound 20 (96 mg, 0.047 mmol) was dissolved in THF-HOAC (10:1, 77 ml) and palladium on charcoal (100 mg) was added. The mixture was stirred under hydrogen atmosphere for 24. The solid was then filtered out and washed with chloroform/methanol (1:1, 30 ml). The filtrate was concentrated in vacuo and the residue purified by flash chromatography (chloroform/methanol/water, 9:1:0 and then 4:1:0.1) to give 1 which was freeze dried from tert-butanol to afford the product as white powder. (80 mg, 100%). $R_f$=0.16 (chloroform/methanol/water/acetic acid, 6:1:0.1:0.1). $[a]_D^{20}$=−6.5 (c 0.2, chloroform). $^1$H NMR (600 MHz, CDCl$_3$—CD$_3$OD, 1:1): d=0.89 (t, J=6.5 Hz, 18H, 6CH$_3$), 1.26 (m, 114H, 57H), 1.60 (m, 12H, 6CH$_2$), 2.30 (m, 6H, 3CH$_2$), 2.37 (dd, J=15.0, 6.0 Hz, 1H), 2.45 (dd, J=15.0, 7.0 Hz, 1H), 2.50 (dd, J=15.0, 5.0 Hz, 1H), 2.54 (dd, J=15.0, 8.0 Hz, 1H), 2.57 (dd, J=15.0, 5.0 Hz, 1H), 2.67 (dd, J=15.0, 7.0 Hz, 1H), 3.04 (dd, J=14.0, 6.0 Hz, 1H), 3.18 (dd, J=14.0, 6.0 Hz, 1H), 3.25 (d, J=10.0 Hz, 1H), 3.29 (d, J=10.0 Hz, 1H), 3.36 (m, 3H), 3.37 (d, J=10.0 Hz, 1H), 3.64 (d, J=10.0 Hz, 1H), 3.77 (br d, J=12.0 Hz, 1H), 3.89 (dd, J=10.0, 9.0 Hz, 1H), 3.96 (br d, J=12.0 Hz, 1H), 4.25 (m, 1H, H-4), 4.43 ((d, J=8.5 Hz, 1H, H-1), 5.07 (dd, H=10.0, 10.0, Hz, 1H, H-3), 5.17 (m, 2H), 5.23 (m, 1H). ES-MS calcd. for $C_{95}H_{181}N_2O_{19}P$: 1685.3. found: 1686.3 (M+H), 1708.3 (M+Na), 730.3 (M+2Na—H).

Example 15

Preparation of Compound 2

In a similar was as described for 1, compound 21 (104 mg, 0.045 mmol) was treated with palladium on charcoal (100 mg) in THF-HOAc (10:1, 77 ml) under hydrogen atmosphere for 20 h to give 2 (77 mg, 96%) after flash chromatography purification (chloroform/methanol/water, 9:1:0 and then 6:4:0.5). $R_f$=0.50 (chloroform/methanol/water, 6:4:0.5). $[a]_D^{20}$=−3.0 (c 0.2, chloroform). $^1$H NMR (600 MHz, CDCl$_3$—CD$_3$OD, 1:1): d=0.89 (t, J=6.5 Hz, 18H, 6CH3), 1.25 (m, 114H, 57CH$_2$), 1.60 (m, 12H, 6CH$_2$), 2.30 (m, 6H, 3CH$_2$), 2.37-2.70 (m, 6H, 3CH$_2$), 3.03 (d, J=14.0 Hz, 0.5H), 3.13 (d, J=14.0 Hz, 0.5H), 3.24 (d, J=14.0 Hz, 0.5H), 3.27 (d, J=14.0 Hz, 0.5H), 3.29-3.36 (m, 2H), 3.45 (br s, 1H), 3.55-3.95 (m, 6H), 4.06-4.32 (m, 2H), 5.14-5.27 (m, 4H). ES-MS calcd. for $C_{95}H_{181}N_2O_{19}P$: 1685.3. found: 1686.3 (M+H), 1708.3 (M+Na), 1730.3 (M+2Na—H).

Example 16

Preparation of Compound 22

To Dipentaerythritol (2.0 g, 7.87 mmol) in dry DMF (10 mL) were added benzaldehyde dimethyl acetal (4.79 g, 4.7 ml, 31.46 mmol) and toluenesulfonic acid (150 mg, 0.78 mmol) and the mixture was stirred at 50° C. for 1 h. TLC (methanol:dichloromethane, 8:92) showed product and upper impurity, thought to be other —OH sites also substituted. To hydrolyze upper impurity, triethylamine (5 drops) was added to neutralize, DMF was evaporated under high vacuum, and methanol was added. The second TLC showed upper spot disappeared. The mixture was concentrated to clear syrup and purified by silica gel chromatography (methanol:dichloromethane, 5:95) to give 22 (1.91 g, 57%) as a mixture of three stereoisomerisms. TLC: $R_f$=0.38 (upper spot) and $R_f$=0.34 (lower spot) (7% methanol in dichloromethane). $^1$H NMR (500 MHz, CDCl$_3$) δ=3.21, 3.31, 3.39 (3 s, 4H); 3.28, 3.32, 3.46, 3.51 (4 br s, 2H, 2OH); 3.68, 3.69, 3.75 (3 d, J=12.0 Hz, 4H); 3.81, 3.92, 3.98 (3 s, 4H); 4.10 (m, 4H); 5.39, 5.41, 5.43 (3 s, 2H, 2CHPh), 7.38 (m, 6H, Ar—H); 7.50 (m, 4H, Ar—H). Through repeated chromatography (methanol/dichloromethane, gradient elution from 1% to 10%), the lower spot was separated to give a single component. $^1$H NMR (300 MHz, CDCl$_3$) for the lower spot: δ=2.50 (br s, 2H, 2OH), 3.45 (br s, 4H), 3.73 (d, J=12.0 Hz, 4H), 3.97 (s, 4H), 4.13 (d, J=12.0 Hz, 4H), 5.43 (s, 2H, 2CHPh), 7.37 (m, 6H, Ar—H), 7.49 (m, 4H, Ar—H).

Example 17

Preparation of Compound 23

Sodium hydride (0.426 g, 17.7 mmol) was added to dry DMF (35 ml) and cooled to 0° C. 22 (1.524 g, 3.54 mmol, dissolved in 15 ml DMF) was added drop wise and the mixture was stirred at 0° C. for 30 min for alkoxide formation. Drop wise added n-1-bromo-tetradecane (3.16 ml, 10.6 mmol, dissolved in 5 ml DMF) to mixture and stirred at room temperature for 16 hrs. TLC (hexane:ethyl acetate, 15:1) showed considerable amount of lower impurity thought to be mono-substitution of lipid arm. Another 2 equivalents of sodium hydride (0.21 g) and 2 equivalents of n-1-bromotetradecane (2.1 mL) were added and the mixture was stirred for 5 hrs at room temperature. More DMF (40 ml) was added to the slurry mixture and the reaction was continued for 16 hrs more at 50° C. Excessive NaH was quenched with water (3 ml) and the reaction mixture was neutralized with HCl (conc.). Evaporated off DMF, with co-evaporation with toluene (2×30 mL). The residue was dissolved in saturated sodium chloride (100 mL), extracted with dichloromethane (3×100 mL), and back-washed with saturated sodium chloride (30 mL). Dried with sodium sulfate and concentrated. The solid was purified by silica gel chromatography (hexane: ethyl acetate, 15:1) to give 23 (2.09 g, 72%). TLC indicated two spots, which were separated. The upper spot contains two components and the lower spot is a single compound.

23 (upper spot): TLC: $R_f$=0.43 (hexane:ethyl acetate, 15:1). $^1$H NMR (500 MHz, CDCl$_3$): δ=0.88 (t, J=6.5 Hz, 6H, 2CH$_3$); 1.26 (br s, 44H, 22CH$_2$); 1.54 (m, 4H, 2CH$_2$); 3.23, 3.24, 3.33 (3 s, 4H); 3.34, 3.37, 3.45 (3 t, J=6.5 Hz, 4H); 3.71, 3.72, 3.81 (3 s, 4H); 3.90 (m, 4H); 4.10 (m, 4H); 5.41, 5.43 (2 s, 2H, CHPh), 7.35 (m, 6H, Ar—H); 7.49 (m, 4H, Ar—H).

23 (lower spot): TLC: $R_f$=0.36 (hexane:ethyl acetate, 15:1). $^1$H NMR (500 MHz, CDCl$_3$): δ=0.88 (t, J=6.5 Hz, 6H, 2CH$_3$), 1.26 (br s, 44H, 22CH$_2$), 1.58 (m, 4H, 2CH$_2$), 3.23 (s, 4H), 3.47 (t, J=6.5 Hz, 4H, 2OCH$_2$CH$_2$), 3.72 (s, 4H), 3.87 (d, J=11.5 Hz, 4H), 4.11 (d, J=11.5 Hz, 4H), 5.43 (s, 2H, 2CHPh), 7.36 (m, 6H, Ar—H), 7.49 (m, 4H Ar—H).

Example 18

Preparation of Compound 24

To a solution of 23 (0.611 g, 0.742 mmol) in dry THF (20 mL) was added molecular sieves (4 Å, 2 g). The mixture was stirred at room temperature under nitrogen for 15 min. Sodium cyanoborohydride (0.932 g, 14.84 mmol) was added in portions and the mixture was cooled to 0° C. TFA (3.40 ml, 29.68 mmol) dissolved in THF (60 mL) was added drop wise slowly over 45 min. and allowed to stir at room temperature for 4 hrs. The mixture was filtered over celite and evaporated off THF under vacuum. The mixture was dissolved into saturated sodium bicarbonate solution (75 mL) and extracted with ethyl acetate (3×75 mL). The combined organic layers were washed with saturated sodium chloride solution (50 mL) and dried with sodium sulfate, and concentrated to yellow syrup. The syrup was purified by chromatography (gradient elution with hexane:ethyl acetate, 5:1 to 3:1) to give compound 24 (364 mg, 59%). TLC: $R_f$=0.19 (hexane:ethyl acetate, 4:1). $^1$H NMR (300 MHz, CDCl$_3$): δ=0.89 (t, J=6.5 Hz, 6H, 2CH$_3$), 1.27 (br s, 44H, 22CH$_2$), 1.52 (m, 4H, 2CH$_2$), 2.97 (br s, 2H, 2OH), 3.36 (t, J=6.5 Hz, 4H, 2OCH$_2$CH$_2$), 3.44 (s, 8H), 3.48 (s, 4H), 3.69 (br s, 4H), 4.49 (s, 4H, 2CH$_2$Ph), 7.30 (m, 10H, Ar—H).

Example 19

Preparation of Compound 25

To compound 24 (247 mg, 0.299 mmol) in dry dichloromethane (5 ml) were added 1H-tetrazole (0.136 g, 1.194 mmol) and dibenzyl diisopropylphosphoramidite (0.310 g, 0.3 ml, 0.896 mmol). The mixture was stirred at room temperature for 1 hour and the formation of complex checked with TLC (hexane:ethyl acetate, 4:1, showing 24 consumed). The mixture was then cooled to 0° C. and m-Chloroperbenzoic acid was added slowly resulting in gas formation. After 30 min, the mixture was poured into 10% sodium hydrogen sulfite (40 ml) and extracted with dichloromethane (3×40 ml). The organic layer was washed with saturated sodium bicarbonate solution (20 ml), dried with sodium sulfate and concentrated to yellow syrup. The syrup was purified by repeated chromatography (hexane:ethyl acetate, 3:1; hexane:acetone, 6:1) to give 25 (248 mg, 62%). TLC: $R_f$=0.21 (hexane:ethyl acetate, 2:1). $^1$H NMR (400 MHz, CDCl$_3$): δ=0.88 (t, J=6.5 Hz, 6H, 2CH$_3$), 1.22 (br s, 22H, 11CH$_2$), 1.24 (br s, 22H, 11CH$_2$), 1.44 (m, 4H, 2CH$_2$), 3.26 (t, J=6.5 Hz, 4H, 2OCH$_2$CH$_2$) 3.32 (s, 4H), 3.34 (s, 4H), 3.40 (s, 4H), 4.07 (d, J=3.5 Hz, 4H), 4.38 (s, 4H), 4.99 (d, J=8.0 Hz, 8H, 4CH$_2$Ph), 7.30 (m, 30H, Ar—H).

Example 20

Preparation of Compound 3

To a solution of 25 (150 mg, 0.111 mmol) in THF-HOAc (10:1, 90 mL) was added palladium on carbon (5%, 105 mg). The mixture was stirred at room temperature under hydrogen atmosphere for 16 hrs. TLC (chloroform:methanol:water: acetic acid, 4:1:0.1:0.1) indicated partial hydrogenation. Additional THF-HOAc (60 mL) and Pd/C (100 mg) were added to the mixture and allowed to stir at room temperature under hydrogen atmosphere over second night. TLC (chloroform:methanol:ammonium hydroxide:water, 1:1:8%:8%) indicated mostly product. The solid was filtered off and the filtrate concentrated under high vacuum. The residue was purified by chromatography (chloroform:methanol:ammonium hydroxide:water, 4:6:6%:6% to 1:1:8%:8%) to give 3 as ammonium salt. The product was re-dissolved in CHCl$_3$-MeOH—H$_2$O (1:1:8%) and passed through a small ion-exchange column (IR-120, Na$^+$ form) to give 3 (44 mg, 47%) as sodium salt. TLC: $R_f$=0.41 (chloroform:methanol:ammonium hydroxide:water, 1:1:8%:8%). ES-MS calculated for C$_{38}$H$_{80}$O$_{13}$P$_2$: 806.5. Found: 805.5 (M–H) and 827.5 (M+Na-2H) (negative mode). $^1$H NMR (600 MHz, CDCl$_3$+ CD$_3$OD, 1:1) for the sodium salt: δ=0.89 (t, J=6.5 Hz, 6H, 2CH$_3$), 1.27 (br s, 44H, 22CH$_2$), 1.54 (m, 4H, 2OCH$_2$CH$_2$), 3.35-3.43 (m, 8H), 3.45 (m, 1H), 3.50 (m, 2H), 3.53-3.59 (m, 3H), 3.66-3.71 (m, 2H), 3.77-3.83 (m, 4H). $^1$H NMR (500 MHz, CDCl$_3$+CD$_3$OD, 1:1) for the ammonium salt: δ=0.89 (t, J=7.0 Hz, 6H, 2CH$_3$), 1.27 (br s, 44H, 22CH$_2$), 1.55 (m, 4H, 2CH$_2$), 3.37-3.45 (m, 12H), 3.57-3.65 (m, 4H), 3.81-3.90 (m, 4H).

Example 21

Preparation of Compound 26

Compound 2 (9.50 g, 22.08 mmol) was dissolved in dry pyridine (57 mL). p-Toluenesulfonyl chloride (TsCl, 7.16 g, 37.54 mmol) was added at 0° C. to the reaction flask. The reaction was warmed to room temperature naturally and stirred overnight. Another portion of tosyl chloride (TsCl, 5.46 g) was added and the mixture was stirred at room temperature for 20 h. The solution was concentrated in vacuo. The residue was co-distilled with toluene. The crude product was dissolved in ethyl acetate (600 mL) and transferred to a separatory funnel. The organic layer was washed with saturated sodium bicarbonate solution (300 mL). The aqueous layer was back-washed with ethyl acetate (300 mL) and the combined organic layer was dried over sodium sulphate (Na$_2$SO$_4$) and concentrated. The residue was purified by silica gel chromatography (hexane:ethyl acetate, 3:1 and then 2:1) to give 26 (9.18 g, 59%). TLC: $R_f$=0.25 (hexane:ethyl acetate, 3:1). $^1$H NMR (400 MHz, CDCl$_3$): δ 2.41 (s, 3H, CH$_3$), 2.44 (s, 3H, CH$_3$), 3.27 (s, 2H), 3.70 (s, 2H), 3.73 (d, J=12.0 Hz, 2H), 3.80 (d, J=12.0 Hz, 2H), 3.87 (s, 2H), 3.93 (d, J=12.0 Hz, 2H), 4.00 (d, J=12.0 Hz, 2H), 4.32 (s, 2H), 5.30 (s, 2H, CHPh), 5.41 (s, 1H, CHPh), 7.28-7.48 (m, 14H, Ar—H), 7.81 (m, 4H, Ar—H).

Example 22

Preparation of Compound 27

Compound 26 (9.12 g, 12.91 mmol) was dissolved in toluene (150 mL). Saturated sodium bicarbonate (150 mL), phase transfer catalyst ALIQUAT™ (1 mL), and sodium azide (33.58 g, 516.47 mmol) were added to the reaction flask. The solution was heated to 110° C. and stirred overnight. More ALIQUAT™ (1 mL) and sodium azide (16.79 g) were added and the mixture was stirred at 110° C. for another 4 h. The reaction was incomplete. The solution was cooled to room temperature and usual aqueous work-up afforded syrup which was purified.

The filtrate was concentrated in vacuo. The residue was purified by silica gel chromatography (hexane:ethyl acetate, 5:1 and 4:1) to give 27 (2.58 g,) and the mono-azide substituted intermediate (3.73 g). The mono-azide substituted intermediate (3.73 g) was re-reacted in toluene (40 mL) with saturated sodium bicarbonate solution (40 mL), aliquat (1 mL), and sodium azide (16.34 g) at 110° C. for 7 days and more 27 (1.81 g) was obtained, resulting in the total yield of 71%. TLC: $R_f$=0.63 (hexane:ethyl acetate, 3:1). $^1$H NMR (400 MHz, CDCl$_3$) for one isomer: δ 3.30 (s, 4H), 3.78 (d, J=12.0 Hz, 4H), 3.90 (s, 4H), 4.10 (d, J=12.0 Hz, 4H), 5.40 (s, 2H, 2CHPh), 7.34-7.48 (m, 10H, Ar—H).

Example 23

Preparation of Compound 28

To diazido compound 27 (0.783 g, 1.629 mmol) in methanol (8 ml) were dropwise added 1,3-propane dithiol (3.27 mL, 32.586 mmol) and triethylamine (4.54 mL, 32.586 mmol) and the mixture was stirred overnight at room temperature. TLC (hexane:ethyl acetate, 2:1) showed reaction was complete. The reaction mixture was rotoevaporated and dithiol was co-evaporated with chloroform (3×20 mL). The residue was purified by flash chromatography to give 28 (0.322 g, 46% combined yield). TLC: $R_f$=0.29 (methanol:dichloromethane: water:ammonium hydroxide, 9:1.5:0.1:0.1). C$_{24}$H$_{32}$N$_2$O$_5$ (428.23). ES-MS (positive mode, m/z) found: 429 (M+H) $^1$H NMR (500 MHz, CDCl$_3$): δ 2.60 (s, 2H), 3.15 (s, 2H), 3.35 (s, 2H), 3.70 (d, J=12.0 Hz, 2H), 3.77 (s, 4H), 3.81 (d, J=12.0 Hz, 2H), 4.09 (d, J=12.0 Hz, 4H), 5.40 (s, 2H), 7.32-7.47 (m, 10H).

Example 24

Preparation of Compound 29

Compound 28 (0.160 g, 0.376 mmol) was dissolved in dry dichloromethane (10 mL). 1,3-Dicyclohexylcarbodiimide (DCC, 0.465 g, 2.254 mmol) and di-lipid acid 7 (0.513 g, 1.128 mmol) were added and the mixture was stirred at room temperature 60 h. TLCs (chloroform:methanol:water:ammonium hydroxide, 9:1.7:0.1:0.1; methanol:dichloromethane, 5:95; hexane:ethyl acetate, 3:1) showed reaction was complete. Excessive DCC was quenched with water (few drops) and stirred for 15 min. The reaction mixture was filtered through 2× Na$_2$SO$_4$ beds and the precipitate washed with dichloromethane. Rotoevaporated to a crude yellowish syrup. The syrup was purified by silica gel chromatography (hexane: ethyl acetate, 3:1) to give 29 (0.324 g, 66% yield). C$_{80}$H$_{136}$N$_2$O$_{11}$ (1301.01). ES-MS (positive mode, m/z) found: 1302 (M+H), 1324 (M+Na). $^1$H NMR (600 MHz, CDCl$_3$): δ 0.86 (t, J=6.5 Hz, 12H, 4CH$_3$), 1.25 (br s, 80H), 1.60 (m, 8H), 2.25 (m, 4H), 2.46 (m, 2H), 2.58 (m, 2H), 3.06 (s, 2H), 3.14 (m, 2H), 3.63 (m, 2H), 3.72-3.80 (m, 6H), 3.94-4.02 (m, 4H), 5.18 (m, 1H), 5.26 (m, 1H), 5.38 (s, 1H), 5.43 (s, 1H), 6.08 (t, J=7.0 Hz, 1H, H), 7.30-7.46 (m, 10H), 7.84 (t, J=6.5 Hz, 1H, NH).

Example 25

Preparation of Compound 30

To a solution of 29 (0.300 g, 0.229 mmol) in anhydrous THF (10 mL) was added molecular sieves (4 Å, 1 g), and sodium cyanoborohydride (0.287 g, 4.593 mmol). The mixture was stirred at 0° C. under nitrogen atmosphere for 15 minutes. Dropwise added ether-HCl(sat) until bubbling stopped (1-2 mL). TLC (hexane:ethyl acetate, 6:4) showed some mono-ring opening. Added another 20 equivalents (0.287 g) of sodium cyanoborohydride and dropwise added ether-HCl (2 mL). The mixture was filtered over celite and rotoevaporated off THF under high vacuum. The mixture was dissolved into saturated sodium bicarbonate solution (75 ml) and extracted with dichloromethane (3×75 ml). The combined organic layers were washed with saturated sodium chloride solution (50 ml) and dried with sodium sulfate, and concentrated to yellow syrup. The syrup was purified by silica gel chromatography (hexane:ethyl acetate, 6:4) to give compound 30 (0.212 g, 71%). TLC: $R_f$=0.17 (hexane:ethyl acetate, 6:4). C$_{80}$H$_{140}$N$_2$O$_{11}$ (1304.04). $^1$H NMR (300 MHz, CDCl$_3$): δ 0.88 (t, J=6.5 Hz, 12H, 4CH$_3$), 1.25 (br s, 80H), 1.60 (m, 8H), 1.94 (br s, 2H), 2.25 (m, 4H), 2.43 (m, 4H), 3.08 (m, 3H), 3.22 (m, 2H), 3.33 (m, 5H), 3.40-3.57 (m, 4H), 3.68 (m, 1H), 3.78 (m, 1H), 4.43 (d, J=12.0 Hz, 1H), 4.48 (s, 2H), 4.51 (d, J=12.0 Hz, 1H), 5.16 (m, 2H), 6.73 (m, 1H), 6.85 (m, 1H, NH), 7.30 (m, 10H).

Example 26

Preparation of Compound 31

To compound 30 (0.237 g, 0.181 mmol) in anhydrous dichloromethane (5 mL) was added tetrazole (0.076 g, 1.089 mmol) and dropwise-added dibenzyl diisopropyl phosphoramidite (0.250 g, 0.24 ml, 0.724 mmol). The mixture was stirred at room temperature for 1 hour and the formation of complex checked with TLC (hexane:ethyl acetate, 6:4). Added another 3 equivalents (0.038 g) of tetrazole and 2 equivalents (0.125 mg) of phosphoramidite. TLC after 2 hours showed the starting material was completely consumed. The mixture was then cooled to 0° C. and 3-chloroperbenzoic acid (0.312 g, 1.81 mmol) was added slowly resulting in gas formation. After 30 min, the mixture was poured into 10% sodium hydrogen sulfite (40 ml) and extracted with dichloromethane (3×40 ml). The organic layer was washed with saturated sodium bicarbonate solution (20 ml), dried with sodium sulfate and concentrated to a yellow syrup. The syrup was purified by repeated chromatography (hexane: ethyl acetate, 7:3; hexane:acetone, 4:1) to give 31 (198 mg, 60%). TLC: $R_f$=0.28 (hexane:ethyl acetate, 3:1). C$_{108}$H$_{166}$N$_2$O$_{17}$P$_2$ (1825.16). ES-MS (negative mode, m/z) found: 1861 (M+Cl). $^1$H NMR (500 MHz, CDCl$_3$): δ 0.88 (t, J=6.5 Hz, 12H, 4CH$_3$), 1.25 (br s, 80H), 1.55 (m, 8H), 2.21 (2 t, J=6.5 Hz, each 2H), 2.39 (m, 4H), 3.10 (m, 2H), 3.16 (m, 4H), 3.31 (m, 6H), 3.95 (m, 4H), 4.37 (m, 4H), 4.98 (m, 8H), 5.19 (m, 2H), 7.08 (t, J=6.0 Hz, 2H, 2NH), 7.22-7.31 (m, 30H).

Example 27

Preparation of Compound 4

To a solution of 31 (28 mg, 0.015 mmol) in distilled THF-AcOH (10:1, 75 mL) was added palladium on carbon (10%, 75 mg). The mixture was stirred at room temperature under hydrogen atmosphere for 16 hrs. TLC (chloroform:methanol: ammonium hydroxide:water, 2:3:0.5:0.5) indicated mostly product. The solid was gravity filtered and the filtrate concentrated under high vacuum. The residue was purified by flash chromatography using Iatrobeads as support (chloroform: methanol, 9:1 to chloroform:methanol:water, 5:3:0.3) to give 4 (18 mg, 95% yield) TLC: $R_f$=0.20 (chloroform:methanol: water, 4:2:0.3). $C_{66}H_{130}N_2O_{17}P_2$ (1284.88). ES-MS (negative mode, m/z) found: 1284 (M–H). $^1$H NMR (600 MHz, $CDCl_3$+$CD_3OD$, 1:1): δ 0.85 (t, J=6.5 Hz, 12H, 4CH$_3$), 1.28 (br s, 80H), 1.62 (m, 8H), 2.30 (m, 4H), 2.50-2.63 (m, 4H), 3.03-3.15 (m, 4H), 3.20-3.31 (m, 6H), 3.34-3.38 (m, 2H), 3.70-3.78 (m, 4H), 5.28 (m, 2H).

Example 28

Induction of Cytokine Secretion by Lipid A Analogs

Adherent cells isolated from human peripheral blood were incubated in complete RPMI-1640 medium in the presence of GM-CSF and IL-4. After three days of incubation, the lipid A analogs were added at a concentration of 10 μg/mL. After 24 hour of incubation, the supernatants were harvested and the presence of the cytokines was determined using ELISA kits. TNF-alpha, IL-6 and IL-8 levels were measured and listed in Table 1 (also see FIG. 14).

TABLE 1

In vitro cytokine secretion pattern of human adherent cells activated with synthetic lipid A mimic 1, 2, or R595 lipid A*.

|  | TNF-alpha (pg/mL) | IL-6 (pg/mL) | IL-8 (pg/mL) |
|---|---|---|---|
| 1 | 9723 | 21016 | 97980 |
| 2 | 4591 | 14097 | 72868 |
| R595 lipid A | 5490 | 19424 | 82612 |
| Medium | 263 | 17 | 99 |

*R595 lipid A is the natural lipid A product isolated from *Salmonella minnesota*, R595 (Avanti Polar Lipids, Inc.)

Example 29

Mice Immunized with Liposomal Vaccines

Groups of C57-Black mice were immunized subcutaneously with the BLP25 liposomal vaccine containing 0.2-200 μg of MUC1-based 25-mer lipopeptide as an antigen, which has the peptide sequence of H$_2$N-STAPPAHGVTSAPDTR-PAPGSTAPPK(Pal)G-OH, and 0.1-100 μg (half weight of the lipopeptide antigen) of lipid A analog per dose. Nine days after vaccine injection, mice were sacrificed and lymphocytes were taken from the draining lymph nodes (local response) or from the spleens (systemic response) to determine the immune response in each group. The lymphocytes taken from immunized mice were incubated in in vitro cultures in the presence of MUC1-based boosting antigen BP1-151, which has the peptide sequence H$_2$N-STAPPAHGVTSAPDTRPA-PGSTAPPK-OH.

Example 30

Measurement of T-Cell Proliferation

T-cell proliferation was evaluated using a standard $^3$H thymidine incorporation assay. Briefly, nylon wool passed inguinal lymph node lymphocytes from each mouse were added to a culture containing $10^6$ native mitomycin C treated syngeneic splenocytes, which serves as antigen presenting cells (APCs). To each well 20 μg of MUC1-based boosting peptide BP1-151, H$_2$N-STAPPAHGVTSAPDTRPAPG-STAPPK-OH, was added for positive control; and cultures containing no antigen or peptide BP1-72, which has the peptide sequence H$_2$N-EAIQPGCIGGPKGLPGLPGP-OH, were used as negative control. The culture was incubated for 72 h in a total volume of 250 μl/well, followed by adding 1 μCi of $^3$H-thymidine in a volume of 50 μl. The plates were incubated for an additional 18-20 h. Cells were harvested and [$^3$H]dTh incorporation was measured by liquid scintillation counter. T-cell proliferation results corresponding to various liposomal vaccines adjuvanted with lipid A mimic 1, 2, or R595 lipid A are shown in Table 2 and FIG. 15.

TABLE 2

Antigen specific T cell proliferation response after immunization of C57BL/6 mice with one dose of BLP25 liposomal vaccine. The dose contains 0.2 μg of 25-mer MUC1 based lipopeptide antigen and 0.1 μg of lipid A analog (1, 2, and R595 lipid A) as the adjuvant.

| Compound | CPM (counts per minute) | SD |
|---|---|---|
| 1 | 14831 | ±2475 |
| 2 | 20793 | ±2505 |
| R595 lipid A | 11920 | ±3630 |
| Saline | 320 | ±292 |

Example 31

Inhibition of Tumor Growth by Liposomal Vaccine Adjuvanted by Synthetic Lipid A Mimics C57BL/6 mice were challenged subcutaneously with MC38-MUC1 tumor cells on day 0. On day 7, 14, and 21, the groups of mice were immunized intradermally with BLP25 liposomal vaccine containing 200 μg/dose of MUC1 based 25-mer lipopeptide antigen and 100 μg/dose of synthetic lipid A mimic 1, 2, or R595 lipid A. On day 34, the tumor diameters (length and width) were taken with a caliper and tumor size ware expressed in mm$^2$ (length×width). The data is shown in Table 3 and FIG. 16.

TABLE 3

Active specific immunotherapy of MC-38 MUC1 tumor bearing mice immunized intradermally with BLP25 liposomal vaccine containing lipid A analogs (1, 2, and R595 lipid A). The vaccine dose contains 200 μg of BLP25 lipopeptide and 100 μg of lipid A analog as adjuvant.

| Compound | Tumor size (mm$^2$) |
|---|---|
| 1 | 284 |
| 2 | 298 |
| R595 lipid A | 287 |
| Saline | 539 |

REFERENCES

Aguilera, Begona; Romero-Ramírez, Lorenzo; Abad-Rodríguez, José; Corrales, Guillermo; Nieto-Sampedro, Manuel; Fermández-Mayoralas, Alfonso. *J. Med. Chem.* 1998, 41, 4599-4606.

Armspach, Dominique; Cattalini, Marco; Constable, Edwin C.; Housecroft, Catherine E.; Phillips, David. Boron-rich Metallodendrimers—Mix-and-match Assembly of Multifunctional Metallosuperomolecules, *Chem. Commun.* 1996, 1823-1824.

Cheng, Xiao Hong; Diele, Siegmar; Tschierske, Carsten. Molecular Design of Liquid-Crystalline Block Molecules: Semifluorinated Pentaerythritol Tetrabenzoates Exhibiting Lamellar, Columnar, and Cubic Mesophases, *Angew. Chem. Int. Ed.* 2000, 39, 592-595.

Christ, W. J.; Asano O.; Robidoux, A. L. C.; Perez, M.; Wang, Y.; Dubuc, G. R.; Gavin, W. E.; Hawkins, L. D.; McGuinness, P. D.; Mullarkey, M.; Lewis, M. D.; Kishi, Y.; Kawata, T.; Bristol, J. R.; Rose, J. R.; Rossignol, D. P.; Kobayashi, S.; Hishinuma, I.; Kimura, A.; Asakawa, N.; Karayama, K.; Yamatsu, I. *Science,* 1995, 268, 80-83.

Dunn, T. Jeffrey; Neumann, William L.; Gogic, Milorad M.; Woulfe, Steven R. Versatile Methods for the Synthesis of Differentially Functionalized Pentaerythritol Amine Derivatives, *J. Org. Chem.* 1990, 55, 6368-6373.

Farcy, Nadia; Muynck, Hilde De; Madder, Annemieke; Hosten, Noel; Clercq, Pierre J. De. A Pentaerythritol-Based Molecular Scaffold for Solid-Phase Combinatorial Chemistry, *Org. Lett.* 2001, 3, 4299-4301.

Hawkins, L. D.; Ishizaka, S. T.; McGuinness, P.; Zhang, H.; Gavin, W.; DeCosta, B.; Meng, Z.; Yang, H.; Mullarkey, M.; Young, D. W.; Yang, H.; Rossignol, D. P.; Nault, A.; Rose, J.; Przetak, M.; Chow, J. C.; Gusovsky, F. *J. Pharmacol. Exp. Ther.* 2002, 300, 655-661.

Imoto, M.; S. Kusumoto, T. Shiba, E. T. Rietschel, C. Galanos, and O. Lüderitz, *Tetrahedron Lett.* 1985, 26, 907-908.

Johnson, D. A.; Sowell, C. G.; Johnson, C. L.; Livesay, M. T.; Keegan, D. S.; Rhodes, M. J.; Ulrich, J. T.; Ward, J. R.; Cantrell, J. L.; Brookshire, V. G. *Bioorg. Med. Chem. Lett.* 1999, 9, 2273-2278.

Kotani, S. et al, *Infect. Immun.* 1986, 52(3), 872-884. Kuzdzal, Scott A.; Monnig, Curtis A.; Newkome, George R.; Moorefield, Charles N. Dendrimer Electrokinetic Capillary Chromatography: Unimolecular Micellar Behaviour of Carboxylic Acid Terminated Cascade Macromolecules, *J. Chem. Soc., Chem. Commun.* 1994, 2139-2140.

Kutuzova, G. D.; Albrecht, R. M.; Erickson, C. M.; Qureshi, N. *J. Immunol.* 2001, 167, 482-489.

Lien, E.; Chow, J. C.; Hawkins, L. D.; McGuinness, P. D.; Miyake, K.; Espeviks, T.; Gusovsky, F.; Golenbock, D. T. *J. Biol. Chem.* 2001, 276, 1873-1880.

Nantz, Michael H.; Nberle, Alfred M. Pentaerythritol Lipid Derivatives and Nucleic-Acid Complexes, U.S. Pat. No. 6,316,421, 2001. Ranganathan, Darshan; Samant, Manoj P.; Karle, Isabella L. Self-Assembling, Cystine-Derived, Fused Nanotubes based on Spirane Architecture: Design, Synthesis, and Crystal Structure of Cystinospiranes., *J. Am. Chem. Soc.* 2001, 123, 5619-5624.

Rietschel, E. T.; Brade, H.; Holst, O.; Brade, L.; Müller-Loennies, S.; Mamat, U.; Zähringer, U.; Beckmann, R.; Seydel, U.; Brandenburg, K.; Ulmer, A. J.; Mattern, T.; Heine, H.; Schletter, J.; Hauschildt, S.; Loppnow, H.; Schönbeck, U.; Flad, H.-D.; Schade, U. F.; Di Padova, F.; Kusumoto, S.; Schumann, R. R. *Curr. Top. Microbiol. Immunol.* 1996, 216, 39.

Schromm, A. B.; Brandenburg, K.; Loppnow, H.; Moran, A. P.; Koch, M. H. J.; Rietschel, E. T.; Seydel, U. *Eur. J. Biochem.* 2000, 267, 2008.

Seydel, U.; Oikawa, M.; Fukase, K.; Kusumoto, S.; Brendenburg, K. *Eur. J. Biochem.* 2000, 267, 3032.

Seydel, U.; B. Lindner, H.-W. Wollenveber, and E. T. Rietschel, *Eur. J. Biochem.* 1984, 145, 505-509.

Takada, H.; Kotani, S. *CRC Critic. Rev. Microbiol.* 1989, 16, 477-523.

Toepfer, Alexander; Kretzschmar, Gerhard; Bartnik, Eckart. *Tetrahedron Lett.* 1995, 36, 9161-9164.

Toepfer, Alexander; Kretzschmar, Gerhard; Bartnik, Eckart; Seiffge, Dirk. U.S. Pat. No. 6,136,790, 2000.

Wörl, Ralf; Köster, Hubert. Synthesis of New Liquid Phase Carriers for Use in Large Scale Oligonucleotide Synthesis in Solution, *Tetrahedron,* 1999, 2941-2956.

Zuany-Amorim, C.; Hastewell, J.; Walker, C. *Nat. Rev. Drug Discovery* 2002, 1, 797-807.

Stryer, *Biochemistry,* $2^{nd}$ Ed. W. H. Freeman and Co., New York, p74, 1981.

Christian H. R. Raetz, International Patent, WO 86/05687, 1986.

E. Th. Rietschel, L. Brade, B. Lindner, and U. Zahringer, 1992. Biochemistry of lipopolysaccharides. In: pp. 3-41, D. C. Morrison and J. L. Ryan (eds.), Bacterial Endotoxic Lipopolysaccharides, Volume I, Molecular Biochemistry and Cellular Biology, CRC Press, Boca Raton, Ann Arbor, London, Tokyo.

H. Takada and S Kotani, 1992. Structure-function relationships of Lipid-A. In: pp. 107-134. ibid M. Imoto, S. Kusumoto, T. Shiba, E. T. Rietschel, C. Galanos, and O. Lüderitz, *Tetrahedron Lett.* 1985, 26, 907-908. (1985a)

M. Imoto, H. Yoshimura, N. Sakaguchi, S. Kusumoto, T. Shiba, *Tetrahedron Lett.* 1985, 26, 1545-1548. (1985b)

E. T. Rietschel, H.-W. Wollenweber, H. Brade, U. Zähringer, B. Lindner, U. Seydel, H. Bradaczek, G. Barnickel, H. Labishinski, and P. Giesbrecht. 1984. Structure and conformation of the lipid A component of lipopolysaccharides, pp. 187-220. In E. R. Rietschel (ed.), Handbook of Endotoxin, vol. 1. Chemistry of endotoxin. Elsevier Science Publishers, Amsterdam. (1984a)

E. T. Rietschel, H.-W. Wollenweber, R. Russa, H. Brade, and U. Zähringer. *Rev. Infect. Dis.* 1984, 6, 432-438. (1984b)

U. Seydel, B. Lindner, H.-W. Wollenweber, and E. T. Rietschel, *Eur. J. Biochem.* 1984, 145, 505-509.

S. M. Strain, I. M. Armitage, L. Anderson, K. Takayama, N. Qureshi, and C. R. H. Raetz. *J. Biol. Chem.* 1985, 260, 16089-16098.

H. Takada, S Kotani, *CRC Critic. Rev. Microbiol.* 1989, 16, 477-523.

E. Ribi, K. Amano, J. L. Cantrell, S. M. Schwartzman, R. Parker and K. Takayama, *Cancer Immunol. Immunother.* 1982, 12, 91-96.

S. Kotani et al, *Infect. Immun.* 1986, 52(3), 872-884. (1986a)

S. Kotani et al, *Infect. Immun.* 1986, 54, 673. (1986b)

M. Kiso, S. Tanaka, M. Tanahashi, Y. Fujishima, Y. Ogawa, and A. Hasagawa, *Carbohr. Res.* 1986, 148, 221.

Y. Fujishima, K. Kigawa, Y. Ogawa, M. Kiso, A. Hasagawa, *Carbohydr. Res.* 1987, 167, 317.

D. Charon, R. Chaby, A. Malinvaud, M. Mondange, and L. Szabó, *Biochemistry,* 1985, 24, 2736.

W. J. Christ et al, *Science,* 1995, 268, 80-83.

K. Sato et al, *Infect. Immun.* 1995, 63, 2859-2866.

Georges H. Werner and Pierre Jollès, *Eur. J. Biochem,* 1996, 242, 1-19.

K. Takayama, N. Qureshi, E. Ribi, and J. L. Cantrell, *Rev. Infect. Dis.* 1984, 6, 439-443.

Keat R. Myers, Alex T. Trachet, U.S. Pat. No. 4,912,094, 1990.

J. T. Ulrich and K. R. Myers, *Pharm. Biotechnol.* 1995, 6, 495-524.

Martti Vaara, *Science,* 1996, 274 (8), 939-940.

H. Russell Onishi, Barbara A. Pelak, Lynn S, Gerckens, Lynn L. Silver, Frederick M. Kahan, Meng-Hsin Chen, Arthur A. Patchett, Susan M. Galloway, Sheryl A. Hyland, Matt S. Anderson, Christian R. H. Raetz, *Science,* 1996, 274 (8), 980-982.

R. C. Goldman, J. O. Capoblanco, C. C. Doran, and A. G. Matthysse. *J. Gen. Microbiol.* 1992, 138:1527-1533.

R. C. Goldman, C. C. Doran, J. O. Capoblanco. *J. Bacterial.* 1988, 170: 2185-2192.

K. Takayama, N. Qureshi, E. Ribi, J. L. Cannell, and K. Amano. 1983. Use of endotoxin in cancer immunotherapy and characterization of its nontoxic but active lipid A components. In: pp. 219-233. L. Anderson and F. M. Unger (eds.), Bacterial lipopolysaccharides, American Chemical Society, Washington, D.C. K. Von Esehen. 1992. Monophosphoryl lipid A and immunotherapy. In: D. C. Morrison and J. L. Ryan (eds.), Bacterial Endotoxic Lipopolysaccharides, Volume II, Immunopharmacology and pathophysiology, CRC Press, Boca Raton, Ann Arbor, London, Tokyo.

M. P. Fink, *Crit. Care Med.* 1993, 21 Suppl.: S32-S39.

W. J. Christ, T. Kawata, L. D. Hawkins, S, Kobayashi, O. Asano, and D. P. Rossignol. European patent EP-536969-A2. Dement Publications. Ltd.

The invention claimed is:

1. A compound which is a lipid A analog of the structure (I)

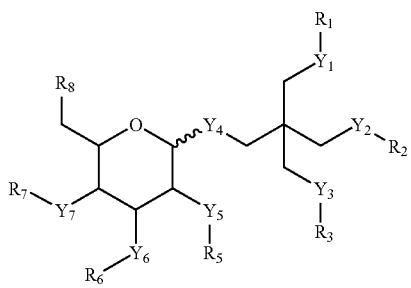

wherein at least one of $R_1$, $R_2$, $R_3$, $R_5$, $R_6$, and $R_7$ is a strongly lipophilic group selected from the group consisting of

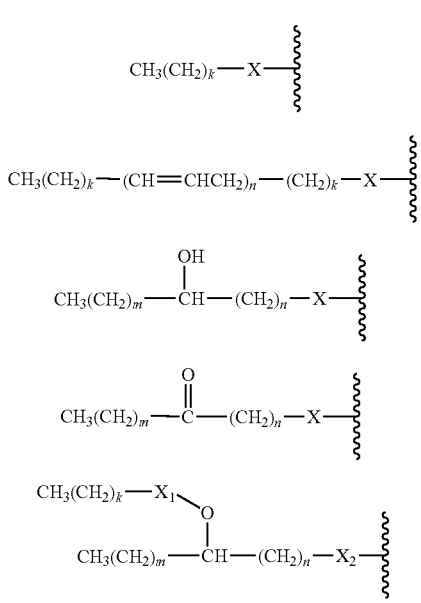

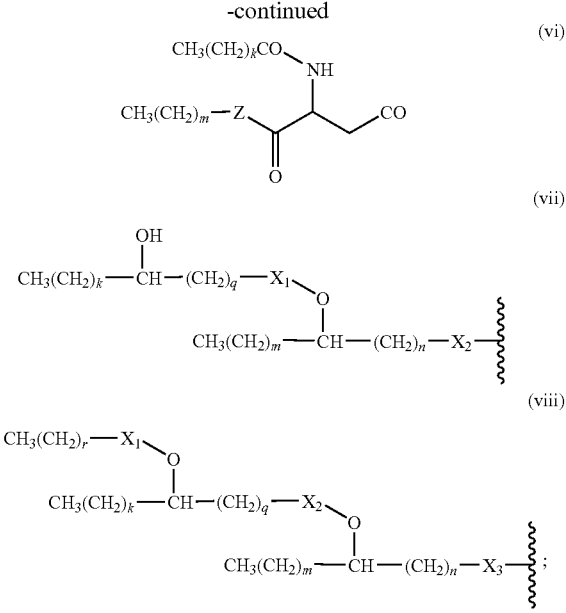

wherein X, $X_1$, $X_2$, and $X_3$ are independently —CO— or —CH$_2$—; Z is —NH— or —O—; k, m, and r are independently an integer of 0 to 30 inclusive, n and q are independently an integer of 0 to 6 inclusive;

wherein Y4 is a spacer selected from the group consisting of —O—, —S—, and —NH— wherein, at least one of $Y_1R_1$, $Y_2R_2$, $Y_3R_3$, $Y_5R_5$, $Y_6R_6$ and $Y_7R_7$ is a monovalent phosphate equivalent (MPE), wherein each monovalent phosphate equivalent is, independently, (a) —R'—C(O)OH, where R' is a substituted or unsubstituted alkyl group of 1-4 carbons, or (b) selected independently from the group consisting of —OB(OH)OR, —OP(O)(OH)OR, —OS(O)(O)(OH)OR, and —OP(=O)(OH)—O—P(=O)(OH)OR, where R is hydrogen, or a substituted or unsubstituted alkyl group of 1-4 carbons, and if R is a substituted alkyl group, the substitutions are —OH or —NH$_2$, wherein $R_8$ is selected from the group consisting of H, OH, OR$_9$, a moiety which in combination with $Y_8$ forms a monovalent phosphate equivalent as previously defined, and a group (i)-(viii) as defined above; wherein $R_9$ is an alkyl or acyl group of 1 to 10 carbon length; and wherein the glycosidic linkage is α or β;

or a compound which is a lipid A analogue of the structure (II)

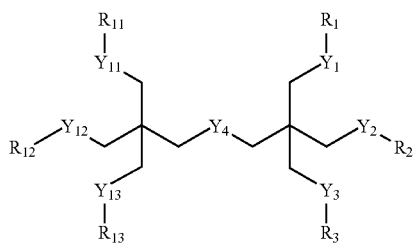

wherein at least one of $R_1$, $R_2$, $R_3$, $R_{11}$, $R_{12}$ and $R_{13}$ is a strongly lipophilic group selected from the group consisting of (i)-(viii) above;

wherein Y4 is a spacer selected from the group consisting of —O—, —S—, and —NH— and wherein, at least one of $Y_1R_1, Y_2R_2, Y_3R_3, Y_{11}R_{11}, Y_{12}R_{12}$ and $Y_{13}R_{13}$ is independently a monovalent phosphate equivalent as previously defined;

wherein the following limitations apply to both (I) and (II) above:

$Y_1, Y_2, Y_3, Y_5, Y_6, Y_7, Y_{11}, Y_{12}$ and $Y_{13}$ are spacers independently selected from the group consisting of —O—, —S—, and —NH—;

$R_1, R_2, R_3, R_5, R_6, R_7, R_{11}, R_{12}$ and $R_{13}$ are independently hydrogen, a moiety which with the commonly numbered Y group forms monovalent phosphate equivalent as previously defined, or a strongly lipophilic group selected from the group consisting of (i)-(viii) above, the strongly lipophilic groups of said compound collectively provide at least two major carbon chains, and the major carbon chains of said strongly lipophilic groups collectively provide at least 30 carbon atoms;

or which compound is a pharmaceutically acceptable salt of (I) or (II).

2. The compound of claim 1 in which the compound is of structure (I), or is a pharmaceutically acceptable salt thereof.

3. The compound of claim 1 in which the compound is of structure (II), or is a pharmaceutically acceptable salt thereof.

4. The compound of 1 wherein Y4 is —O—.

5. The compound of claim 2 wherein Y4 is —O—.

6. The compound of claim 3 wherein Y4 is —O—.

7. The compound of claim 5 wherein at least one strongly lipophilic group satisfies (i) and for at least one such group, k is an integer 4-30.

8. The compound of claim 5 wherein at least one strongly lipophilic group satisfies (ii), and for at least one such group, and 2k+3n is an integer 4-30.

9. The compound of claim 5 wherein at least one strongly lipophilic group satisfies (iii), and for at least one such group, and m+n+1 is 4-30.

10. The compound of claim 5 wherein at least one strongly lipophilic group satisfies (iv), and for at least one such group, m+n+1 is 4-30.

11. The compound of claim 5 wherein at least one strongly lipophilic group satisfies (v), and for at least one such group, m+n+k+1 is 4-30.

12. The compound of claim 5 wherein at least one strongly lipophilic group satisfies (vi), and for at least one such group, k+m+2 is 4-30.

13. The compound of claim 5 wherein at least one strongly lipophilic group satisfies (vii), and for at least one such group, k+q+m+n is 4-30.

14. The compound of claim 5 wherein at least one strongly lipophilic group satisfies (viii), and for at least one such group, r+k+q+m+n is 5-30.

15. The compound of claim 1, wherein $Y_1, Y_2, Y_3, Y_4, Y_5, Y_6, Y_7, Y_{11}, Y_{12}$ and $Y_{13}$ are independently —O— or —NH—.

16. The compound of claim 2, wherein $Y_1, Y_2, Y_3, Y_4, Y_5, Y_6$ and $Y_7$ are independently consisting of —O— or —NH—.

17. The compound of claim 3, wherein $Y_1, Y_2, Y_3, Y_4, Y_{11}, Y_{12}, Y_{13}$ are independently —O— or —NH—.

18. The compound of claim 16 wherein Y4 is —O—.

19. The compound of claim 1 wherein each monophosphate equivalent is —OP(O)(OH)(OH).

20. The compound of claim 2 wherein each monophosphate equivalent is —OP(O)(OH)(OH).

21. The compound of claim 3 wherein each monophosphate equivalent is —OP(O)(OH)(OH).

22. The compound of claim 5 wherein each monophosphate equivalent is —OP(O)(OH)(OH).

23. The compound of claim 18 wherein each monophosphate equivalent is —OP(O)(OH)(OH).

24. The compound of claim 2, wherein

Y4 is —O—;

$Y_1, Y_2$, and $Y_7$ are —O—;

$Y_3, Y_5$ and $Y_6$ are independently —O— or —NH—;

$R_1, R_3, R_5$ and $R_6$ are independently hydrogen or a strongly lipophilic group selected from (i)-(viii);

at least one of $R_1, R_3, R_5$ and $R_6$ is not hydrogen;

$R_2$ and $R_7$ are independently selected from the group consisting of H, —P(O)(OH)$_2$, —SO$_3$H, —P(O)(OH)(OCH$_2$CH$_2$NH$_2$), and —CH$_2$COOH; and $R_8$ is selected from the group consisting of H, OH, OSO$_3$H, and OR$_9$ wherein $R_9$ is an alkyl or acyl group of 1 to 10 carbon length.

25. The compound of claim 3, wherein

Y4 is —O—, $Y_2$ and $Y_{12}$ are —O—, $Y_1, Y_3, Y_{11}$, and $Y_{13}$ are independently chosen from the group consisting of —O—, —NH— and —S—;

$R_1, R_3, R_{11}$, and $R_{13}$ are independently hydrogen, or a strongly lipophilic group selected from (i)-(viii);

at least one of $R_1, R_3, R_5$, and $R_6$ is not hydrogen; and $R_2$ and $R_{12}$ are independently selected from the group consisting of H, —P(O)(OH)$_2$, —P(O)(OH)(OCH$_2$CH$_2$NH$_2$), and —CH$_2$COOH.

26. The compound of claim 2 wherein $R_1, R_3, R_5$ and $R_6$ are independently hydrogen or a strongly lipophilic group selected from the group consisting of (i)-(viii), at least one $R_1, R_3, R_5$ and $R_6$ is not hydrogen, and $R_2$ and $R_7$ are independently selected from the group consisting of H, —P(O)(OH)$_2$, —SO$_3$H, —P(O)(OH)(OCH$_2$CH$_2$NH$_2$), and —CH$_2$COOH; and $R_8$ is selected from the group consisting of H, OH, OSO$_3$H, and OR$_9$ wherein $R_9$ is an alkyl or acyl group of 1 to 10 carbon length.

27. The compound of claim 3 wherein $R_1, R_3, R_{11}$, and $R_{13}$ are independently hydrogen, or a strongly lipophilic group selected from (i)-(viii); at least one of $R_1, R_3, R_5$ and $R_6$ is not hydrogen; and $R_2$ and $R_{12}$ are independently selected from the group consisting of H, —P(O)(OH)$_2$, —SO$_3$H, —P(O)(OH)(OCH$_2$CH$_2$NH$_2$), and —CH$_2$COOH.

28. The compound of claim 24 wherein each monophosphate equivalent is —OP(O)(OH)(OH).

29. The compound of claim 25 wherein each monophosphate equivalent is —OP(O)(OH)(OH).

30. The compound of claim 2, wherein the strongly lipophilic groups of said compound collectively provide at least three major carbon chains, and wherein the major carbon chains of said strongly lipophilic groups collectively provide at least 40 carbon atoms, said compound having immunostimulatory activity.

31. The compound of claim 2 wherein the strongly lipophilic groups of said compound collectively provide at least four major carbon chains and wherein the major carbon chains collectively provide at least 50 carbon atoms, said compound having immunostimulatory activity.

32. The compound of claim 30, wherein the strongly lipophilic groups collectively provide six major carbon chains.

33. The compound of claim 32 wherein each major carbon chain is characterized by 10, 12, 14, 16, 18 or 20 carbon atoms in said chain.

34. A method of stimulating the immune system of a mammalian subject which comprises administering to said subject an immunostimulatory amount of the compound of claim 30.

35. A method of stimulating the immune system of a mammalian subject which comprises administering to said subject an immunostimulatory amount of the compound of claim 31.

36. A method of stimulating the immune system of a mammalian subject which comprises administering to said subject an immunostimulatory amount of the compound of claim 32.

37. A method of stimulating the immune system of a mammalian subject which comprises administering to said subject an immunostimulatory amount of the compound of claim 33.

38. A method of stimulating the immune system of a mammalian subject which comprises administering to said subject an immunostimulatory amount of the compound of claim 34, said compound having immunostimulatory activity.

39. A method of inhibiting an adverse lipid A activity in a mammalian subject which comprises administering to said subject an inhibitory amount of the compound of claim 34, said compound having lipid A antagonist activity.

40. The compound of claim 24 wherein $Y_3$ and $Y_5$ are —NH— and $Y_6$ is —O—.

41. The compound of claim 24 wherein $R_3$, $R_5$ and $R_6$ are strongly lipophilic groups according to (v), with independently chosen values for k, $X_1$, m, n, and $X_2$.

42. The compound of claim 41 wherein k and m for $R_3$, $R_5$ and $R_6$ are independently 8-18.

43. The compound of claim 24 wherein $X_1$ is —CO—, $X_2$ is —CO— and n=1.

44. The compound of claim 24 wherein k and m are independently 8, 10, 12, 14, 16 or 18.

45. The compound of claim 26 wherein k and m are 12.

46. The compound of claim 24 wherein $R_8$ is OH.

47. The compound of claim 24 wherein $Y_7$ is —O— and $R_7$ is —P(=O)(OH)(OH).

48. The compound of claim 47 wherein $Y_2$ is —O— and $R_2$ is H.

49. The compound of claim 40 wherein $Y_2$ is —O— and $R_2$ is —P(=O)(OH)(OH).

50. The compound of claim 1 where R1-R3 are hydrogen.

51. The compound of claim 50 in which Y1-Y3 are —O— and R1-R3 are hydrogen.

52. The compound of claim 50 in which R1-R3 are hydrogen, and two of Y1-Y3 are —O— and the other is —NH—.

53. The compound of claim 1 where two of R1-R3 are hydrogen.

54. The compound of claim 53 where two of —Y1R1, —Y2R2, and —Y3R3 are —OH.

55. The compound of claim 53 where one of —Y1R1, —Y2R2, and Y3R3 is —OH and one of —Y1R1, —Y2R2, and Y3R3 is —NH$_2$.

56. The compound of claim 1 where one of R1-R4 is hydrogen.

57. The compound of claim 1 where none of R1-R3 is hydrogen.

58. The compound of claim 1 in which one of R1-R3 is a strongly lipophilic group.

59. The compound of claim 1 in which at least two of R1-R3 comprise strongly lipophilic groups.

60. The compound of claim 59 in which two of R1-R3 are strongly lipophilic groups.

61. The compound of claim 1 in which three of R1-R4 are strongly lipophilic groups.

62. The compound of claim 3 where each of spacers Y1-Y4 and Y11-Y13 is —O—.

63. The compound of claim 1 where three of spacers Y1-Y4 are —O— and the remaining spacer is —NH—.

64. The compound of claim 1 which provides one phosphate equivalent.

65. The compound of claim 1 which provides two phosphate equivalents.

66. The compound of claim 1 where (b) applies and R is hydroxyl.

67. The compound of claim 1 where (b) applies and said phosphate-equivalent comprises —OP(=O)(OH)O—.

68. The compound of claim 1 where (b) applies and R is a substituted or unsubstituted alkyl group of 1-4 carbons.

69. The compound of claim 1 where R is $CH_2CH_2NH_2$.

70. The compound of claim 1 where (a) applies.

71. The compound of claim 70 where R' is —CH$_2$—.

72. The compound of claim 2 in which the sugar is an amino sugar.

73. The compound of claim 72 in which the sugar is a glucosamine.

74. The compound of claim 2 in which at least one phosphate equivalent is $Y_5R_5$, $Y_6R_6$, $Y_7R_7$ or $Y_8R_8$.

75. The compound of claim 74 in which at least one phosphate equivalent is connected to said sugar unit.

76. The compound of claim 2 in which at least one phosphate equivalent is $Y_1R_1$, $Y_2R_2$ or $Y_3R_3$.

77. The compound of claim 2 in which at least one of R5-R8 comprises a strongly lipophilic group.

78. The compound of claim 2 in which two or more of R5-R7 comprises a strongly lipophilic group.

79. The compound of claim 1 where at least one strongly lipophilic group comprises only one major carbon chain.

80. The compound of claim 1 where at least one strongly lipophilic group comprises only two major carbon chains.

81. The compound of claim 1 where at least one strongly lipophilic group comprises only three major carbon chains.

82. The compound of claim 1 where its strongly lipophilic groups collectively provide three major carbon chains.

83. The compound of claim 1 where its strongly lipophilic groups collectively provide four major carbon chains.

84. The compound of claim 1 where its strongly lipophilic groups collectively provide five major carbon chains.

85. The compound of claim 1 where its strongly lipophilic groups collectively provide six major carbon chains.

86. The compound of claim 1 where its strongly lipophilic groups collectively provide seven major carbon chains.

87. The compound of claim 1 where its strongly lipophilic groups collectively provide eight major carbon chains.

88. The compound of claim 1 where each major carbon chain is 10-20 carbons.

89. The compound of claim 88 where each major carbon chain is 12-16 carbons.

90. The compound of claim 1 where the major carbon chains of the strongly lipophilic groups collectively provide at least 40 carbon atoms.

91. The compound of claim 1 where the major carbon chains of the strongly lipophilic groups collectively provide at least 50 carbon atoms.

92. The compound of claim 1 where the major carbon chains of the strongly lipophilic groups collectively provide at least 60 carbon atoms.

93. The compound of claim 1 where the major carbon chains of the strongly lipophilic groups collectively provide at least 70 carbon atoms.

94. The compound of claim 1 where the major carbon chains of the strongly lipophilic groups collectively provide at least 80 carbon atoms.

95. The compound of claim 1 where the major carbon chains of the strongly lipophilic groups collectively provide at least 90 carbon atoms.

96. The compound of claim 1 where the major carbon chains of the strongly lipophilic groups collectively provide not more than 90 carbon atoms.

97. The compound of claim 1 where the major carbon chains of the strongly lipophilic groups collectively provide not more than 80 carbon atoms.

98. The compound of claim 1 where the major carbon chains of the strongly lipophilic groups collectively provide not more than 70 carbon atoms.

99. The compound of claim 1 where the major carbon chains of the strongly lipophilic groups collectively provide not more than 60 carbon atoms.

100. The compound of claim 1 where at least one strongly lipophilic group is selected from the group consisting of

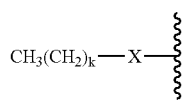

(i)

where X is —CO— or —CH$_2$—, k is an integer 4-30;

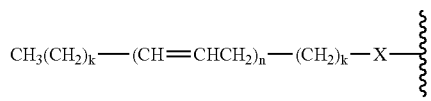

(ii)

where n is an integer 0-6, k is an integer 0-30 and 2k+3n is an integer 4-30;

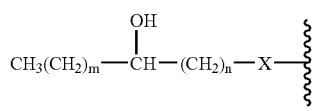

(iii)

where m and n are integers (0-6 for n and 0-30 for m), and m+n+1 is 4-30;

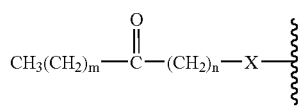

(iv)

where m+n+1 is 4-30;

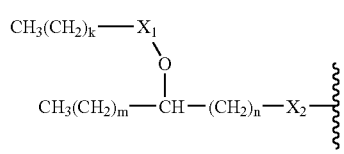

(v)

where X$_1$ and X$_2$ are independently —CO— or —CH$_2$—, and m+n+k+1 is 4-30;

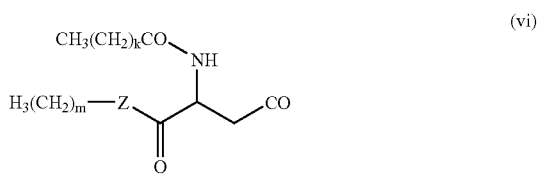

(vi)

where Z is —NH— or —O—, and k+m+2 is 4-30;

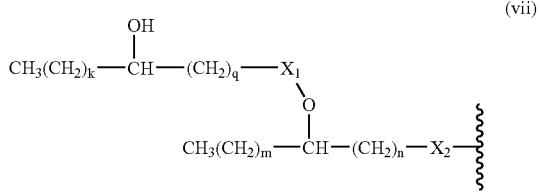

(vii)

where q is an integer 0-6, and k+q+m+n is 4-30; and

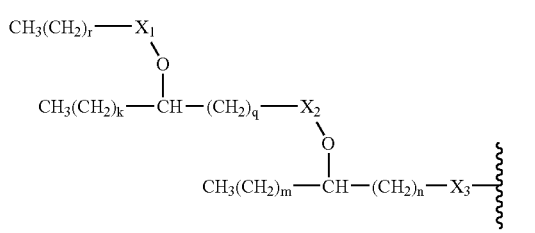

(viii)

where X$_1$, X$_2$, and X$_3$ are independently —CO— or —CH$_2$—, r is an integer 0-6, and r+k+q+m+n is 5-30.

101. The compound of claim 100 where all of the strongly lipophilic groups are selected from the group consisting of structures (i)-(viii).

102. The compound of claim 1 where at least one strongly lipophilic group is structure (i).

103. The compound of claim 1 where at least one strongly lipophilic group is structure (ii).

104. The compound of claim 1 where at least one strongly lipophilic group is structure (iii).

105. The compound of claim 1 where at least one strongly lipophilic group is structure (iv).

106. The compound of claim 1 where at least one strongly lipophilic group is structure (v).

107. The compound of claim 1 where at least one strongly lipophilic group is structure (vi).

108. The compound of claim 1 where at least one strongly lipophilic group is structure (vii).

109. The compound of claim 1 where at least one strongly lipophilic group is structure (viii).

110. The compound of claim 1 where at least one strongly lipophilic group is one of the structures set forth below

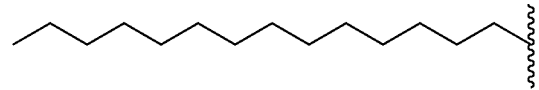

-continued

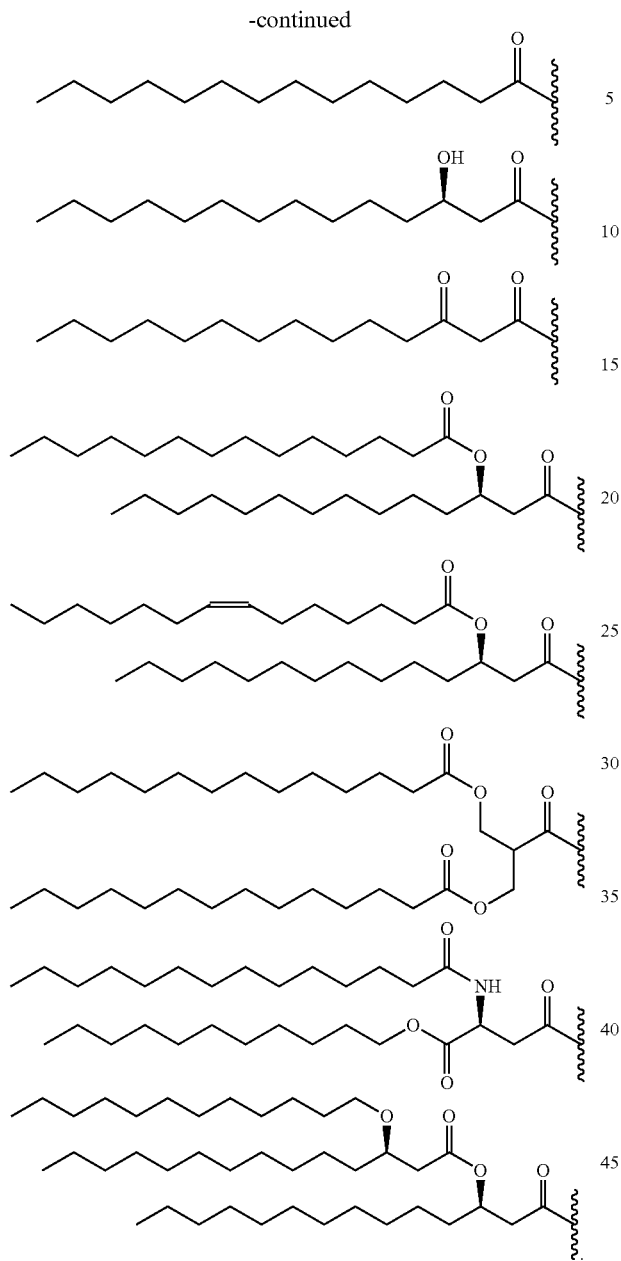

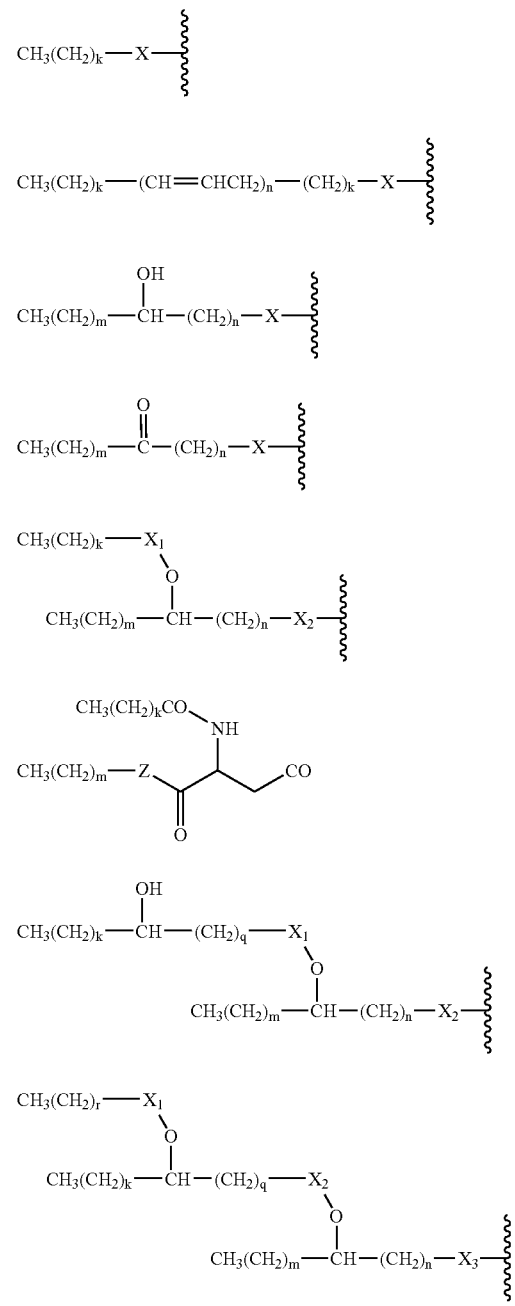

111. The compound of claim 110 where each strongly lipophilic group is independently one of the structures set forth in claim 116.

112. The compound of claim 24 where the structure is further defined as the following

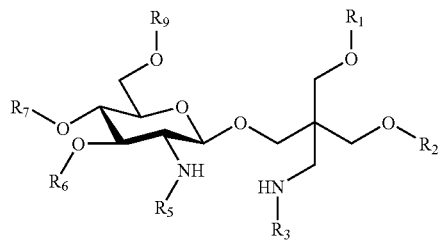

wherein $R_1$, $R_3$, $R_5$ and $R_6$ are independently hydrogen or a lipophilic group selected from the group consisting of wherein X, $X_1$, $X_2$, and $X_3$ are independently —CO— or —CH$_2$—; Z is —NH— or —O—; k, m, and r are independently an integer of 0 to 30 inclusive, n and q are independently an integer of 0 to 6 inclusive;

at least one of $R_1$, $R_3$, $R_5$ and $R_6$ is not hydrogen;

$R_2$ and $R_7$ are independently selected from the group consisting of H, —P(O)(OH)$_2$, —SO$_3$H, —P(O)(OH)(OCH$_2$CH$_2$NH$_2$), and —CH$_2$COOH; and $R_9$ is H, or an alkyl or acyl group of 1 to 10 carbon length.

113. The compound of claim 112 wherein $R_1$ and $R_9$ are hydrogen; $R_2$ is a hydrogen or the phosphono group —P(O)(OH)$_2$; $R_7$ is the phosphono group —P(O)(OH)$_2$; and $R_3$, $R_5$ and $R_6$ are the same or different acyl groups of the following structure

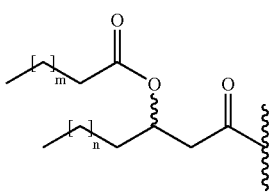

wherein m and n are independently chosen from an integer between 6 to 10 inclusive.

114. The compound of claim 113 where $R_3$, $R_5$ and $R_6$ are identical.

115. The compound of claim 114 having the following structure

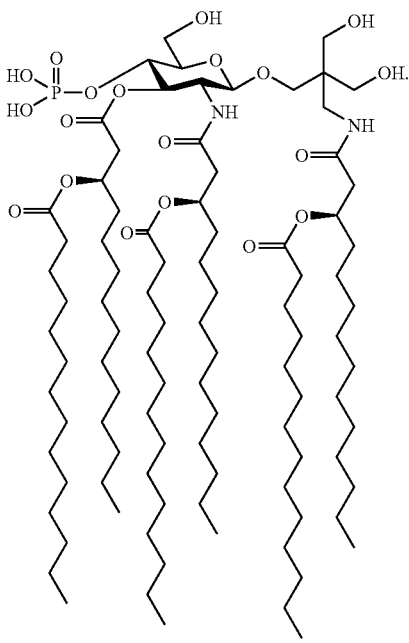

116. The compound of claim 114 having the following structure

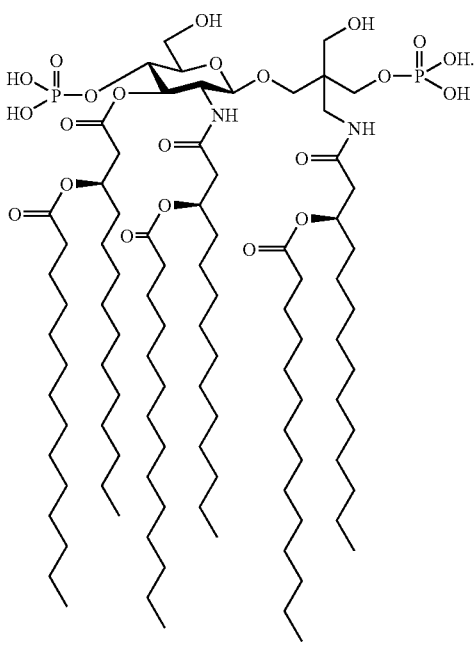

117. A method of stimulating the immune system of a mammalian subject which comprises administering to said subject an immunostimulatory amount of the compound of claim 115.

118. A method of stimulating the immune system of a mammalian subject which comprises administering to said subject an immunostimulatory amount of the compound of claim 116.

119. A compound defined by the following structure:

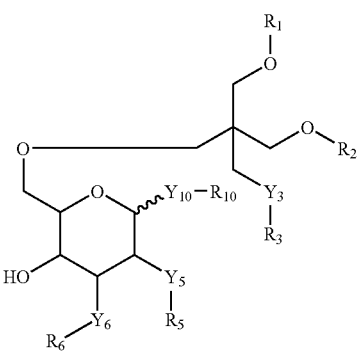

wherein $Y_3$, $Y_5$ and $Y_6$ are independently —O— or —NH—;

$Y_{10}$ is selected from the group consisting of —O—, —NH— and —S—;

$R_1$, $R_3$, $R_5$ and $R_6$ are independently hydrogen or a lipophilic group selected from the group consisting of

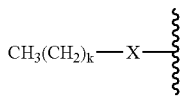

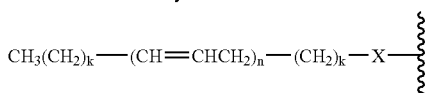

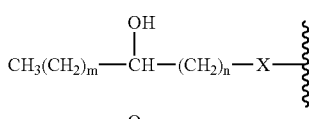

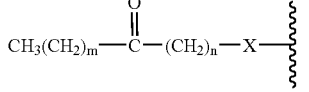

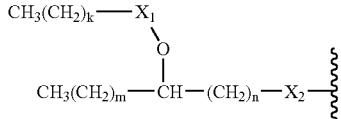

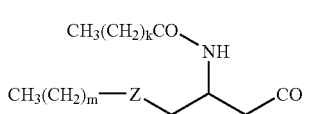

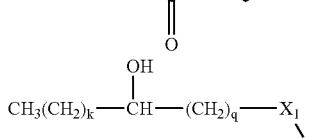

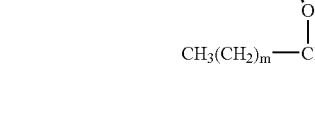

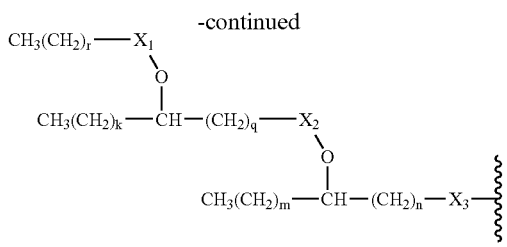

wherein X, $X_1$, $X_2$, and $X_3$ are independently CO or $CH_2$; Z is NH or O; k, m, and r are independently an integer of 0 to 30 inclusive, n and q are independently an integer of 0 to 6 inclusive;

and at least one of $R_1$, $R_3$, $R_5$ and $R_6$ is not a hydrogen atom;

$R_2$ is selected from the group consisting of H, —P(O)(OH)$_2$, —SO$_3$H, —P(O)(OH)(OCH$_2$CH$_2$NH$_2$), and —CH$_2$COOH; and $R_{10}$ is selected from the group consisting of H, —P(O)(OH)$_2$, —SO$_3$H, —P(O)(OH)(OCH$_2$CH$_2$NH$_2$)—CH$_2$COOH, and an alkyl group of 1 to 10 carbon length, or a pharmaceutically acceptable salt thereof.

120. A compound of claim 119 where the structure is further defined as the following

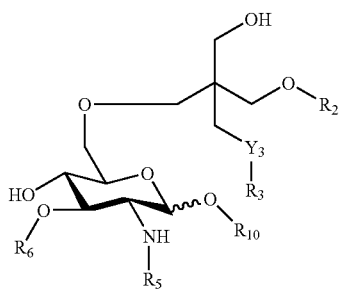

wherein $R_2$ and $R_{10}$ are independently hydrogen or a phosphono group (—P(O)(OH)$_2$), and at least one of them is the phosphono group;

$Y_3$ is —O— or —NH—, $R_3$, $R_5$, and $R_6$ are independently hydrogen or a lipophilic group selected from the group consisting of

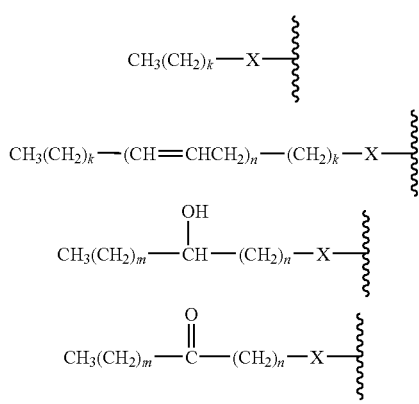

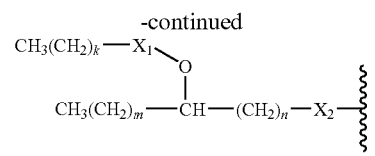

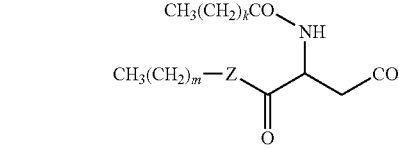

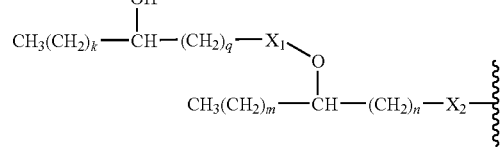

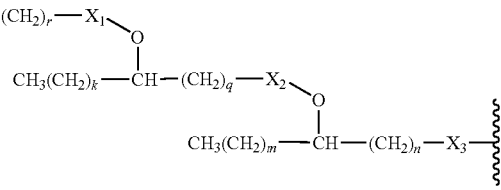

wherein X, $X_1$, $X_2$, and $X_3$ are independently CO or $CH_2$; Z is NH or O; k, m, and r are independently an integer of 0 to 30 inclusive, n and q are independently an integer of 0 to 6 inclusive; and at least one of $R_3$, $R_5$, and $R_6$ is not hydrogen.

121. The compound of claim 120 where the structure is further defined as the following

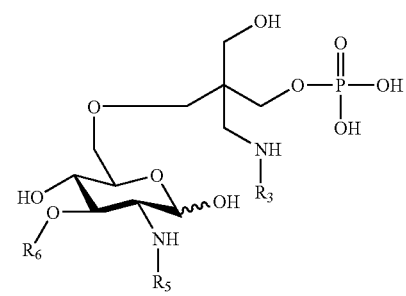

wherein $R_3$, $R_5$ and $R_6$ are the same or different substitution group(s) of the following structure

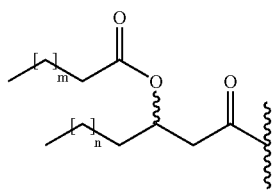

wherein m and n are independently chosen from an integer between 6 to 10 inclusive.

122. A compound of claim 25 where the structure is further defined by the following

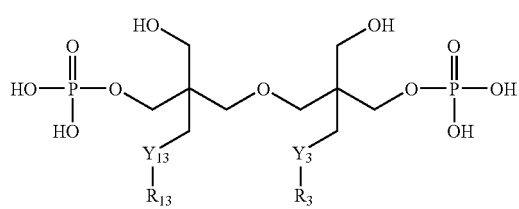

wherein $Y_3$ and $Y_{13}$ are independently —O— or —NH—;
$R_3$ and $R_{13}$ are the same substitution group and are a strongly lipophilic group selected from the group consisting of:

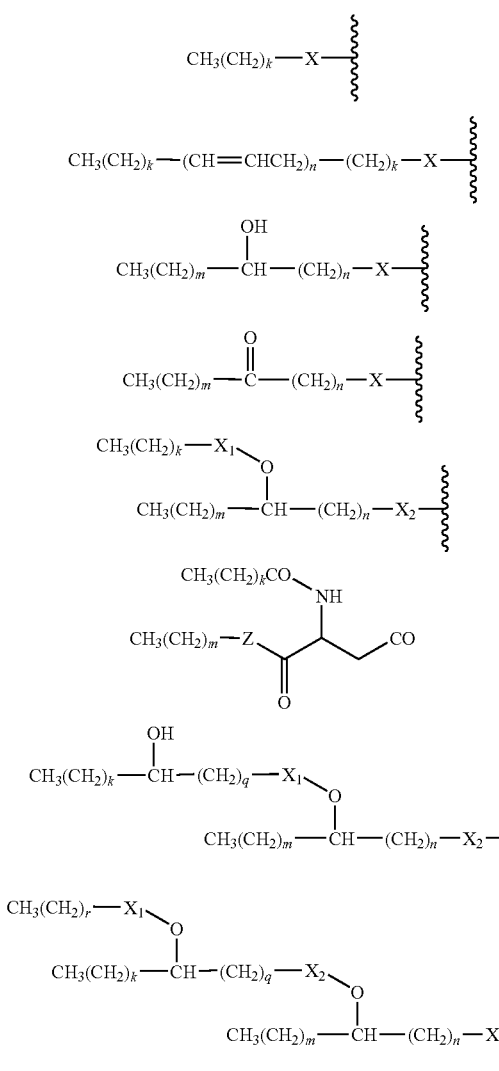

wherein X, $X_1$, $X_2$, and $X_3$ are independently CO or $CH_2$; Z is NH and O; k, m, and r are independently an integer of 0 to 30 inclusive, n and q are independently an integer of 0 to 6 inclusive.

123. The compound of claim 122 having the following structure

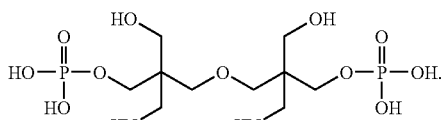

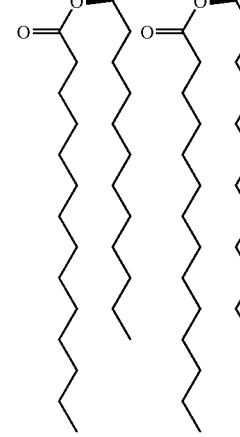

124. The compound of claim 122 having the following structure

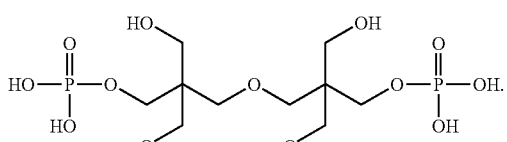

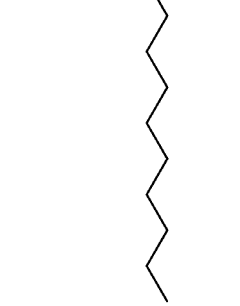

125. The compound of claim 1, wherein the strongly lipophilic groups of said compound collectively provide at least three major carbon chains, and wherein the major carbon chains of said strongly lipophilic groups collectively provide at least 40 carbon atoms.

126. The compound of claim 1 wherein the strongly lipophilic groups of said compound collectively provide at least four major carbon chains and wherein the major carbon chains collectively provide at least 50 carbon atoms.

127. The compound of claim 2 wherein the strongly lipophilic groups of said compound collectively provide at least four major carbon chains and wherein the major carbon chains collectively provide at least 50 carbon atoms.

128. The compound of claim 126 in which structure (II) applies, and in which at least two major carbon chains are connected, without any intermediate Pet unit, to the first Pet unit, and at least two major carbon chains are connected, without any intermediate Pet unit, to the second Pet unit.

129. The compound of claim 127 in which at least two major carbon chains are connected, without any intermediate Pet unit, to the sugar unit, and at least two major carbon chains are connected, without any intermediate sugar unit, to the Pet unit.

130. The compound of claim 128 wherein the strongly lipophilic groups collectively provide six major carbon chains.

131. The compound of claim 129 wherein the strongly lipophilic groups collectively provide six major carbon chains.

132. The compound of claim 1 wherein each major carbon chain is characterized by 10, 12, 14, 16, 18 or 20 carbon atoms in said chain.

133. The compound of claim 125 wherein each major carbon chain is characterized by 10, 12, 14, 16, 18 or 20 carbon atoms in said chain.

134. The compound of claim 126 where each major carbon chain is 10, 12, 14, 16, 18 or 20 carbons.

135. The compound of claim 127 where each major carbon chain is 10, 12, 14, 16, 18 or 20 carbons.

136. The compound of claim 128 where each major carbon chain is 10, 12, 14, 16, 18 or 20 carbons.

137. The compound of claim 1 which has lipid A antagonist activity.

138. A method of inhibiting an adverse lipid A activity in a mammalian subject which comprises administering to said subject an inhibitory amount of the compound of claim 137.

139. The method of claim 138 in which the subject is suffering from septic shock.

140. The method of claim 138 in which the subject is suffering from an infection.

141. The compound of claim 125 which has immunostimulatory activity.

142. A method of stimulating the immune system of a mammalian subject which comprises administering to said subject an immunostimulatory amount of the compound of claim 141.

143. The method of claim 142 which further comprises administering to the subject an immunologically effective amount of an immunogen, the immune response to said immunogen being enhanced by said compound.

144. The method of claim 143 in which the immunogen is a disease-associated immunogen and the subject suffers from that disease.

145. The method of claim 143 in which the immunogen is a tumor-associated immunogen.

146. The method of claim 143 in which the immunogen comprises a carbohydrate epitope.

147. The method of claim 146 in which the immunogen comprises a Tn, TF or sialyl-Tn epitope.

148. The method of claim 143 in which the immunogen comprises a peptide epitope.

149. The method of claim 148 in which the immunogen comprises a MUC1 epitope.

150. The method of claim 143 in which the immunogen comprises a strongly lipophilic group.

151. The method of claim 143 in which the compound is delivered by means of a liposomal formulation.

152. The method of claim 143 in which the immunogen is delivered by means of a liposomal formulation.

* * * * *